United States Patent
Reed et al.

(10) Patent No.: US 10,632,191 B2
(45) Date of Patent: *Apr. 28, 2020

(54) SYNTHETIC GLUCOPYRANOSYL LIPID ADJUVANTS

(71) Applicant: Infectious Disease Research Institute, Seattle, WA (US)

(72) Inventors: Steven G. Reed, Bellevue, WA (US); Darrick Carter, Seattle, WA (US)

(73) Assignee: Infectious Disease Research Institute, Seattle, WA (US)

( * ) Notice: Subject to any disclaimer, the term of this patent is extended or adjusted under 35 U.S.C. 154(b) by 46 days.

This patent is subject to a terminal disclaimer.

(21) Appl. No.: 15/729,512

(22) Filed: Oct. 10, 2017

(65) Prior Publication Data

US 2018/0028649 A1 Feb. 1, 2018

Related U.S. Application Data

(63) Continuation of application No. 15/285,378, filed on Oct. 4, 2016, now Pat. No. 9,814,772, which is a continuation of application No. 14/222,481, filed on Mar. 21, 2014, now Pat. No. 9,480,740, which is a continuation of application No. 12/794,336, filed on Jun. 4, 2010, now Pat. No. 8,722,064.

(60) Provisional application No. 61/184,703, filed on Jun. 5, 2009.

(51) Int. Cl.
| | |
|---|---|
| *C07H 15/00* | (2006.01) |
| *A61K 39/39* | (2006.01) |
| *A61K 31/7016* | (2006.01) |
| *A61K 39/00* | (2006.01) |
| *A61K 39/04* | (2006.01) |
| *C07H 15/12* | (2006.01) |
| *C07H 15/04* | (2006.01) |
| *A61K 39/21* | (2006.01) |
| *A61K 39/235* | (2006.01) |
| *A61K 39/245* | (2006.01) |
| *A61K 39/275* | (2006.01) |
| *C07H 15/20* | (2006.01) |
| *A61K 9/107* | (2006.01) |
| *A61K 31/665* | (2006.01) |

(52) U.S. Cl.
CPC ............. *A61K 39/39* (2013.01); *A61K 9/107* (2013.01); *A61K 31/665* (2013.01); *A61K 31/7016* (2013.01); *A61K 39/00* (2013.01); *A61K 39/04* (2013.01); *A61K 39/21* (2013.01); *A61K 39/235* (2013.01); *A61K 39/245* (2013.01); *A61K 39/275* (2013.01); *C07H 15/04* (2013.01); *C07H 15/12* (2013.01); *C07H 15/20* (2013.01); *A61K 2039/525* (2013.01); *A61K 2039/55572* (2013.01); *A61K 2039/57* (2013.01); *A61K 2039/575* (2013.01)

(58) Field of Classification Search
None
See application file for complete search history.

(56) References Cited

U.S. PATENT DOCUMENTS

| | | |
|---|---|---|
| 3,238,190 A | 3/1966 | Erbring et al. |
| 3,598,122 A | 8/1971 | Zaffaroni |
| 3,598,123 A | 8/1971 | Zaffaroni |
| 4,029,762 A | 6/1977 | Galanos et al. |
| 4,286,592 A | 9/1981 | Chandrasekaran |
| 4,314,557 A | 2/1982 | Chandrasekaran |
| 4,379,454 A | 4/1983 | Campbell et al. |
| 4,420,461 A | 12/1983 | Reckel et al. |
| 4,420,558 A | 12/1983 | De Mey et al. |
| 4,568,343 A | 2/1986 | Leeper et al. |
| 4,595,654 A | 6/1986 | Reckel et al. |
| 4,614,722 A | 9/1986 | Pasula |
| 4,629,722 A | 12/1986 | Ribi |
| 4,659,659 A | 4/1987 | Dwek et al. |
| 4,743,540 A | 5/1988 | Ralph et al. |

(Continued)

FOREIGN PATENT DOCUMENTS

| | | |
|---|---|---|
| CN | 101138566 A | 3/2008 |
| DE | 3 833 319 A1 | 4/1989 |

(Continued)

OTHER PUBLICATIONS

Fukuoka et al. (Archives of Microbiology, 1992, 157(4), pp. 311-318 (Year: 1992).*

(Continued)

*Primary Examiner* — Traviss C McIntosh, III
(74) *Attorney, Agent, or Firm* — Newport IP, LLC; Benjamin A. Keim

(57) ABSTRACT

Compounds, particularly, glucopyranosyl lipid adjuvant (GLA) compounds, having the following structure (I) are provided:

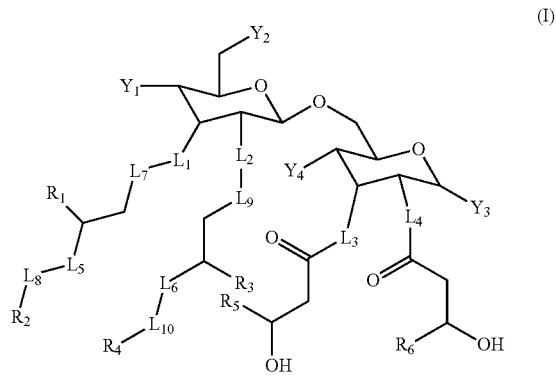

or a pharmaceutically acceptable salt thereof, wherein $L_1$, $L_2$, $L_3$, $L_4$, $L_5$, $L_6$, $L_7$, $L_8$, $L_9$, $L_{10}$, $Y_1$, $Y_2$, $Y_3$, $Y_4$, $R_1$, $R_2$, $R_3$, $R_4$, $R_5$, $R_6$, are as defined herein. Pharmaceutical compositions, vaccine compositions, and related methods for inducing or enhancing immune responses, are also provided.

15 Claims, 10 Drawing Sheets

(56) References Cited

U.S. PATENT DOCUMENTS

| | | |
|---|---|---|
| 4,767,402 A | 8/1988 | Kost et al. |
| 4,769,330 A | 9/1988 | Paoletti et al. |
| 4,780,212 A | 10/1988 | Kost et al. |
| 4,844,894 A | 7/1989 | Ribi |
| 4,897,268 A | 1/1990 | Tice et al. |
| 4,912,094 A | 3/1990 | Myers et al. |
| 4,948,587 A | 8/1990 | Kost et al. |
| 4,981,684 A | 1/1991 | MacKenzie et al. |
| 4,987,237 A | 1/1991 | Myers et al. |
| 5,017,487 A | 5/1991 | Stunnenberg et al. |
| 5,057,540 A | 10/1991 | Kensil et al. |
| 5,066,794 A | 11/1991 | Shiba |
| 5,075,109 A | 12/1991 | Tice et al. |
| 5,124,141 A | 6/1992 | Makler |
| 5,147,785 A | 9/1992 | Pasula |
| 5,162,990 A | 11/1992 | Odeyale et al. |
| 5,231,168 A | 7/1993 | Dziegiel et al. |
| 5,278,302 A | 1/1994 | Caruthers et al. |
| 5,298,396 A | 3/1994 | Kotzin et al. |
| 5,411,865 A | 5/1995 | Reed |
| 5,422,109 A | 6/1995 | Brancq et al. |
| 5,424,067 A | 6/1995 | Brancq et al. |
| 5,457,041 A | 10/1995 | Ginaven et al. |
| 5,464,387 A | 11/1995 | Haak et al. |
| 5,530,113 A | 6/1996 | Christ et al. |
| 5,565,209 A | 10/1996 | Rijke |
| 5,591,139 A | 1/1997 | Lin et al. |
| 5,595,888 A | 1/1997 | Gray et al. |
| 5,612,041 A | 3/1997 | Burke et al. |
| 5,612,476 A | 3/1997 | Christ et al. |
| 5,618,275 A | 4/1997 | Bock |
| 5,650,155 A | 7/1997 | Cornelius et al. |
| 5,654,140 A | 8/1997 | Persico et al. |
| 5,656,016 A | 8/1997 | Ogden |
| 5,666,153 A | 9/1997 | Copeland |
| 5,667,784 A | 9/1997 | Cornelius et al. |
| 5,693,531 A | 12/1997 | Chiorini et al. |
| 5,718,904 A | 2/1998 | Hjorth |
| 5,719,263 A | 2/1998 | Reed |
| 5,722,397 A | 3/1998 | Eppstein |
| 5,756,718 A | 5/1998 | Christ et al. |
| 5,776,468 A | 7/1998 | Hauser et al. |
| 5,786,148 A | 7/1998 | Bandman et al. |
| 5,795,577 A | 8/1998 | Kieny et al. |
| 5,840,871 A | 11/1998 | Hillman et al. |
| 5,843,464 A | 12/1998 | Bakaletz et al. |
| 5,843,918 A | 12/1998 | Christ et al. |
| 5,846,758 A | 12/1998 | Medenica |
| 5,885,211 A | 3/1999 | Eppstein et al. |
| 5,888,519 A | 3/1999 | Alving |
| 5,912,166 A | 6/1999 | Reed et al. |
| 5,952,309 A | 9/1999 | Rossignol et al. |
| 5,955,306 A | 9/1999 | Gimeno et al. |
| 5,961,970 A | 10/1999 | Lowell et al. |
| 5,976,538 A | 11/1999 | Hilgers et al. |
| 5,981,215 A | 11/1999 | Meissner et al. |
| 5,993,800 A | 11/1999 | Linsley et al. |
| 6,005,099 A | 12/1999 | Davies et al. |
| 6,018,678 A | 1/2000 | Mitragotri et al. |
| 6,027,730 A | 2/2000 | Francotte et al. |
| 6,027,732 A | 2/2000 | Morein et al. |
| 6,033,928 A | 3/2000 | Eriguchi et al. |
| 6,057,427 A | 5/2000 | Smith et al. |
| 6,106,824 A | 8/2000 | Kaplitt et al. |
| 6,120,769 A | 9/2000 | Gefter et al. |
| 6,146,632 A | 11/2000 | Momin et al. |
| 6,218,186 B1 | 4/2001 | Choi et al. |
| 6,231,861 B1 | 5/2001 | Barnwell |
| 6,235,724 B1 | 5/2001 | Asai et al. |
| 6,261,762 B1 | 7/2001 | Alizon et al. |
| 6,270,769 B1 | 8/2001 | Raychaudhuri et al. |
| 6,309,847 B1 | 10/2001 | Cohen et al. |
| 6,316,183 B1 | 11/2001 | Alizon et al. |
| 6,322,532 B1 | 11/2001 | D'Sa et al. |
| 6,375,944 B1 | 4/2002 | Trinchieri et al. |
| 6,472,515 B1 | 10/2002 | Climent-Johansson et al. |
| 6,488,936 B1 | 12/2002 | Mishkin et al. |
| 6,491,919 B2 | 12/2002 | Crane |
| 6,512,102 B1 | 1/2003 | Xu et al. |
| 6,544,518 B1 | 4/2003 | Friede et al. |
| 6,544,728 B1 | 4/2003 | Alizon et al. |
| 6,555,653 B2 | 4/2003 | Alderson et al. |
| 6,572,861 B1 | 6/2003 | Roberts et al. |
| 6,587,792 B1 | 7/2003 | Thomas |
| 6,596,501 B2 | 7/2003 | Roth |
| 6,613,892 B2 | 9/2003 | Preston et al. |
| 6,630,161 B1 | 10/2003 | Leesman |
| 6,654,462 B1 | 11/2003 | Hedberg |
| 6,660,487 B2 | 12/2003 | Faustman |
| 6,676,961 B1 | 1/2004 | Lichter |
| 6,682,901 B2 | 1/2004 | Blaschuk et al. |
| 6,683,063 B2 | 1/2004 | Rossignol et al. |
| 6,685,699 B1 | 2/2004 | Eppstein et al. |
| 6,692,752 B1 | 2/2004 | Slaoui et al. |
| 6,706,872 B1 | 3/2004 | Barnwell |
| 6,713,068 B1 | 3/2004 | Audonnet et al. |
| 6,733,763 B2 | 5/2004 | Raychaudhuri et al. |
| 6,734,172 B2 | 5/2004 | Scholler et al. |
| 6,749,856 B1 | 6/2004 | Berzofsky et al. |
| 6,752,995 B2 | 6/2004 | Johnston et al. |
| 6,770,445 B1 | 8/2004 | Scholler et al. |
| 6,783,981 B1 | 8/2004 | Uden et al. |
| 6,797,276 B1 | 9/2004 | Glenn et al. |
| 6,828,155 B1 | 12/2004 | Kaneko et al. |
| 6,844,192 B2 | 1/2005 | Orlando et al. |
| 6,846,489 B1 | 1/2005 | Garcon et al. |
| 6,846,648 B2 | 1/2005 | Maes |
| 6,855,322 B2 | 2/2005 | Lyon et al. |
| 6,869,607 B1 | 3/2005 | Buschle et al. |
| 6,871,477 B1 | 3/2005 | Tucker |
| 6,875,610 B2 | 4/2005 | Higginbotham et al. |
| 6,893,820 B1 | 5/2005 | Plass |
| 6,908,453 B2 | 6/2005 | Fleming et al. |
| 6,911,434 B2 | 6/2005 | Baldridge et al. |
| 6,919,078 B2 | 7/2005 | Ni et al. |
| 6,919,210 B1 | 7/2005 | Okamoto |
| 6,929,796 B1 | 8/2005 | Conti-Fine |
| 6,932,972 B2 | 8/2005 | Stephenne et al. |
| 6,933,123 B2 | 8/2005 | Hu et al. |
| 6,936,255 B1 | 8/2005 | Wettendorff |
| 6,949,246 B2 | 9/2005 | Reed et al. |
| 6,969,704 B1 | 11/2005 | Pinsky et al. |
| 6,970,739 B1 | 11/2005 | Inoue |
| 6,974,588 B1 | 12/2005 | Miranda et al. |
| 6,977,073 B1 | 12/2005 | Cezayirli et al. |
| 6,979,535 B2 | 12/2005 | Alizon et al. |
| 6,979,730 B2 | 12/2005 | Reiter et al. |
| 6,991,791 B2 | 1/2006 | Le et al. |
| 7,001,770 B1 | 2/2006 | Atencio et al. |
| 7,008,774 B2 | 3/2006 | Ryan et al. |
| 7,012,134 B2 | 3/2006 | Ruben et al. |
| 7,018,345 B2 | 3/2006 | Mori et al. |
| 7,029,678 B2 | 4/2006 | Momin et al. |
| 7,029,685 B2 | 4/2006 | Lanar et al. |
| 7,030,232 B1 | 4/2006 | Reiter et al. |
| 7,033,598 B2 | 4/2006 | Lerner |
| 7,037,712 B2 | 5/2006 | Both et al. |
| 7,052,904 B2 | 5/2006 | Zheng et al. |
| 7,060,276 B2 | 6/2006 | Lanar et al. |
| 7,060,802 B1 | 6/2006 | Trakht et al. |
| 7,067,310 B2 | 6/2006 | Chartier et al. |
| 7,070,931 B2 | 7/2006 | Fujinaga et al. |
| 7,078,180 B2 | 7/2006 | Genetta |
| 7,084,256 B2 | 8/2006 | McCormick et al. |
| 7,087,231 B2 | 8/2006 | Guerin-Marchand et al. |
| 7,087,713 B2 | 8/2006 | Campos-Neto et al. |
| 7,357,936 B1 | 4/2008 | Garcon |
| 8,273,361 B2* | 9/2012 | Reed .................. A61K 39/0011<br>424/282.1 |
| 8,343,512 B2* | 1/2013 | Reed .................. A61K 39/008<br>424/275.1 |
| 8,609,114 B2* | 12/2013 | Reed .................. A61K 39/0011<br>424/278.1 |

(56) References Cited

U.S. PATENT DOCUMENTS

| | | | |
|---|---|---|---|
| 8,722,064 B2* | 5/2014 | Reed | A61K 39/00 424/278.1 |
| 8,840,908 B2* | 9/2014 | Reed | A61K 39/0011 424/280.1 |
| 8,957,047 B2* | 2/2015 | Paya Cuenca | C07K 16/2887 514/53 |
| 9,463,198 B2 | 10/2016 | Ben-Eliyahu et al. | |
| 9,480,740 B2* | 11/2016 | Reed | A61K 39/00 |
| 9,814,772 B2* | 11/2017 | Reed | A61K 39/00 |
| 9,907,845 B2* | 3/2018 | Reed | A61K 39/0011 |
| 9,950,063 B2* | 4/2018 | Reed | A61K 39/0011 |
| 9,987,355 B2* | 6/2018 | Reed | A61K 39/0011 |
| 2002/0176867 A1 | 11/2002 | Andersen et al. | |
| 2003/0165512 A1 | 9/2003 | Wheeler et al. | |
| 2003/0170249 A1 | 9/2003 | Hakomori et al. | |
| 2003/0215497 A1 | 11/2003 | Leesman | |
| 2004/0120924 A1 | 6/2004 | Hone et al. | |
| 2004/0161776 A1 | 8/2004 | Maddon et al. | |
| 2005/0123550 A1 | 6/2005 | Laurent et al. | |
| 2007/0072824 A1 | 3/2007 | Kawano et al. | |
| 2008/0131466 A1 | 6/2008 | Reed et al. | |
| 2009/0181078 A1 | 7/2009 | Reed et al. | |
| 2010/0310602 A1 | 12/2010 | Reed et al. | |
| 2011/0014274 A1 | 1/2011 | Reed et al. | |
| 2011/0070290 A1 | 3/2011 | Reed et al. | |
| 2013/0058997 A1 | 3/2013 | Reed et al. | |
| 2013/0084307 A1 | 4/2013 | Reed et al. | |
| 2014/0037691 A1 | 2/2014 | Reed et al. | |
| 2014/0193459 A1 | 7/2014 | Reed et al. | |
| 2014/0341970 A1 | 11/2014 | Reed et al. | |
| 2015/0017191 A1 | 1/2015 | Fox et al. | |
| 2015/0335736 A1 | 11/2015 | Reed et al. | |

FOREIGN PATENT DOCUMENTS

| | | |
|---|---|---|
| EP | 0 172 581 A2 | 2/1986 |
| EP | 0 172 581 A3 | 2/1986 |
| EP | 0 224 260 A2 | 6/1987 |
| EP | 0 324 455 A2 | 7/1989 |
| EP | 0 366 412 A2 | 5/1990 |
| EP | 0 109 942 B1 | 3/1991 |
| EP | 0 468 520 A2 | 1/1992 |
| EP | 0 382 271 B1 | 12/1994 |
| EP | 0 198 474 B1 | 6/1996 |
| EP | 0 414 374 B1 | 10/1997 |
| EP | 0 362 279 B2 | 11/1999 |
| EP | 0 761 231 B1 | 1/2000 |
| EP | 0 729 473 B1 | 8/2000 |
| EP | 0 304 578 B1 | 10/2001 |
| EP | 1 531 158 B1 | 9/2006 |
| GB | 2 220 211 A | 1/1990 |
| GB | 2 232 892 A | 1/1991 |
| JP | 63-10728 A | 1/1988 |
| JP | 5-328975 A | 12/1993 |
| JP | 10-131046 A | 5/1998 |
| JP | 2000-095694 A | 4/2000 |
| RU | 2 288 723 C2 | 12/2006 |
| WO | WO-89/01973 A2 | 3/1989 |
| WO | WO-90/01496 A1 | 2/1990 |
| WO | WO-90/06951 A1 | 6/1990 |
| WO | WO-90/07936 A1 | 7/1990 |
| WO | WO-91/00106 A1 | 1/1991 |
| WO | WO-91/00107 A1 | 1/1991 |
| WO | WO-91/02805 A2 | 3/1991 |
| WO | WO-93/02184 A1 | 2/1993 |
| WO | WO-93/10152 A1 | 5/1993 |
| WO | WO-93/12778 A1 | 7/1993 |
| WO | WO-93/25234 A1 | 12/1993 |
| WO | WO-93/25698 A1 | 12/1993 |
| WO | WO-94/00152 A1 | 1/1994 |
| WO | WO-94/00153 A1 | 1/1994 |
| WO | WO-94/03622 A1 | 2/1994 |
| WO | WO-94/05792 A1 | 3/1994 |
| WO | WO-94/20137 A1 | 9/1994 |
| WO | WO-94/21292 A1 | 9/1994 |
| WO | WO-95/14026 A1 | 5/1995 |
| WO | WO-95/17209 A1 | 6/1995 |
| WO | WO-95/17210 A1 | 6/1995 |
| WO | WO-95/20600 A1 | 8/1995 |
| WO | WO-95/26204 A1 | 10/1995 |
| WO | WO-96/02555 A1 | 2/1996 |
| WO | WO-96/09310 A1 | 3/1996 |
| WO | WO-96/11272 A2 | 4/1996 |
| WO | WO-96/11711 A1 | 4/1996 |
| WO | WO-96/26277 A1 | 8/1996 |
| WO | WO-96/33739 A1 | 10/1996 |
| WO | WO-97/11708 A1 | 4/1997 |
| WO | WO-98/01139 A1 | 1/1998 |
| WO | WO-98/12302 A1 | 3/1998 |
| WO | WO-98/16247 A1 | 4/1998 |
| WO | WO-98/20117 A1 | 5/1998 |
| WO | WO-98/37418 A2 | 8/1998 |
| WO | WO-98/43670 A2 | 10/1998 |
| WO | WO-98/56414 A1 | 12/1998 |
| WO | WO-98/58956 | 12/1998 |
| WO | WO-99/03884 A2 | 1/1999 |
| WO | WO-99/10375 A2 | 3/1999 |
| WO | WO-99/10375 A3 | 3/1999 |
| WO | WO-99/11241 A1 | 3/1999 |
| WO | WO-99/12565 A1 | 3/1999 |
| WO | WO-99/17741 A1 | 4/1999 |
| WO | WO-99/28475 A2 | 6/1999 |
| WO | WO-99/40188 A2 | 8/1999 |
| WO | WO-99/51748 A2 | 10/1999 |
| WO | WO-99/53061 A2 | 10/1999 |
| WO | WO-00/04149 A2 | 1/2000 |
| WO | WO-00/13029 A1 | 3/2000 |
| WO | WO-00/18929 A2 | 4/2000 |
| WO | WO-00/25815 A1 | 5/2000 |
| WO | WO-00/42994 A2 | 7/2000 |
| WO | WO-01/36433 A2 | 5/2001 |
| WO | WO-01/90129 A2 | 11/2001 |
| WO | WO-01/90129 A3 | 11/2001 |
| WO | WO-02/16560 A1 | 2/2002 |
| WO | WO-02/28424 A2 | 4/2002 |
| WO | WO-02/32450 A2 | 4/2002 |
| WO | WO-03/066065 A1 | 8/2003 |
| WO | WO-03/094850 A2 | 11/2003 |
| WO | WO-03/094850 A3 | 11/2003 |
| WO | WO-2008/153541 A1 | 12/2008 |
| WO | WO-2009/035528 A2 | 3/2009 |
| WO | WO-2009/035528 A3 | 3/2009 |
| WO | WO-2009035528 A2 * | 3/2009 ............ C07H 11/04 |
| WO | WO-2009/143457 A2 | 11/2009 |
| WO | WO-2010/141861 A1 | 12/2010 |

OTHER PUBLICATIONS

Lukasiewicz, J. et al. (Sep. 5, 2006, e-pub. Aug. 11, 2006). "Complete Lipopolysaccharide of Plesiomonas Shigelloides O74:H5 (Strain CNCTC 144192). 2. Lipid A, Its Structural Variability, the Linkage to the Core Oligosaccharide, and the Biological Activity of the Lipopolysaccharide," Biochemistry 45(35):10434-10447.

Akamatsu et al., "Synthesis of lipid A monosaccharide analogues containing acidic amino acid: Exploring the structural basis for the endotoxic and antagonistic activities," Bioorganic & Medicinal Chemistry 14:6759-6777, 2006.

Akamizu et al., "Molecular Analysis of Stimulatory Antithyrotropin Receptor Antibodies (TSAbs) Involved in Graves' Disease," J Immunol. 157(7):3148-3152, Oct. 1996.

Alving et al., "Lipid A and liposomes containing lipid A as antigens and adjuvants," Vaccine 26:3036-3045, 2008.

American Thoracic Society, "Standards for the Diagnosis and Care of Patients with Chronic Obstructive Pulmonary Disease," Am. J Respir. Crit. Care Med. 152(5 Pt 2):S77-S121, 1995.

Andaloussi et al., "Stimulation of TLR9 with CpG ODN Enhances Apoptosis of Glioma and Prolongs the Survival of Mice with Experimental Brain Tumors," Glia 54(6):526-535, 2006.

Apicella, M.A. et al. (Oct. 1985). "Antigenic Heterogeneity of Lipid A of Haemophilus influenzae," Infection and Immunity 50(1):9-14.

(56) References Cited

OTHER PUBLICATIONS

Armant et al., "Toll-like Receptors: A Family of Pattern-recognition Receptors in Mammals," *Genome Biol.* 3(8): reviews 3011.1-3011. 6, Jul. 29, 2002.

Asai, Y., "Development of an Injectable Formulation for the Novel Lipid A Analog E5531 Using a 'pH-jump Method,'" *Yakugaku Zasshi* 124(12):965-972, 2004.

Avanti Polar Lipids, Inc., Product Data Sheet for Avanti Product No. 699200, Lipid A Purified Detoxified Lipid A, http://www.avantilipds.com, download date Jan. 14, 2009.

Avanti Polar Lipids, Inc., Product Data Sheet for Avanti Product No. 699800, Lipid A (Synthetic )(PHAD™) Monophosphoryl Lipid A (Synthetic )(Phad™) http://www.avantilipds.com, download date Jan. 14, 2009.

Avanti, "Advertising: Synthetic Adjuvant," *Journal of Immunology* [Online] 178(10): 1-5, May 15, 2007; XP002546530.

Avanti, "Advertising: The New PHAD(tm) In Vaccine Technology Avanti's Synthetic Vaccine Adjuvant," *Journal of Immunology* [Online] 179(12): 1-6, Dec. 15, 2007; XP002546531.

Badaro et al., "Evaluation of Micro Enzyme-linked Immunosorbent Assay (ELISA) for Antibodies in American Visceral Leishmaniasis: Antigen Selection for Detection of Infection-Specific Responses," *Am. J Trap. Med. Hyg.* 35:72-78, 1986.

Badaro et al., "rK39: A Cloned Antigen of Leishmania Chagasi that Predicts Active Visceral Leishmaniasis," *J Inf Dis.* 173(3):758-761, Mar. 1996.

Bainbridge et al., "Expression of a Porphyromonas gingivalis lipid a palmitylacyltransferase in *Escherichia coli* yields a chimeric lipid A with altered ability to stimulate interleukin-8 secretion," *Cellular Microbiology* 8(1): 120-129, 2006.

Baldridge et al., "Monophosphoryl Lipid A (MPL) Formulations for the Next Generation of Vaccines," *Methods* 19:103-107, 1999.

Baldridge et al., "Monophosphoryl lipid A enhances mucosol and systemic immunity to vaccine antigens following intranasal administration," *Vaccine* 18:2416-2425, 2000.

Bayes et al., "Gateways to Clinical Trials," *Methods Find Exp. Clin. Pharmacol.* 27(3):193-219, Apr. 2005.

Berkner, "Development of Adenovirus Vectors for the Expression of Heterologous Genes," *Biotechniques* 6(7):616-627, 1988.

Beutler et al., "Cachectin and Tumour Necrosis Factor as Two Sides of the Same Biological Coin," *Nature* 320:584-588, Apr. 1986.

Bomford et al., "Adjuvanticity and ISCOM Formation by Structurally Diverse Saponins," *Vaccine* 10(9):572-577, 1992.

Borges et al., "Potent Stimulation of the Innate Immune System by a *Leishmania brasiliensis* Recombinant Protein," *Infection and Immunity* 69(9):5270-5277, Sep. 2001.

Brandenberg, "Fourier transform infrared spectroscopy characterization of the lamellar and nonlamellar structures of free lipid A and Re lipopolysaccharides from *Salmonella minnesota* and *Escherichia coli*," *Biophys. J.* 64:1215-1231, 1993.

Brandenburg et al., "Endotoxins: Relationships between Structure, Function, and Activity," *Current Topics in Medicinal Chemistry* 4(11):1127-1146, 2004.

Bray et al. "The Immunology and Serology of Leishmaniasis. IV. Result of Ouchterlony Double Diffusion Tests," *Trans. R. Soc. Trop. Med. Hyg.* 60(5):605-609, 1966.

Brazolot Millan et al., "CpG DNA can Induce Strong Th1 Humoral and Cell Mediated Immune Responses Against Hepatitis B Surface Antigen in Young Mice," *Proc. Natl. Acad. Sci. USA* 95(26):15553-15558, Dec. 22, 1998.

Bulusu et al., "Acyclic analogs of lipid A: synthesis and biological activities," *J of Medicinal Chemistry* 35(19):3463-3469, 1992.

Campagnari, A.A. et al. (Aug. 1991). "Role of Lipooligosaccharides in Experimental Dermal Lesions Caused by *Haemophilus ducreyi*," *Infection and Immunity* 59(8):2601-2608.

Casale et al., "Safety of the intranasal toll-like receptor 4 agonist CRX-675 in allergic rhinitis," *Annals of Allergy, Asthma & Immunology* 97(4): 454-456, Oct. 2006.

Casella et al., "Putting endotoxin to work for us: Monophosphoryl-lipid A as a safe and effective vaccine adjuvant," *Cell. Mol. Life Sci.* 65:3231-3240, 2008.

Chen et al., "Distinct Responses of Lung and Spleen Dendritic Cells to the TLR9 Against CpG Oligodeoxynucleotide," *J Immunol.* 177(4):2373-2383, 2006.

Choudhry et al., "Enzyme-Linked Immunosorbent Assay in the Diagnosis of Kala-azar in Bhadohi (Varanasi), India," *Trans. R. Soc. Trap. Med. Hyg.* 84(3):363-366, May 1990.

Choudhry et al., "An Indirect Fluorescent Antibody (IF A) Test for the Serodiagnosis of Kala-Azar," *J Comm. Dis.* 24(1):32-36, Mar. 1992.

Ciprandi et al., "Emerging anti-inflammatory agents for allergic rhinitis," *Expert Opinion on Emerging Drugs* 10(4): 689-705, Nov. 2005.

Coler et al., "Immunization with a Polyprotein Vaccine Consisting of the T-Cell Antigens Thiol-Specific Antioxidant, *Leishmania major* Stress-Inducible Protein 1, and *Leishmania* Elongation Initiation Factor Protects against Leishmaniasis," *Infection and Immunity* 70(8):4215-4225, Aug. 2002.

Cooper et al., "CPG 7909 Adjuvant Improves Hepatitis B Virus Vaccine Seroprotection in Antiretroviral-Treated HIV-Infected Adults," *AIDS* 19(14):1473-1479, Sep. 2005.

Correale et al., "In Vitro Generation of Human Cytotoxic T Lymphocytes Specific for Peptides Derived from Prostate-Specific Antigen," *J National Cancer Institute* 89(4):293-300, Feb. 19, 1997.

Cotten et al., "High-Efficiency Receptor-Mediated Delivery of Small and Large (48 Kilobase Gene Constructs Using the Endosome-Disruption Activity of Defective or Chemically Inactivated Adenovirus Particles," *Proc. Natl. Acad. Sci. USA* 89(13):6094-6098, Jul. 1992.

Curiel et al., "High Efficiency Gene Transfer Mediated by Adenovirus Coupled to DNA—Polylysine Complexes," *Hum. Gene Ther.* 3(2):147-154, Apr. 1992.

Datta et al., "A Subset of Toll-Like Receptor Ligands Induces Cross-Presentation by Bone Marrow-Derived Dendritic Cells," *J Immunol.* 170(8):4102-4110, Apr. 2003.

Davis et al., "CpG DNA is a Potent Enhancer of Specific Immunity in Mice Immunized with Recombinant Hepatitis B Surface Antigen," *J Immunol.* 160(2):870-876, Jan. 1998.

Declaration of Dr. David T. Hickman submitted in support of opposition of European Patent No. EP-2 068 918 B1, executed on Jan. 31, 2013, 23 pages.

Declaration of Dr. Maria Pilar Lopez-Deber submitted in support of opposition of European Patent No. EP-2 068 918 B1, executed on Jan. 31, 2013, 23 pages.

Deng et al., "CpG Oligodeoxynucleotides Stimulate Protective Innate Immunity Against Pulmonary *Klebsiella* Infection," *J Immunol.* 173:5148-5155, 2004.

Edelman, "Vaccine Adjuvants," *Rev. Infect. Dis.* 2(3):370-83, May-Jun. 1980.

Edelman, "The Development and Use of Vaccine Adjuvants," *Mol. Biotechnol.* 21(2):129-148, Jun. 2002.

El-Aneed, A. et al. (2005). "Elucidation of the Molecular Structure of Lipid a Isolated from Both a Rough Mutant and a Wild Strain of *Aeromonas salmonicida* Lipopolysaccharides Using Electrospray Ionization Quadrupole Time-of-Flight Tandem Mass Spectrometry," *Rapid Communications in Mass Spectrometry* 19(12):1683-1695.

Ei-On et al., "Leishmania Donovani: Physicochemical, Immunological, and Biological Characterization of Excreted Factor from Promastigotes," *Exper. Parasitol.* 47(2):254-269, Apr. 1979.

European Application No. 07 875 082.5, Office Action dated Feb. 2, 2010.

European Application No. 10 784 178.5, Office Action dated Oct. 6, 2015, 4 pages.

Extended European Search Report dated Nov. 15, 2016, for European Patent Application No. 16186377.4, filed Aug. 30, 2016, 10 pages.

Fearon et al., "The Instructive Role of Innate Immunity in the Acquired Immune Response," *Science* 272(5258):50-54, Apr. 5, 1996.

(56) References Cited

OTHER PUBLICATIONS

Feigner et al., "Lipofection: A Highly Efficient, lipid-mediated DNA-Transfection Procedure," Proc. Natl. Acad. Sci. USA 84(21):7413-7417, Nov. 1987.
Feuillet et al., "Involvement of Toll-like Receptor 5 in the Recognition of Flagellated Bacteria," PNAS 103(33):12487-12492, Aug. 15, 2006.
Flesher, A.R. et al. (Dec. 1978). "Characterization of Lipopolysaccharide of Haemophilus influenzae," The Journal of Infectious Diseases 138(6):719-730.
Fujimoto et al., "Synthesis of lipid a and its analogues for investigation of the structural basis for their bioactivity," J Endotoxin Research 11(6):341-347, 2005.
Fukase, Y. et al. (2008, e-pub. Jul. 10, 2008). "Synthesis of Rubrivivax gelatinosus Lipid A and Analogues for Investigation of the Structural Basis for Immunostimulating and Inhibitory Activities," Bulletin of the Chemical Society of Japan 81(7):796-819.
Fukuoka, S. et al. (1992). "Structural Characterization of Lipid A Component of Erwinia carotovora Lipopolysaccharide," Archives of Microbiology 157:311-318.
Galanos et al., "Endotoxic properties of chemically synthesized lipid A part structures," Eur. J Biochem. 140:221-227, 1984.
Galanos et al., "Synthetic and natural Escherichia coli free lipid A express identical endotoxic activities," Eur. J Biochem. 148:1-5, 1985.
Garçon, "Preclinical Development of AS04," in G. Davies ( ed.), Vaccine Adjuvants, Methods in Molecular Biology 626, Springer Science+Business Media, LLC, 2010, pp. 15-27.
Garidel et al., "Divalent cations affect chain mobility and aggregate structure of lipopolysaccharide from Salmonella minnesota reflected in a decrease of its biological activity," Biochimica et Biophysica Acta 1715:122-131, 2005.
Gibson et al., "Plasmacytoid Dendritic Cells Produce Cytokines and Mature in Response to the TLR7 Agonists, Imiquimod and Resiquimod," Cell. Immunol. 218(1-2):74-86, Jul.-Aug. 2002.
Gisvold, "Digitonin and Phytosterol from the Seed of Digitalis Purpurea," Phytochem. Notes, Amer. Pharmacol. Assoc. 23(7):664-666, Jul. 1934.
Glück, "Immunopotentiating Reconstituted Influenza Virosomes (IRIVs) and other Adjuvants for Improved Presentation of Small Antigens," Vaccine 10(13):915-919, 1992.
Gorden et al., "Synthetic TLR Agonists Reveal Functional Differences Between Human TLR7 and TLR8," J Immunol. 174:1259-1268,2005.
Green et al., "Mitochondria and Apoptosis," Science 281(5381):1309-1312, Aug. 28, 1998.
Griffiths et al., "Studies toward Lipid A: Synthesis of Differentially Protected Disaccharide Fragments," J Org Chem. 62(11):3654-3658, 1997.
Najjar et al., "Human Toll-like receptor 4 recognizes host-specific LPS modifications," Nature Immunology 3(4):354-359, Apr. 2002.
Hawkins et al., "A Novel Class of Endotoxin Receptor Agonists with Simplified Structure, Toll-Like Receptor 4-Dependent Immunostimulatory Action, and Adjuvant Activity," J Pharmacology Experimental Therapeutics 300(2):655-661, 2002.
Helander, I.M. et al. (1988). "Chemical Structure of the Lipopolysaccharide of Haemophilus influenzae Strain 1-69 Rd$^-$/b$^+$. Description of a Novel Deep-Rough Chemotype," Eur. J. Biochem. 177:483-492.
Hemmi et al., "Small Anti-Viral Compounds Activate Immune Cells Via the TLR7 MyD88-Dependent Signaling Pathway," Nat. Immunol. 3(2):196-200, Feb. 2002.
Hilgers et al., "Synergistic Effects of Synthetic Adjuvants on the Humoral Immune Response," Int. Archs. Allergy Appl. Immunol. 79(4):392-396, 1986.
Hilgers et al., "Synthetic Sulpholipopolysaccharides: Novel Adjuvants for Humoral Immune Responses," Immunology 60(1):141-146, Jan. 1987.

Horsmans et al., "Isatoribine, an Agonist of TLR7, Reduces Plasma Virus Concentration in Chronic Hepatitis C Infection," Hepatol. 42(3):724-731, Sep. 2005.
Hubert et al., "STEAP: A Prostate-Specific Cell-Surface Antigen Highly Expressed in Human Prostate Tumors," PNAS 96(25):14523-14528, Dec. 7, 1999.
Imoto, M. et al. (1984). "Total Synthesis of Lipid A, Active Principle of Bacterial Endotoxin," Proc. Japan Acad., Ser. B 60(8):285-288.
Imoto et al., "Chemical Synthesis of Phosphorylated Tetraacyl Disaccharide Corresponding to a Biosynthetic Precursor of Lipid A," Tetrahedron Letters 25(25):2667-2670, 1984.
Imoto et al., "Total Synthesis of Escherichia Coli Lipid A," Tetrahedron Letters 26(12):1545-1548, 1985.
Imoto, M. et al. (Jun. 1987). "Total Synthesis of Escherichia coli Lipid A, the Endotoxically Active Principle of Cell-Surface Lipopolysaccharide," Bull. Chem. Soc. Japan 60(6):2205-2214.
Invoices for the sale of PHAD™ from Avanti Polar Lipids, Inc. to AC Immune SA (2005-2006). 4 pages.
Jacobson et al., "Epidemiology and Estimated Population Burden of Selected Autoimmune Diseases in the United States," Clin. Immunol. Immunopathol. 84(3):223-243, Sep. 1997.
Jiang et al., "Novel lipid A mimetics derived from pentaerythritol: synthesis and their potent agonistic activity," Tetrahedron 58:8833-8842, 2002.
Jiang et al., "Lipid A Structures Containing Novel Lipid Moieties: Synthesis and Adjuvant Properties," Bioorg Med. Chem. Lett. 12:2193-2196, 2002.
Jiang et al., "Monophosphoryllipid A analogues with varying 3-0-substitution: synthesis and potent adjuvant activity," Carbohydrate Research 342(6): 784-796, 2007.
Johansen et al., "Toll-Like Receptor Ligands as Adjuvants in Allergen-Specific Immunotherapy," Clin. Exp. Allerg 35(12):1591-1598, Dec. 2005.
Johnson, A.G. et al. (1991). "A Comparison of the Immunomodulating Properties of Two Forms of Monophosphoryl Lipid A Analogues," Journal of Immunotherapy 10(6):398-404.
Johnson et al., "Chemical Synthesis of the Major Constituents of Salmonella Minnesota Moniphosphoryl Lipid A," Journal of Carbohydrate Chemistry 17(9):1421-1426, 1998.
Johnson et al., "3-0-Desacyl Monophosphoryl Lipid A Derivatives: Synthesis and Immunostimulant Activities," J Med. Chem. 42(22):4640-4649, 1999.
Johnson et al., "TLR4 Agonists As Vaccine Adjuvants," in M. Singh (ed.), Vaccine Adjuvants and Delivery Systems, John Wiley & Sons, Inc., 2007, pp. 131-156.
Jurgens et al., "Interaction of hemoglobin with enterobacterial lipopolysaccharide and lipid A," Eur. J Biochem. 268:4233-4242, 2001.
Kaisho et al., "Pleiotropic Function of Toll-like Receptors," Microbes Infect. 6(15):1388-1394, Dec. 2004.
Kanegasaki et al., "Biological activities of analogues of lipid A based chemically on the revised structural model," Eur. J Biochem. 143(2):237-242, 1984.
Kanzler et al., "Therapeutic targeting of innate immunity with Toll-like receptor agonists and antagonists," Nature Medicine 13(5): 552-559, May 1, 2007.
Kasai et al., "Immunochemistry of Lipid A," Adv. Exp. Med. Biol. 256: 71-79, 1990.
Kasai et al., "Structure-activity relationships of endotoxic lipid A containing 2,3-diamino-2,3-dideoxy-D-glucose," in Cellular and Molecular Aspects of Endotoxin Reactions: Proceeding of the 1st Congress of the International Endotoxin Society, Elsevier Science Publishers B.V. (Biomedical Division), San Diego, May 9-12, 1990, pp. 121-128.
Kensil et al., "Separation and Characterization of Saponins with Adjuvant Activity from Quillaja Saponaria Molina Cortex," J Immunology 146(2):431-437, Jan. 15, 1991.
Kensil, "Saponins as Vaccine Adjuvants," Crit. Rev. Ther. Drug Carrier Syst. 13(1-2): 1-55, 1996.
Kersten et al., "Liposomes and ISCOMs," Vaccine 21:915-920, 2003.

(56) References Cited

OTHER PUBLICATIONS

Kim et al., "Crystal Structure of the TLR4-MD-2 Complex with Bound Endotoxin Antagonist Eritoran," *Cell* 130:906-917, Sep. 7, 2007.
Kiso et al., "Synthesis of the Optically Active 4-0-Phosphono-D-Glucosamine Derivatives Related to the Nonreducing-Sugar Subunit of Bacterial Lipid A," *Carbohydrate Research* 162:127-140, 1987.
Kolls et al., "Prolonged and Effective Blockade of Tumor Necrosis Factor Activity Through Adenovirus-Mediated Gene Transfer," *Proc. Natl. Acad. Sci. USA* 91:215-219, Jan. 1994.
Kotani, S. et al. (Jul. 1985). "Synthetic Lipid A with Endotoxic and Related Biological Activities Comparable to Those of a Natural Lipid A from an *Escherichia coli* Re-Mutant," *Infection and Immunity* 49(1):225-237.
Kotani et al., "Low Endotoxic Activities of Synthetic Salmonella-Type Lipid A with an Additional Acyloxyacyl Group on the 2-Amino Group of Beta(I-6)Glucosamine Disaccharide 1,4'-Bisphosphate," *Infection and Immunity* 52(3):872-884, Jun. 1986.
Kotani et al., "Structural Requirements of Lipid A. Endotoxicity and Other Biological Activities—An Overview," *Adv. Exp. Med. Biol.* 256:13-43, 1990.
Kriegler et al., "A Novel Form of TNF/Cachectin is a Cell Surface Cytotoxic Transmembrane Protein: Ramifications for the Complex Physiology of TNF," *Cell* 53(1):45-53, Apr. 8, 1988.
Kumazawa et al., "Importance of Fatty Acid Substituents of Chemically Synthesized Lipid A-Subunit Analogs in the Expression of Immunopharmacological Activity," *Infection and Immunity* 56(1):149-155, Jan. 1988.
Kusumoto et al., "Structural basis for endotoxic and antagonistic activities: investigation with novel synthetic lipid A analogs," *Journal of Endotoxin Research* 9(6): 361-366, 2003.
Lacaille-Dubois et al., "A Review of the Biological and Pharmacological Activities of Saponins," *Phytomedicine* 2(4):363-386, 1996.
Lee et al., "Activation of Anti-Hepatitis C Virus Responses Via Toll-Like Receptor 7," *Proc. Nat. Acad. Sci. USA* 103(6):1828-1833, Feb. 7, 2006.
Li et al., "Assessment of Recombinant Adenoviral Vectors for Hepatic Gene Therapy," *Hum. Gene Ther.* 4(4):403-409, Aug. 1993.
Lien et al., "A Novel Synthetic Acyclic Lipid A-like Agonist Activates Cells via the Lipopolysaccharide/Toll-like Receptor 4 Signaling Pathway," *J Biol. Chem.* 276(3):1873-1880, Jan. 19, 2001.
Lien et al., "Adjuvants and Their Signaling Pathways: Beyond TLRs," *Nat. Immunol.* 4(12): 1162-1164, Dec. 2003.
Lin et al., "Implication of Toll-Like Receptor and Tumor Necrosis Factor Alpha Signaling in Septic Shock," *Shock* 24(3):206-209, Sep. 2005.
Liu, "Vaccine Developments," *Nature Medicine* 4(5):515-519, May 1998.
Loppnow et al., "Lipid A, The Immunostimulatory Principle of Lipopolysaccharides?" *Adv. Exp. Med. Biol.* 156:561-566, 1990.
Lu et al., "A Novel Gene (*PLU-1*) Containing Highly Conserved Putative DNA/Chromatin Binding Motifs is Specifically Up-Regulated in Breast Cancer," *J Biol. Chem.* 274(22):15633-15645, May 28, 1999.
Luster, "The Role of Chemokines in Linking Innate and Adaptive Immunity," *Curr. Opin. Immunol.* 14(1):129-135, Feb. 2002.
Maeda et al., "Adjuvant activities of synthetic lipid A subunit analogues and its conjugates with muramyl dipeptide derivatives," *Vaccine* 7(3):275-281, 1989.
Masoud, H. et al. (1991). "Investigation of the Structures of Lipid A from *Actinobacillus actinomycetemcomitans* Strain Y4 and Human Clinical Isolate PO 1021-7," *Eur. J. Biochem.* 200:775-781.
Mata-Haro et al., "The Vaccine Adjuvant Monophosphoryl Lipid A as a TRIP-Biased Agonist of TLR4," *Science* 316:1628-1632, 2007.

McCluskie et al., "CpG DNA is a Potent Enhancer of Systemic and Mucosal Immune Responses Against Hepatitis B Surface Antigen with Intranasal Administration to Mice," *J Immunol.* 161(9):4463-4466, Nov. 1998.
Medzhitov et al., "Innate Immunity: Impact on the Adaptive Immune Response," *Curr. Opin. Immunol.* 9(1):4-9, Feb. 1997.
Medzhitov, "Toll-Like Receptors and Innate Immunity," *Nat. Rev. Immunol.* 1(2):135-145, Nov. 2001.
Melaugh, W. et al. (Jul. 5, 1992). "Partial Characterization of the Major Lipooligosaccharide from a Strain of *Haemophilus ducreyi*, the Causative Agent of Chancroid, a Genital Ulcer Disease," *The Journal of Biological Chemistry* 267(19):13434-13439.
Merck Index Online (SM), CAS Registry No. 11024-24-1, "Digitonin", 2005.
Merck Index Online (SM), CAS Registry No. 111-02-4, "Squalene", 2005.
Merck Index Online (SM), CAS Registry No. 6805-41-0, "Escin", 2005.
Mikhail, I. et al. (2005, e-pub. Mar. 19, 2005). "Structural Characterization of Lipid A from Nontypeable and Type F *Haemophilus influenzae*: Variability of Fatty Acid Substitution," *Analytical Biochemistry* 340:303-316.
Mitchell et al., "Expression of the Pneumolysin Gene in *Escherichia Coli*: Rapid Purification and Biological Properties," *Biochem. Biophys. Acta* 1007:67-72, 1989.
Montminy, S.W. et al. (Oct. 2006, e-pub. Sep. 17, 2006). "Virulence Factors of *Yersinia pestis* are Overcome by a Strong Lipopolysaccharide Response," *Nature Immunology* 7(10):1066-1073.
Mueller et al., "Aggregates Are the Biologically Active Units of Endotoxin," *J Biol. Chem.* 279(25):26307-26313, Jun. 18, 2004.
Nakao et al., "Surface-Expressed TLR6 Participates in the Recognition of Diacylated Lipopeptide and Peptidoglycan in Human Cells," *J Immunol.* 174:1566-1573, 2005.
Nelson et al., "Molecular Cloning and Characterization of Prostase, an Androgen Regulated Serine Protease with Prostate-Restricted Expression," *Proc. Natl. Acad. Sci. USA* 96(6):3114-3119, Mar. 16, 1999.
Notice of Allowance dated Jul. 1, 2016, for U.S. Appl. No. 14/222,481, filed Mar. 21, 2014, 7 pages.
PCT Application No. PCT/US2007/021017, International Filing Date Sep. 26, 2007, International Search Report and Written Opinion dated Oct. 17, 2008.
PCT Application No. PCT/US2009/045033, International Filing Date May 22, 2009, International Search Report and Written Opinion dated Mar. 9, 2010.
PCT Application No. PCT/US2010/37466, International Filing Date Jun. 4, 2010, International Search Report and Written Opinion dated Aug. 25, 2010.
Persing, D.H. (2002). "Taking Toll: Lipid A Mimetics as Adjuvants and Immunomodulators," *Trends in Microbiology* 10(10):S32-S37.
PHAD™ advertisement in J. Biol. Chem. (Mar. 2, 2007), 282(9), 2 pages.
Qureshi et al. "Purification and Structural Determination of Nontoxic Lipid A Obtained from the Lipopolysaccharide of *Salmonella* Typhimurium," *Journal of Biological Chemistry* 257(19):11808-11815, Oct. 10, 1982.
Qureshi et al., "Position of Ester Groups in the Lipid A Backbone of Lipopolysaccharides Obtained from *Salmonella* typhimurium," *Journal of Biological Chemistry* 258(21):12947-12951, Nov. 10, 1983.
Qureshi et al., "Monophosphoryl Lipid A Obtained from Lipopolysaccharides of *Salmonella minnesota* R595," *J Biol. Chem.* 260(9):5271-5278, May 10, 1985.
Qureshi, N. et al. (Aug. 25, 1988). "Complete Structural Determination of Lipopolysaccharide Obtained from Deep Rough Mutant of *Escherichia coli*," *The Journal of Biological Chemistry* 263(24):11971-11976.
Raetz, C.R.H. et al. (2006). "Kdo$_2$-Lipid A of *Escherichia coli*, a Defined Endotoxin that Activates Macrophages Via TLR-4," *Journal of Lipid Research* 47:1097:1111.
Reed et al., "An Improved Serodiagnostic Procedure for Visceral Leishmaniasis," *Am. J Trap. Med. Hyg.* 43(6):632-639, Dec. 1990.

(56) References Cited

OTHER PUBLICATIONS

Reed et al., "New horizons in adjuvants for vaccine development," *Trends in Immunology* 30(1):23-32, Jan. 1, 2009.
Reed et al., "Vaccine Composition Containing Synthetic Adjuvant," U.S. Appl. No. 12/154,663, filed May 22, 2008.
Reed et al., "Vaccine Composition Containing Synthetic Adjuvant," U.S. Appl. No. 12/134,127, filed Jun. 5, 2008.
Reiter et al., "Prostate Stem Cell Antigen: A Cell Surface Marker Overexpressed in Prostate Cancer," *Proc. Nat. Acad. Sci. USA* 95(4):1735-1740, Feb. 17, 1998.
Ribi, E. (1984). "Beneficial Modification of the Endotoxin Molecule," *Journal of Biological Response Modifiers* 3(1):1-9.
Richards, R.L. et al. (Dec. 1989). "Immunogenicity of Liposomal Malaria Sporozoite Antigen in Monkeys: Adjuvant Effects of Aluminium Hydroxide and Non-Pyrogenic Liposomal Lipid A," *Vaccine* 7:506-512.
Rietschel et al., "Endotoxic properties of synthetic pentaacyllipid A precursor 1 b and a structural isomer," *Eur. J Biochem.* 169:27-31, 1987.
Rietschel, E.T. et al. (1987). "Lipid A, the Endotoxic Center of Bacterial Lipopoly-Saccharides: Relation of Chemical Structure to Biological Activity," *Progr. Clin. Biol. Res.* 231:25-53.
Rietschel et al., "The Chemical Structure of Bacterial Endotoxin in Relation to Bioactivity," *Immunobiology* 187: 169-190, 1993.
Rietschel, E.T. et al. (Feb. 1994). "Bacterial Endotoxin: Molecular Relationships of Structure to Activity and Function," *The FASEB Journal* 8:217-225.
Robbins et al., "Human Tumor Antigens Recognized by T-Cells," *Curr. Opin. Immunol.* 8(5):628-636, Oct. 1996.
Rubins et al., "Pneumolysin in Pneumococcal Adherence and Colonization," *Microb. Pathog.* 25(6):337-342, Dec. 1998.
Salem et al., "The Adjuvant Effects of the Toll-Like Receptor 3 Ligand Polyinosinic-Cytidylic Acid Poly (I:C) on Antigen-Specific CD8+ T Cell Responses are Partially Dependent on NK Cells with the Induction of a Beneficial Cytokine Milieu," *Vaccine* 24(24):5119-5132, Jun. 12, 2006.
Salomon et al., "Cripto: A Novel Epidermal Growth Factor (EGF)-Related Peptide in Mammary Gland Development and Neoplasia," *BioEssays* 21(1):61-70, Jan. 1999.
Schirmbeck et al. "Antigenic Epitopes Fused to Cationic Peptide Bound to Oligonucleotides Facilitate Toll-Like Receptor 9-Dependent, but CD4+T Cell Help-Independent Priming of CD8+T Cells," *J. Immunol.* 171(10):5198-5207, Nov. 15, 2003.
Schmidt et al., "Cytokine and Ig-Production by CO-Containing Sequences with Phosphorodiester Backbone and Dumbbell Shape," *Allergy* 61(1):56-63, Jan. 2006.
Schnur et al., "Leishmania! Serotypes as Distinguished by the Gel Diffusion of Factors Excreted in Vitro and in Vivo," *Isrl. J Med. Sci.* 8(7):932-942, Jul. 1972.
Schromm et al., "Biological activities of lipopolysaccharides are determined by the shape of their lipid A portion," *Eur. J Biochem.* 267:2008-2013, 2000.
Senaldi et al., "Serological Diagnosis of Visceral Leishmaniasis by a Dot-Enzyme Immunoassay for the Detection of a Leishmania Donovani-Related Circulating Antigen," *J Immunol. Methods* 193(1):9-15, Jun. 1996.
Seong et al. "Serological Diagnosis of Visceral Leishmaniasis by a Dot-Enzyme Immunoassay for the Detection of a Leishmania Donovani-Related Circulating Antigen," *J. Immunol. Methods* 193(1):9-15, Jun. 1996.
Sethi et al., "Bacterial Infection in Chronic Obstructive Pulmonary Disease in 2000: A State-of-the-Art Review," *Clin Microbial Rev.* 14(2):336-63, Apr. 2001.
Seydel et al., "Supramolecular structure of lipopolysaccharide and free lipid A under physiological conditions as determined by synchrotron small-angel X-ray diffraction," *Eur. J Biochem.* 186:325-332, 1989.
Seydel et al., "Intrinsic conformation of lipid A is responsible for agonistic and antagonistic activity," *Eur. J Biochem.* 267:3032-3039, 2000.
Seydel et al., "Physicochemical characterization of carboxymethyl lipid A derivatives in relation to biological activity," *FEES J* 272:327-340, 2005.
Smith et al, "The Active Form of Tumor Necrosis Factor is a Trimer," *J Biol. Chem.* 262(15):6951-6954, May 25, 1987.
Soboll et al., "Expression of Toll-Like Receptors (TLR) and Responsiveness to TLR Agonists by Polarized Mouse Uterine Epithelial Cells in Culture," *Biol. Reprod.* 75(1):131-139, Jul. 2006.
Takada et al., "Immunopharmacological Activities of a Synthetic Counterpart of a Biosynthetic Lipid A Precursor Molecule and of Its Analogs," *Infection and Immunity* 48(1):219-227, Apr. 1985.
Takada, H. et al. (1989). "Structural Requirements of Lipid A for Endotoxicity and Other Biological Activities," *CRC Critical Reviews in Microbiology* 16(6): 477-523.
Takayama et al., "Complete Structure of Lipid A Obtained from the Lipopolysaccharides of the Heptoseless Mutant of *Salmonella typhimurium,*" *J Biol. Chem.* 258(21):12801-12803, Nov. 10, 1983.
Takeda et al., "Toll-Like Receptors," *Ann. Rev. Immunol.* 21:335-376, 2003.
Takeda et al., "Toll-Like Receptors in Innate Immunity," *Int. Immunol.* 17(1):1-14, Jan. 2005.
Tamai et al., "Cell activation by monosaccharide lipid A analogues utilizing Toll-like receptor 4," *Immunology* 110: 66-72, 2003.
Teghanemt et al., "Molecular Basis of Reduced Potency of Underacylated Endotoxins," *J. Immun.* 175:4669-4676, 2005.
Thérisod, H. et al. (2001, e-pub. May 22, 2001). "Helicobacter mustelae Lipid A Structure Differs from that of *Helicobacter pylori,*" *FEBS Letters* 499:1-5.
Thompson et al., "The low-toxicity versions of LPS, MPL ®adjuvant and RC529, are efficient adjuvants for CD4+ T cells," *J Leukoc. Biol.* 78:1273-1280, 2005.
Triantafilou et al., "Combinational clustering of receptors following stimulation by bacterial products determines lipopolysaccharide responses," *Biochem. J* 381:527-536, 2004.
Triozzi et al., "Effects of a Beta-Human Chorionic Gonadotropin Subunit Immunogen Administered in Aqueous Solution with a Novel Nonionic Block Copolymer Adjuvant in Patients with Advanced Cancer," *Clin. Cancer Res.* 3(12 Pt 1):2355-2362, Dec. 1997.
Tsan et al., "Cytokine Function of Heat Shock Proteins," *Am. J Physiol. Cell Physiol.* 286(4):C739-C744, Apr. 2004.
Tsan et al., "Endogenous Ligands of Toll-Like Receptors," *J Leukoc. Biol.* 76(3):514-519, Sep. 2, 2004.
U.S. Appl. No. 11/862,122, filed Sep. 26, 2007, Final Office Action dated Feb. 1, 2010.
U.S. Appl. No. 11/862,122, filed Sep. 26, 2007, Office Action dated Jul. 28, 2009.
U.S. Appl. No. 12/351,710, filed Jan. 9, 2009, Office Action dated Dec. 13, 2010.
U.S. Appl. No. 14/222,481, filed Mar. 21, 2014, Office Action dated Mar. 9, 2016, 12 pages.
Ulrich et al., Topics in Vaccine Adjuvant Research, Jan. 1, 1991, Chapter 12, "The Adjuvant Activity of Monophosphoryl Lipid A," pp. 133-143.
Ulrich et al., Vaccine Design: The Subunit and Adjuvant Approach, Plenum Press, New York, Jan. 1, 1995, Chapter 21, "Monophosphoryl Lipid A as an Adjuvant," pp. 495-524.
Van den Eynde et al., "Tumor Antigens Recognized by T-lymphocytes," *Int. J Clin. Lab. Res.* 27:81-86, 1997.
Vincent et al., "Long-term Correction of Mouse Dystrophic Degeneration by Adenovirusmediated TransferofaMinidystrophinGene," *Nat. Genet.* 5(2):130-134, Oct. 1993.
Vollmer et al. "Immunopharmacology of CpG Oligodeoxynucleotides and Ribavirin," *Antimicrob. Agents Chemother.* 48(6):2314-2317, Jun. 2004.
Vollmer, "Progress in drug development of Immunostimulatory CpG oligodeoxynucleotide ligands for TLR9," *Exp. Opin. Biolog. Ther.* 5(5):673-682, May 2005.
Wang et al. "pH-sensitive Immunoliposomes Mediate Target-Cell-Specific Delivery and Controlled Expression of a Foreign Gene in Mouse," *Proc. Natl. Acad. Sci. USA* 84:7851-7855, Nov. 1987.
Wasylyk et al., "The Ets Family of Transcription Factors," *Eur. J Bioch.* 211(1-2):7-18, Jan. 15, 1993.

(56) References Cited

OTHER PUBLICATIONS

Weeratna et al., "TLR Agonists as Vaccine Adjuvants: Comparison of CpG ODN and Resiquimod (R-848)," *Vaccine* 23(45):5263-5270, Nov. 2005.

Weihrauch et al., "Phase I/II Combined Chemoimmunotherapy with Carcinoembryonic Antigen-Derived HLA-A2-Restricted CAP-I Peptide and Irinotecan, 5-Fluorouracil, and Leucovorin in Patients with Primary Metastatic Colorectal Cancer," *Clin. Cancer Res.* 11(16):5993-6001, Aug. 15, 2005.

Wheeler et al., "Allergy vaccines—new approaches to an old concept," *Expert Opinion on Biological Therapy* 4(9): 1473-1481, Sep. 2004.

Wu et al., "Targeting Genes: Delivery and Persistent Expression of a Foreign Gene Driven by Mammalian Regulatory Elements in Vivo," *J Biol. Chem.* 264(29):16985-16987, Oct. 15, 1989.

Xiong et al., "Inhibition of Interleukin-12 p40 Transcription and NF-κb Activation by Nitric Oxide in Murine Macrophages and Dendritic Cells," *J Biol. Chem.* 279(11):10776-10783, Mar. 12, 2004.

Yang et al., "The immunogenicity-enhancing effect of emulsion vaccine adjuvants is independent of the dispersion type and antigen release rate-a revisit of the role of the hydrophile-lipophile balance (HLB) value," *Vaccine* 23:2665-2675, 2005.

Yasuda et al., "Biological Activity of Chemically Synthesized Analogues of Lipid A," *European Journal of Biochemistry* 124(2): 405-407, May 17, 1982.

Yasuda et al., "Further study of biological activities of chemically synthesized analogues of lipid A in artificial membrane vesicles," *Eur. J Biochem.* 140(2):245-248, 1984.

Yeh et al., "Improving Protein Delivery from Microparticles Using Blends of Poly(DL Lactide Co-Glycolide) and Poly(Ethylene Oxide)-Poly(Propylene Oxide) Copolymers," *Pharm. Res.* 13(11):1693-1698, Nov. 1996.

Yoshikawa M, et al., "Bioactive Saponins and Glycosides. III. Horse Chestnut. (1): The Structures, Inhibitory Effects on Ethanol Absorption, and Hypoglycemic Activity of Escins Ia, Ib,IIa,IIb, and IIIa from the Seeds of *Aesculus hippocastanum L.*," *Chem. Pharm. Bull.* 44(8):1454-1464, Aug. 1996.

Yoshiyuki, F. et al. (2008). "Synthesis of *Rubrivivax gelatinosus* Lipid A and Analogues for Investigation of the Structural Basis for Immunostimulating and Inhibitory Activities," *Bull. Chem. Soc. Jpn.*, 81(7):796-819.

Zähringer, U. et al. (1994). "Molecular Structure of Lipid A, the Endotoxic Center of Bacterial Lipopolysaccharides," *Advances in Carbohydrate Chemistry and Biochemistry* 50:211-276.

Zhang, Y. et al. (Apr. 25, 2007). "Modulation of Innate Immune Responses with Synthetic Lipid A Derivatives," *Journal of American Chemical Society* 129(16):5200-5216.

Zhang, Y. et al. (2008). "Innate Immune Responses of Synthetic Lipid A Derivatives of Neisseria Meningitidis," *Chem. Eur. J.* 14(2):558-569.

Zijlstra et al., "The Direct Agglutination Test for Diagnosis of Visceral Leishmaniasis Under Field Conditions in Sudan: Comparison of Aqueous and Freeze-Dried Antigens," *Trans. R. Soc. Trop. Med. Hyg* 91(6):671-673, Nov.-Dec. 1997.

Notice of Opposition Against European U.S. Pat. No. 2 068 918 B1 (European Application No. 07875082.5), Vaccine Composition Containing Synthetic Adjuvant, dated Feb. 1, 2013, 41 pages.

\* cited by examiner

SYNTHETIC GLUCOPYRANOSYL LIPID ADJUVANTS

CROSS-REFERENCE TO RELATED APPLICATIONS

This application is a continuation application of U.S. patent application Ser. No. 15/285,378, filed Oct. 4, 2016, which is a continuation of U.S. patent application Ser. No. 14/222,481, filed Mar. 21, 2014, now U.S. Pat. No. 9,480,740, which is a continuation application of U.S. patent application Ser. No. 12/794,336, filed Jun. 4, 2010, now U.S. Pat. No. 8,722,064, which claims the benefit under 35 U.S.C. § 119(e) of U.S. Provisional Patent Application Ser. No. 61/184,703 filed Jun. 5, 2009, the contents of which are incorporated herein by reference in their entirety.

BACKGROUND OF THE INVENTION

Field of the Invention

The present invention relates to the field of pharmaceutical and vaccine compositions. More specifically, embodiments described herein relate to pharmaceutical and vaccine compositions, as well as related prophylactic and therapeutic methods, wherein the compositions comprise a glucopyranosyl lipid adjuvant (GLA) as described herein.

Description of the Related Art

The immune system of higher organisms has been characterized as distinguishing foreign agents (or "non-self") agents from familiar or "self" components, such that foreign agents elicit immune responses while "self" components are ignored or tolerated. Immune responses have traditionally been characterized as either humoral responses, in which antibodies specific for antigens are produced by differentiated B lymphocytes known as plasma cells, or cell mediated responses, in which various types of T lymphocytes act to eliminate antigens by a number of mechanisms. For example, CD4+ helper T cells that are capable of recognizing specific antigens may respond by releasing soluble mediators such as cytokines to recruit additional cells of the immune system to participate in an immune response. Also, CD8+ cytotoxic T cells that are also capable of specific antigen recognition may respond by binding to and destroying or damaging an antigen-bearing cell or particle. It is known in the immunological arts to provide certain vaccines according to a variety of formulations, usually for the purpose of inducing a desired immune response in a host.

Several strategies for eliciting specific immune responses through the administration of a vaccine to a host include immunization with heat-killed or with live, attenuated infectious pathogens such as viruses, bacteria or certain eukaryotic pathogens; immunization with a non-virulent infective agent capable of directing the expression of genetic material encoding the antigen(s) to which an immune response is desired; and immunization with subunit vaccines that contain isolated immunogens (such as proteins) from a particular pathogen in order to induce immunity against the pathogen. (See, e.g., Liu, 1998 Nature Medicine 4(5 suppl.):515.) For certain antigens there may be one or more types of desirable immunity for which none of these approaches has been particularly effective, including the development of vaccines that are effective in protecting a host immunologically against human immunodeficiency viruses or other infectious pathogens, cancer, autoimmune disease, or other clinical conditions.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of Bacterial Endotoxins, Plenum Publ. Corp., NY, p 407-419).

A further detoxified version of MPL results from the removal of the acyl chain from the 3-position of the disaccharide backbone, and is called 3-O-deacylated monophosphoryl lipid A (3D-MPL). It can be purified and prepared by the methods taught in GB 2122204B, which reference also discloses the preparation of diphosphoryl lipid A, and 3-O-deacylated variants thereof. For example, 3D-MPL has been prepared in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

Bacterial lipopolysaccharide-derived adjuvants to be formulated in adjuvant combinations may be purified and processed from bacterial sources, or alternatively they may be synthetic. For example, purified monophosphoryl lipid A is described in Ribi et at 1986 (supra), and 3-O-deacylated monophosphoryl or diphosphoryl lipid A derived from *Salmonella* sp. is described in GB 2220211 and U.S. Pat. No. 4,912,094. 3D-MPL and the β(1-6) glucosamine disaccharides as well as other purified and synthetic lipopolysaccharides have been described (WO 98/01139; U.S. Pat. No. 6,005,099 and EP 0 729 473 B1, Hilgers et al., 1986 *Int. Arch. Allergy Immunol.*, 79(4):392-6; Hilgers et at., 1987, *Immunology*, 60(1); 141-6; and EP 0 549 074 B1). Combinations of 3D-MPL and saponin adjuvants derived from the bark of *Quillaja Saponaria molina* have been described in EP 0 761 231B. WO 95/17210 discloses an adjuvant emulsion system based on squalene, α-tocopherol, and polyoxyethylene sorbitan monooleate (TWEEN™-80), formulated with the immunostimulant QS21, and optionally including 3D-MPL. Despite the accessibility of such combinations, the use of adjuvants derived from natural products is accompanied by high production costs, inconsistency from lot to lot, difficulties associated with large-scale production, and uncertainty with respect to the presence of impurities in the compositional make-up of any given preparation.

Accordingly, there is a need for improved vaccines, and in particular for vaccines that beneficially contain high-purity, chemically defined adjuvant components that exhibit lot-to-lot consistency and that can be manufactured efficiently on an industrial scale without introducing unwanted or structurally undefined contaminants. The present invention provides compositions and methods for such vaccines, and offers other related advantages.

BRIEF SUMMARY OF THE INVENTION

The present invention in its several aspects is directed to compounds, compositions and methods that advantageously employ certain synthetic glucopyranosyl lipid adjuvants (GLA) as immunomodulators or adjuvants. Therefore, according to one aspect of the invention described herein, there are provided GLA compounds having a structure according to the following formula (I):

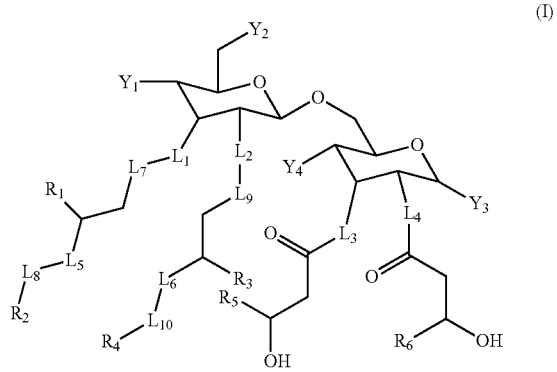

(I)

or a pharmaceutically acceptable salt thereof, wherein $L_1$, $L_2$, $L_3$, $L_4$, $L_5$, $L_6$, $L_7$, $L_8$, $L_9$, $L_{10}$, $Y_1$, $Y_2$, $Y_3$, $Y_4$, $R_1$, $R_2$, $R_3$, $R_4$, $R_5$, $R_6$, are as defined herein.

The GLA compounds of the present invention have utility over a broad range of therapeutic applications where induction of specific or non-specific immune responses is desired. For example, in certain aspects of the invention, there are provided vaccine compositions comprising one or more GLA compounds as set forth herein in combination with an antigen. Such vaccine compositions may be advantageously used in methods for stimulating antigen-specific immune responses in subjects in need thereof. In other aspects of the invention, there are provided pharmaceutical compositions comprising one or more GLA compounds as set forth herein, wherein the compositions are substantially devoid of antigen. Such pharmaceutical compositions may be advantageously used in methods for stimulating non-specific immune responses in subjects in need thereof, for example in the treatment of infection, seasonal rhinitis and the like.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE SEVERAL VIEWS OF THE DRAWING(S)

FIG. 1 demonstrates IFN-γ cytokine production induced in vivo following vaccination of mice with compositions of the invention comprising antigen and GLA.

DETAILED DESCRIPTION OF THE INVENTION

Figure 1:
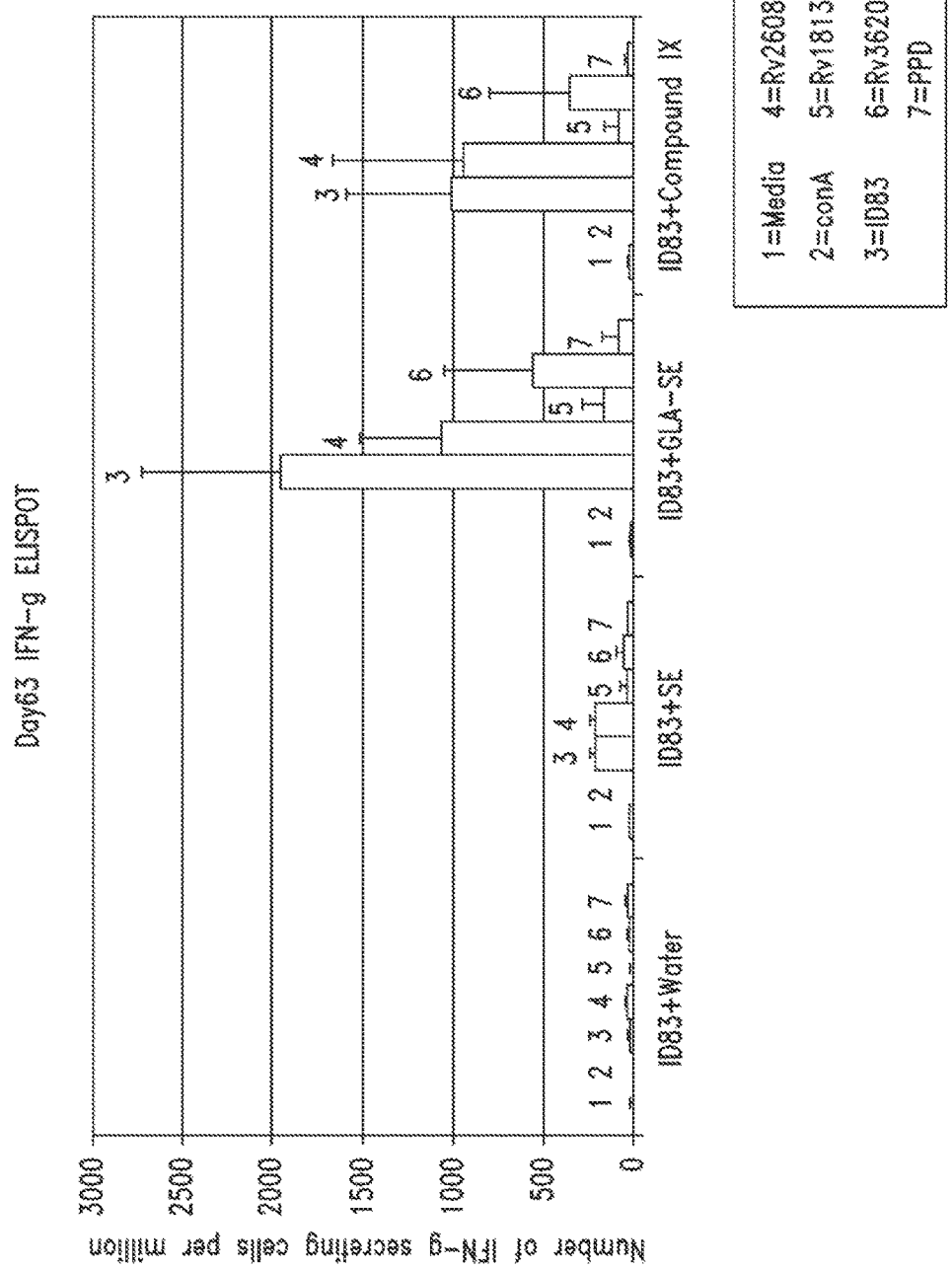
Figure 2A:
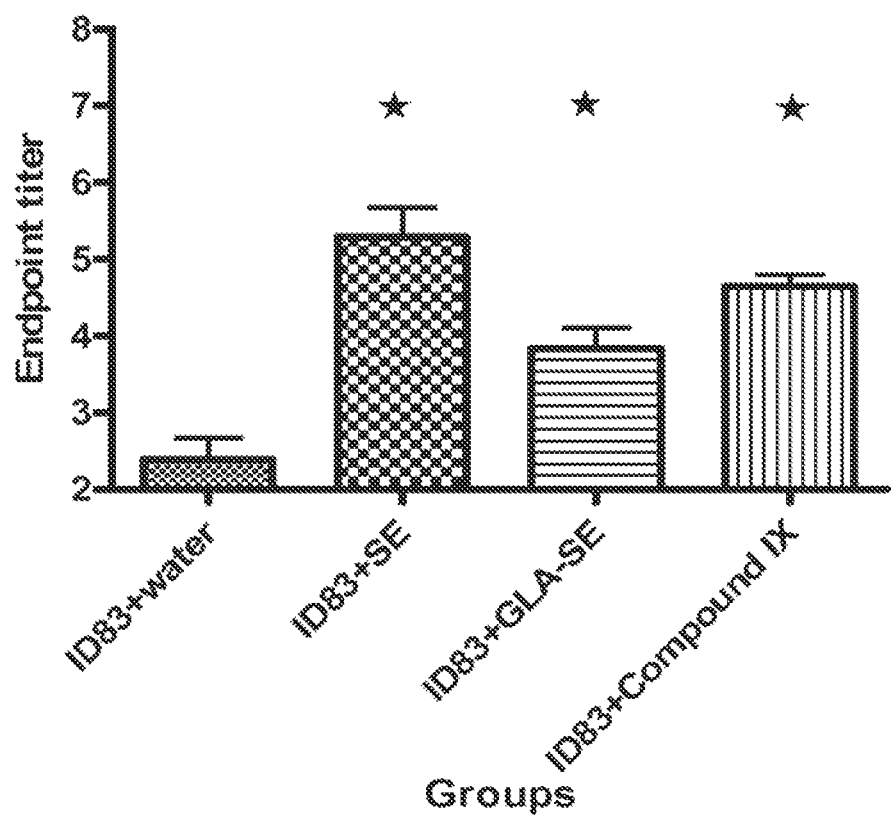
FIGS. 2A-2F show antibody responses induced in vivo following vaccination of mice with compositions of the invention comprising antigen and GLA.
Figure 2B:
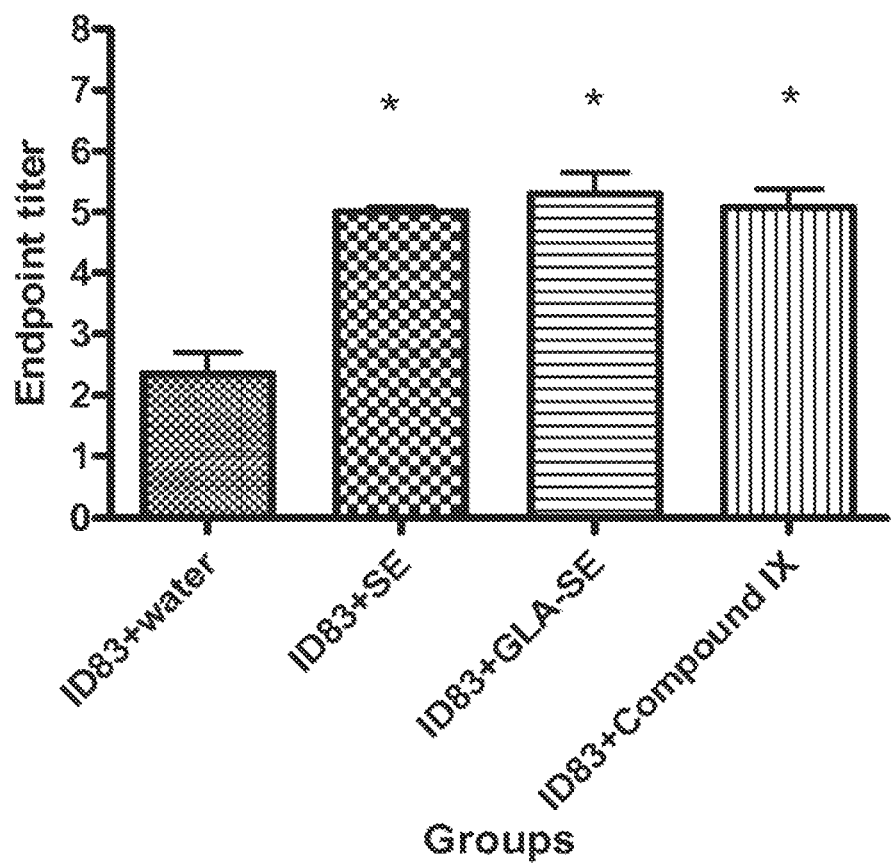
Figure 2C:
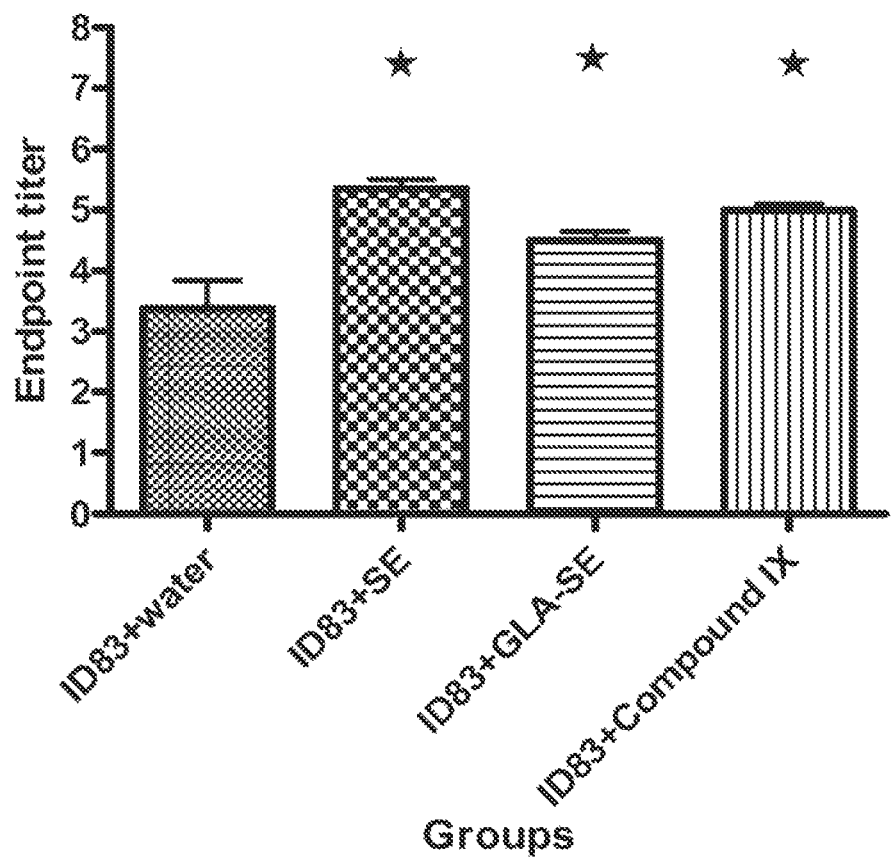
Figure 2D:
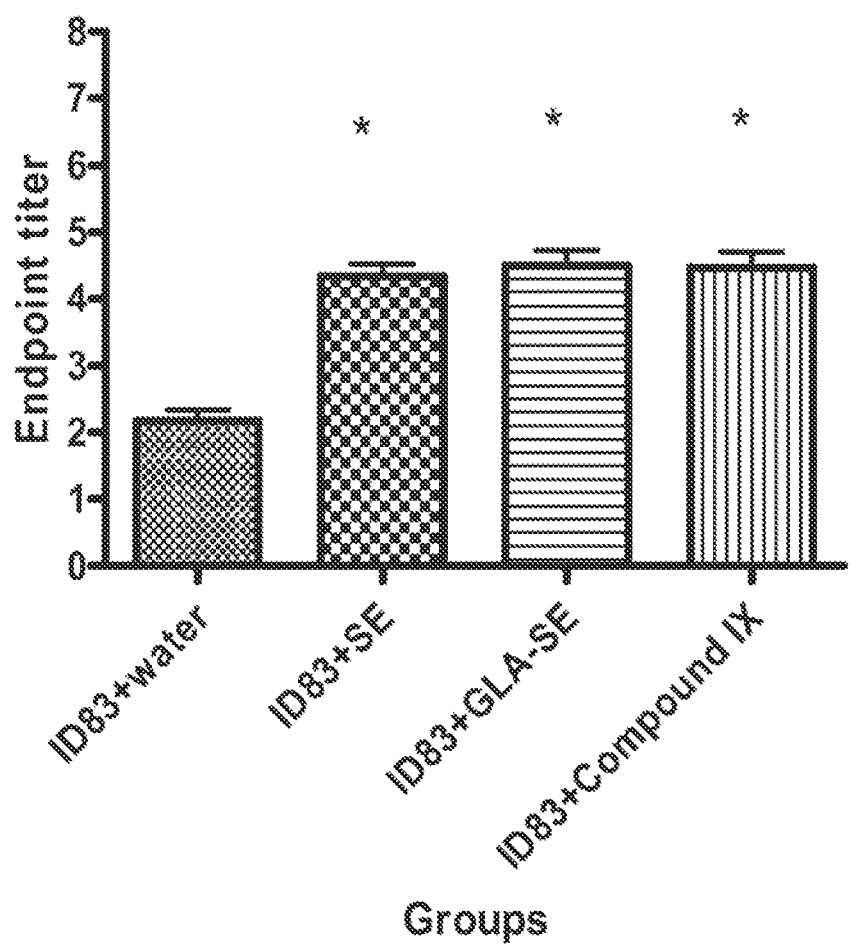
Figure 2E:
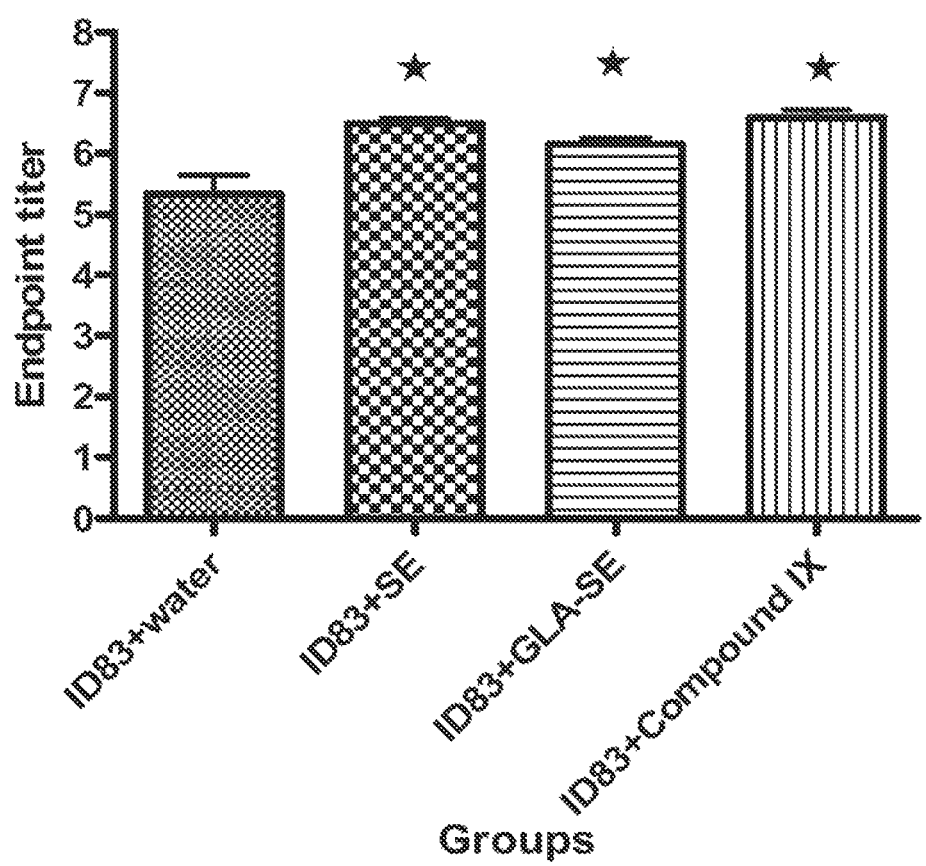
Figure 2F:
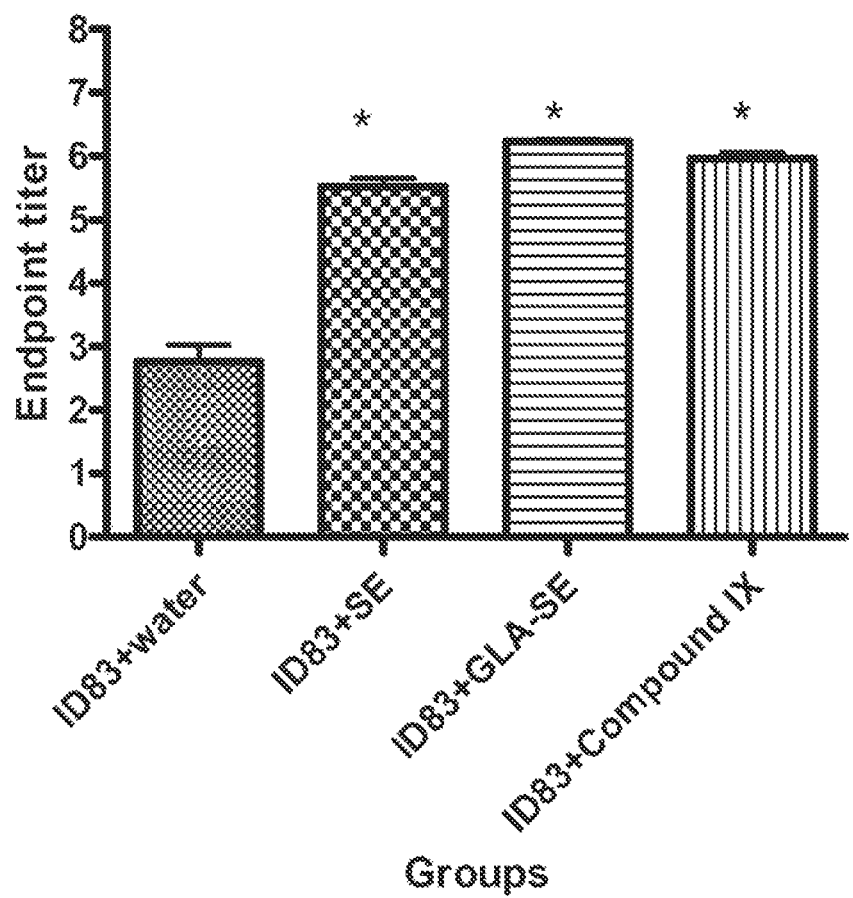

Monophosphoryl lipid A (MPL) and other related adjuvants are known to mediate their effects, at least in part, by acting as agonists of Toll-like receptors (TLR). The glucopyranosyl lipid adjuvant (GLA) compounds of the present invention were rationally designed based upon 3D structural considerations in relation to TLR receptor stimulation. More specifically, according to the present invention, by selectively defining the acyl chain lengths of the GLA compounds of the invention such that they achieve a "flat" bottom in the three dimensional structure of the compounds, an improved fit may be achieved within the binding site of a TLR receptor, thereby resulting in enhanced TLR stimulation and enhanced immunostimulatory properties. In addition, the solubility of the GLA compounds of the invention (e.g., in aqueous solutions) is advantageously improved due to the shortened acyl chain lengths, thereby facilitating efficient and effective compound formulation. Furthermore, because the acyl chain lengths are tailored to make the molecule three dimensionally "flat" along the bottom of the molecule, the compounds can be more effectively incorporated within vesicles, e.g., for liposomal formulations.

Further still, compounds of the invention provide advantageous profiles of potency relative to toxicity. For example, the compounds of the invention may be used over a broad and relatively high range of dosages for achieving a desired level of activity (e.g., adjuvant activity), while nevertheless remaining substantially non-toxic to human cells and to human patients, as assayed, for example, by the levels of tumor necrosis factor produced from human cells over a range of concentrations, which quickly rises and levels off unlike other more toxic TLR4 agonists such as lipopolysaccharide. This cell based assay should be predictive of lower inflammatory markers like C-reactive protein involved in adverse events in human pharmacology. The favorable potency vs. toxicity profile for the compounds of the invention may be particularly important, for example, when administering to children whose tolerance to cytokines may be lower, or when the compounds are used in formulations targeted at a large population where more leveled responses will translate into more consistent clinical outcomes for people with a varied responsiveness to TLR agonism. Similarly, regulatory approval will be simplified since target dosing will be more forgiving and manufacturing simplified when the range of active pharmaceutical ingredient need not be controlled at as strict a tolerance level.

Therefore, the present invention in its many embodiments provides compounds, vaccine compositions, adjuvant compositions, pharmaceutical compositions and related formulations and methods that include synthetic GLA compounds as described herein. The GLA compounds represent synthetic immunomodulators which, advantageously relative to adjuvants of the prior art, and in particular, relative to natural product adjuvants, can be prepared in substantially homogeneous form. Moreover, the GLA compounds of the invention can be prepared efficiently and economically through large-scale synthetic chemical manufacturing, unlike natural product-derived adjuvants. Because a synthetic adjuvant that is chemically synthesized from defined starting materials to obtain a chemically defined product exhibits qualitative and quantitative batch-to-batch consistency, the GLA compounds of the invention offer benefits including improved product quality control.

As described herein, GLA compounds, compositions and methods for their use include in some embodiments the use of GLA by itself with a pharmaceutically acceptable carrier or excipient for immunological adjuvant activity (e.g., non-specific immunostimulatory activity), including "adjuvanting" in which GLA administration to a subject may be wholly independent of, and/or separated temporally and/or spatially from, administration to the subject of one or more antigens against which elicitation or enhancement of an immune response (e.g., an antigen-specific response) in the subject is desired. Other embodiments include the use of GLA in a vaccine composition that also includes one or a plurality of antigens to which an immune response elicited or enhanced by such a vaccine is desired.

As described herein, these vaccine compositions may in certain related embodiments also include one or more toll-like receptor (TLR) agonist and/or one or a plurality of one or more of a co-adjuvant, an imidazoquinoline immune response modifier, and a double stem loop immune modifier (dSLIM). In other related embodiments, a vaccine composition as provided herein may comprise GLA and one or more recombinant expression constructs each comprising a promoter operably linked to a nucleic acid sequence encoding the antigen against which elicitation or enhancement of an immune response (e.g., an antigen-specific response) in the subject is desired.

GLA

As noted above, because GLA is a chemically synthesized adjuvant it can be prepared in substantially homogeneous form, which refers to a GLA preparation that is at least 80%, preferably at least 85%, more preferably at least 90%, more preferably at least 95% and still more preferably at least 96%, 97%, 98% or 99% pure with respect to the GLA molecule.

GLA compounds of the present invention have the following formula (I):

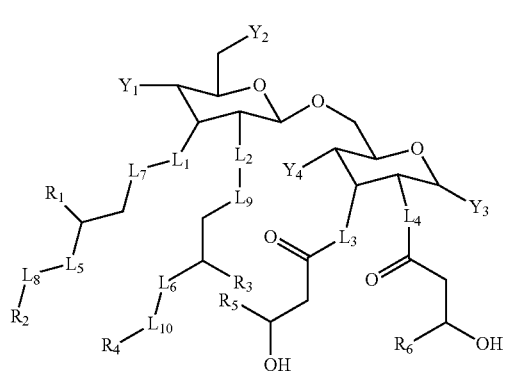

or a pharmaceutically acceptable salt thereof, wherein:

$L_1$, $L_2$, $L_3$, $L_4$, $L_5$ and $L_6$ are the same or different and independently —O—, —NH— or —($CH_2$)—;

$L_7$, $L_8$, $L_9$, and $L_{10}$ are the same or different and independently absent or —C(=O)—;

$Y_1$ is an acid functional group;

$Y_2$ and $Y_3$ are the same or different and independently —OH, —SH, or an acid functional group;

$Y_4$ is —OH or —SH;

$R_1$, $R_3$, $R_5$ and $R_6$ are the same or different and independently $C_{8-13}$ alkyl; and $R_2$ and $R_4$ are the same or different and independently $C_{6-11}$ allyl.

As used herein, the above terms have the following meaning:

"Alkyl" means a straight chain or branched, noncyclic or cyclic, unsaturated or saturated aliphatic hydrocarbon containing from 1 to 20 carbon atoms, and in certain preferred embodiments containing from 11 to 20 carbon atoms. Representative saturated straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

"$C_{8-13}$ alkyl" and "$C_{6-11}$ alkyl" mean an alkyl as defined above, containing from 8-13 or 6-11 carbon atoms, respectively.

"Acid functional group" means a functional group capable of donating a proton in aqueous media (i.e. a Bronsied-Lowry acid). After donating a proton, the acid functional group becomes a negatively charged species (i.e. the conjugate base of the acid functional group). Examples of acid functional groups include, but are not limited to: —OP(=O)(OH)$_2$ (phosphate), —OS(=O)(OH)$_2$ (sulfate), —OS(OH)$_2$ (sulfite), —C(=O)OH (carboxylate), —OC(=O)CH(NH$_2$)CH$_2$C(=O)OH (aspartate), —OC(=O)CH$_2$CH$_2$C(=O)OH (succinate), and —OC(=O)CH$_2$OP(=O)(OH)$_2$ (carboxymethylphosphate).

In more specific embodiments, the present invention provides GLA compounds of formula (I), wherein $L_5$ and $L_6$ are both —O— and $L_7$, $L_8$, $L_9$, and $L_{10}$ are each —C(=O)—, and the GLA compounds have the following formula (II):

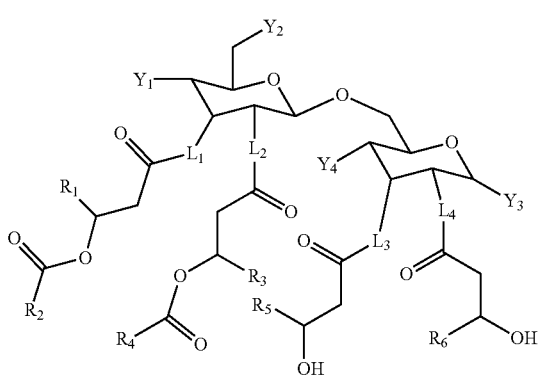

In more specific embodiments, the present invention provides GLA compounds of formula (II), wherein $R_1$, $R_3$, $R_5$ and $R_6$ are each $C_x$ alkyl, where x is constant and is selected from an integer from 8-13, and $R_2$ and $R_4$ are both $C_{x-2}$ alkyl, and the GLA compounds have the following formula (III):

(III)

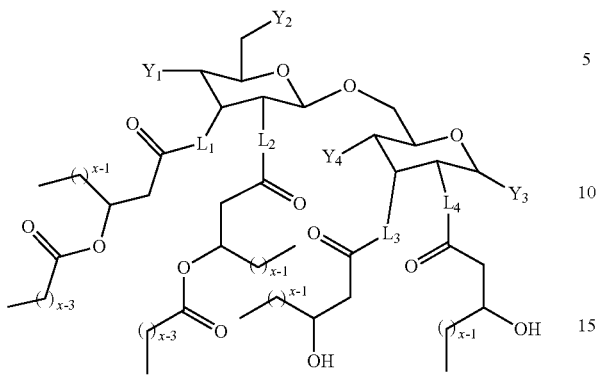

In other more specific embodiments, the present invention provides GLA compounds of formula (III), wherein x is selected from an integer from 10-12.

In other more specific embodiments, the present invention provides GLA compounds of formula (III), wherein x is 11, and the GLA compounds have the following structure (IV):

(IV)

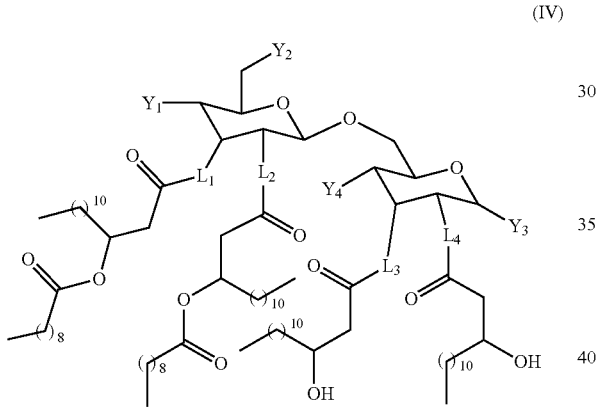

In still other specific embodiments, the invention provides GLA compounds of formula (II), wherein $Y_1$ is —OP(═O)(OH)$_2$ and $Y_2$, $Y_3$ and $Y_4$ are each —OH, and the GLA compounds have the following formula (V):

(V)

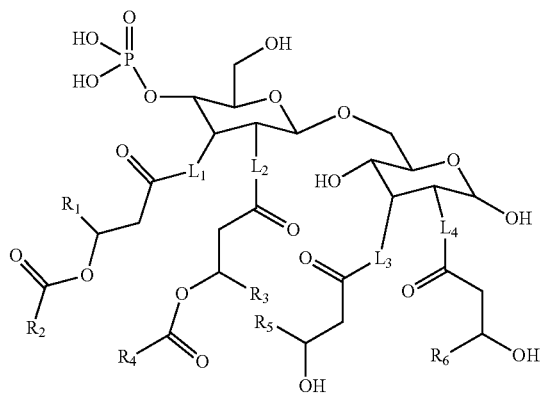

In other specific embodiments, the invention provides GLA compounds of formula (II), wherein $L_1$ and $L_3$ are both —O— and $L_2$ and $L_4$ are both —NH—, and the GLA compounds have the following formula (VI):

(VI)

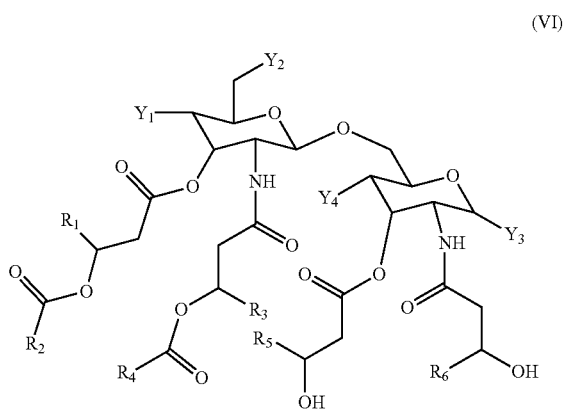

In yet more specific embodiments, the invention provides GLA compounds of formula (II), wherein $Y_1$ is —OP(O)(OH)$_2$, $Y_2$, $Y_3$ and $Y_4$ are each —OH, $L_1$ and $L_3$ are both —O—, and $L_2$ and $L_4$ are both —NH—, and the GLA compounds have the following formula (VII):

(VII)

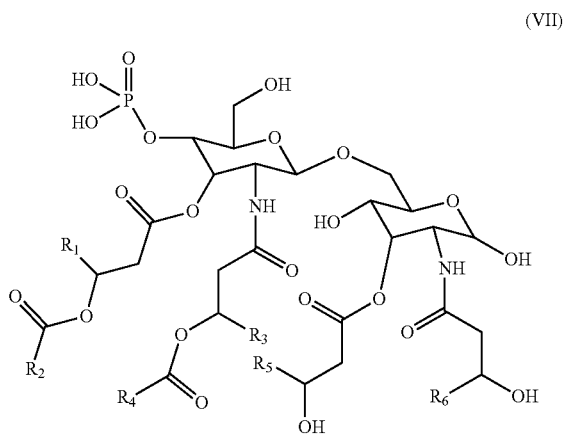

In still other specific embodiments, the present invention provides GLA compounds of formula (II), wherein Y1 is —OP(O)(OH)$_2$, $Y_2$, $Y_3$ and $Y_4$ are each —OH, $L_1$ and $L_3$ are both —O—, $L_2$ and $L_4$ are both —NH—, $R_1$, $R_3$, $R_5$ and $R_6$ each are $C_x$ alkyl where x is constant and is selected from an integer from 8-13, and $R_2$ and $R_4$ are both $C_{x-2}$ alkyl, and the GLA compounds have the following formula (VIII):

(VIII)

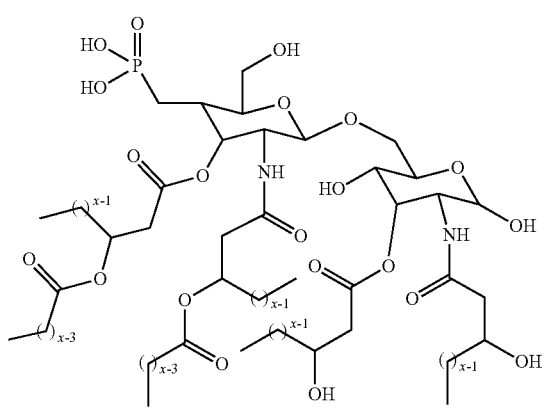

In a more specific embodiments of formula (VIII), x is 11, and the invention provides a GLA compound having the following structure (IX):

(IX)

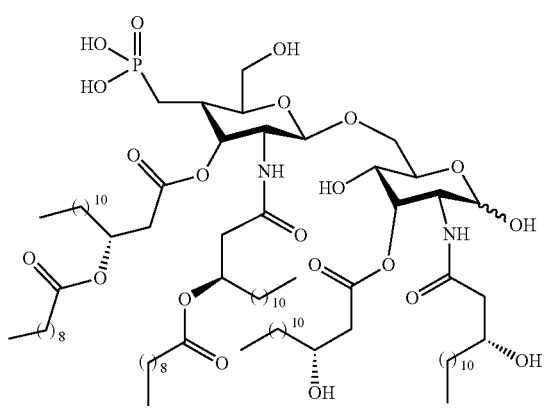

GLA Compounds

As mentioned above, the present invention provides GLA compounds. The GLA compounds of the present invention may be prepared by known organic synthesis techniques, including the methods described in more detail in the Examples. In general, the GLA compounds of structure (I) may be prepared by the following Reaction Schemes, wherein all substituents are as defined above unless indicated otherwise.

Reaction Scheme 1

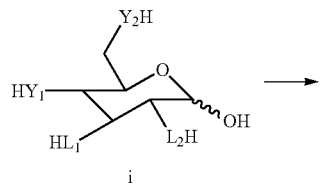

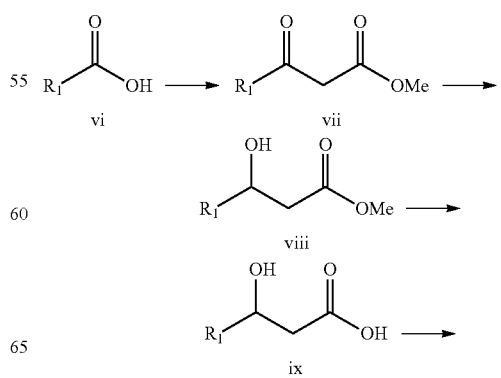

The sugar backbone of representative GLA compounds can be prepared generally according to Reaction Scheme 1, wherein $G_1$, $G_2$, $G_3$, $G_4$, $G_5$, $G_6$, $G_7$, $G_8$, $G_9$, and $G_{10}$ are either the same or different and independently an appropriate protecting group or hydrogen. An appropriate sugar, such as (i), can be purchased or prepared according to methods known to those skilled in the art. The functional groups of sugar (i) can then be fully protected using methods known to those skilled in the art to obtain (ii). In this respect, one skilled in the art will recognize that an appropriate orthogonal protecting group strategy which allows for selective deprotection of the sugar functional groups may be employed. Suitable protecting groups include, but are not limited to silylethers, benzyl ethers, allyloxycarbonyl, acetals, Fmoc, azide, and the like. Deprotection of $G_1$ results in free alcohol (iii) which can then be coupled with protected sugar (iv) using appropriate coupling conditions, for example $CCl_3CN/NaH$, to obtain the desired sugar backbone (v).

Reaction Scheme 2

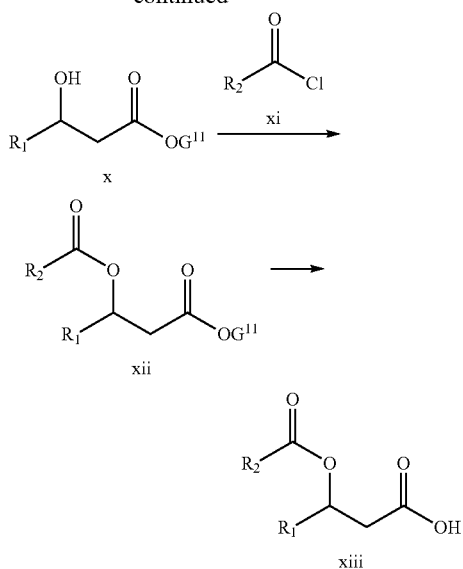

Representative GLA compound tail pieces, wherein $L_5$ and $L_6$ are both —O— and $L_7$, $L_8$, $L_9$, and $L^{10}$ are each —C(=O)—, can be prepared generally according to Reaction Scheme 2, wherein $G^{11}$ represents an appropriate protecting group. Acid compounds of structure (vi) can be purchased or prepared according to methods known to those skilled in the art. Reaction of (vi) with an appropriate reagent, such as methyl hydrogen malonate, yields ketoester (vii). Reduction of (vii) yields alcohol (viii). One skilled in the art will recognize that under appropriate conditions the keto group of (vii) may be reduced stereospecifically as exemplified in the Examples. Saponification of (viii) yields acid (ix) which can be subsequently protected to yield (x). Treatment of (x) with acid chloride (xi) yields (xii) which upon deprotection yields (xiii). Compounds (ix) and (xiii) may both be converted to a suitably protected acid chloride derivative by methods known to those skilled in the art and attached to the GLA compound sugar backbone as shown in Reaction Scheme 3 below. Although Reaction Scheme 2 depicts synthesis of a GLA compound tail piece comprising $R_1$ and $R_2$, it should be understood that other tail pieces comprising other alkyl groups (e.g. $R_3$, $R_4$, $R_5$, and $R_6$) may also be prepared by an analogous method. Other tail pieces with different $L_5$, $L_6$, $L_7$, $L_8$, $L_9$, and $L_{10}$ groups may also be prepared by analogous methods.

Reaction Scheme 3

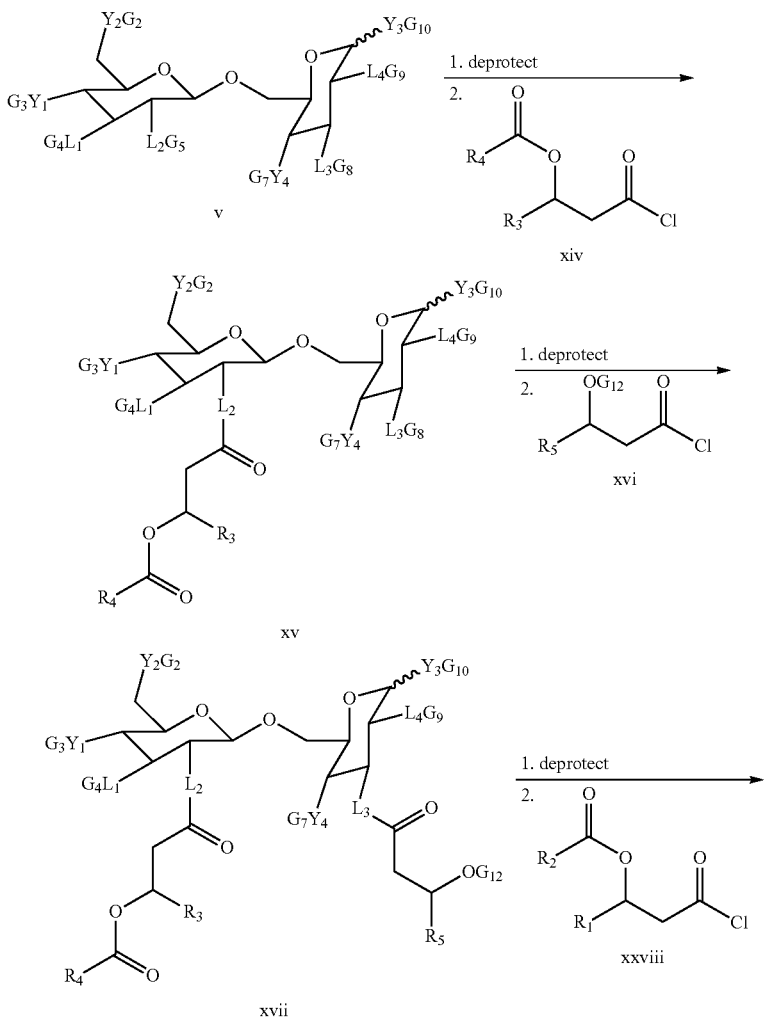

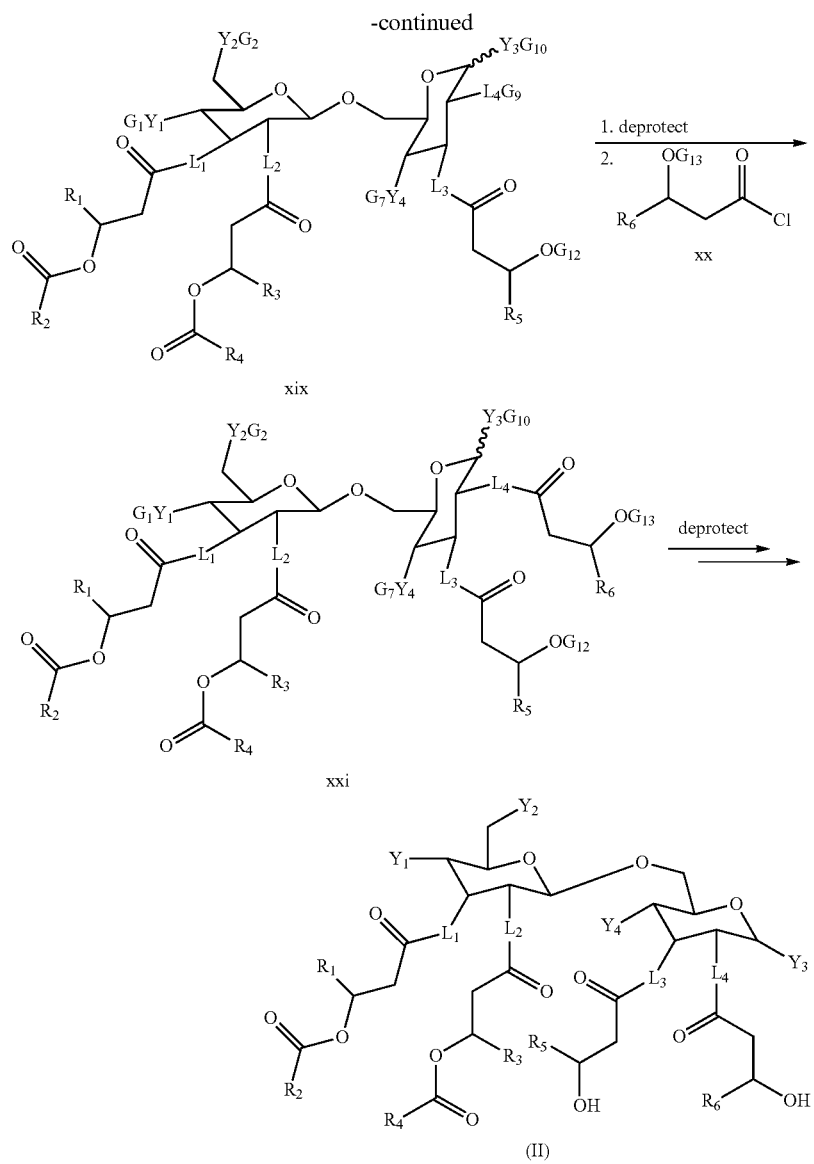

Representative GLA compounds can be prepared generally according to Reaction Scheme 3, wherein $G_{12}$ and $G_{13}$ are the same or different and independently represent an appropriate protecting group. Removal of the $G_5$ protecting group of (v) followed by reaction with acid chloride (xiv) produces (xv). Similarly, removal of the $G_8$ protecting group from (xv) followed by reaction with acid chloride (xvi) results in (xvii). Deprotection of (xvii) and reaction with acid chloride (xviii) yields (xix). Removal of $G_9$ and reaction with (xx) then produces the protected GLA compound (xxi). Global deprotection of (xxi) results in a compound of structure (II). Although Reaction Scheme 3 depicts the synthesis of a compound of structure (II), one skilled in the art will recognize that analogous methods may be employed to produce any compound of structure (i). In addition, one skilled in the art will also recognize that with selection of the appropriate protecting groups, the final deprotection results in the desired compound.

The compounds of the present invention may generally be utilized as the free base or free acid. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

Similarly, base addition salts of the acid compounds of the present invention may be prepared by methods well known in the art, and may be formed from organic and inorganic bases. Suitable organic bases include, but are not limited to, triethylamine and pyridine. Suitable inorganic bases include, but are not limited to, sodium hydroxide, potassium hydroxide, sodium carbonate, potassium carbonate, and ammonia. Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of a carboxylic acid (COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

Antigen

An antigen, for use in certain embodiments of the herein described vaccine compositions and methods employing GLA, may be any target epitope, molecule (including a biomolecule), molecular complex (including molecular complexes that contain biomolecules), subcellular assembly, cell or tissue against which elicitation or enhancement of immunreactivity in a subject is desired. Frequently, the term antigen will refer to a polypeptide antigen of interest. However, antigen, as used herein, may also refer to a recombinant construct which encodes a polypeptide antigen of interest (e.g, an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Preferably and in certain embodiments the vaccine formulations of the present invention contain an antigen or antigenic composition capable of eliciting an immune response against a human or other mammalian pathogen, which antigen or antigenic composition may include a composition derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by Gluck, *Vaccine*, 1992, 10, 915-920) or purified or recombinant proteins thereof, such as HA, NP. NA, or M proteins, or combinations thereof).

In certain other preferred embodiments the vaccine formulations of the present invention contain an antigen or antigenic composition capable of eliciting an immune response against a human or other mammlian pathogen, which antigen or antigenic composition may include a composition derived from one or more bacterial pathogens such as Neisseria spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M catarrhalis*, also known as *Branhamella catarrhalis* (for example high and low molecular weight adhesins and invasins); *Bordetella* spp, including *B. pertussis* (for example pertactin, *pertussis* toxin or derivatives thereof, filamentous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example Shiga toxin-like toxin or derivatives thereof); *Vibrio* spp, including *V. cholera* (for example *cholera* toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example *botulinum* toxin and derivative thereof), *C. difficile* (for example *clostridium* toxins A or B and derivatives thereof); *Bacillus* spp., including *B. anthracis* (for example *botulinum* toxin and derivatives thereof); *Corynebacterium* spp., including *C. diphtheriae* (for example diphtheria toxin and derivatives thereof); *Borrelia* spp. including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or other bacterial pathogens.

In certain other preferred embodiments the vaccine formulations of the present invention contain an antigen or antigenic composition capable of eliciting an immune response against a human or other mammalian pathogen, which antigen or antigenic composition may include a composition derived from one or more parasites (See, e.g., John, D. T. and Petri, W. A., *Markell and Voge's Medical Parasitology-9th* Ed., 2006, WB Saunders, Philadelphia; Bowman, D. D., *Georgis' Parasitology for Veterinarians-8th* Ed., 2002, WB Saunders, Philadelphia) such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leishmania* spp., including *L. major; Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichuria, Necator americanus, Ancylostoma duodenale, Wuchereria bancrofti, Brugia malayi, Onchocerca volvulus, Dracanculus medinensis, Trichinella spiralis*, and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). Certain embodiments may therefore contemplate vaccine compositions that include an antigen derived from *Schisostoma* spp., *Schistosoma mansonii, Schistosoma haematobium,* and/or *Schistosoma japonicum*, or derived from yeast such as *Candida* spp., including *C. albicans; Cryptococcus* spp., including *C. neoformans*.

Other preferred specific antigens for *M. tuberculosis* are for example Th Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748).

Certain preferred antigens for *Chlamydia* include for example the High Molecular Weight Protein (HWMP) (WO 99/17741), ORF3 (EP 366 412), CT622, CT610, pmpD, UVEB and putative membrane proteins (Props). Other *Chlamydia* antigens of the vaccine formulation can be selected from the group described in WO 99128475. Preferred bacterial vaccines comprise antigens derived from *Streptococcus* spp, including *S. pneumoniae* (for example capsular polysaccharides and conjugates thereof, PsaA, PspA, PdB, streptolysin, choline-binding proteins) and the protein antigen Pneumolysin (*Biochem Biophys Acta*, 1989, 67, 1007; Rubins et al., *Microbial Pathogenesis*, 25, 337-342), and mutant detoxified derivatives thereof (WO 90/06951; WO 99/03884). Other preferred bacterial vaccines comprise antigens derived from *Haemophilus* spp., including *H. influenzae* type B (for example PRP and conjugates thereof), nontypeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Derivatives of Hepatitis B Surface antigen are well known in the art and include, inter alia, those PreS1, Pars2 S antigens set forth described in European Patent applications EP-A414 374; EP-A-0304 578, and EP 198474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise antigen derived from the Human Papilloma Virus (HPV) considered to be responsible for genital warts (HPV 6 or HPV 11 and others), and the HPV viruses responsible for cervical cancer (HPV16, HPV18 and others). Particularly preferred forms of genital wart prophylactic, or therapeutic, vaccine comprise L1 particles or capsomers, and fusion proteins comprising one or more antigens selected from the HPV 6 and HPV 11 proteins E6, E7, L1, and L2. Certain preferred forms of fusion protein include L2E7 as disclosed in WO 96/26277, and proteinD(1/3)-E7 disclosed in GB 9717953.5 (PCT/EP98/05285). A preferred HPV cervical infection or cancer, prophylaxis or therapeutic vaccine, composition may comprise HPV 16 or 18 antigens. For example, L1 or L2 antigen monomers, or L1 or L2 antigens presented together as a virus like particle (VLP) or the L1 alone protein presented alone in a VLP or capsomer structure. Such antigens, virus like particles and capsomer are per se known. See for example WO94/00152, WO94/20137, WO94/05792, and WO93/02184.

Additional early proteins may be included alone or as fusion proteins such as E7, E2 or preferably F5 for example; particularly preferred embodiments include a VLP comprising L1E7 fusion proteins (WO 96/11272). Particularly preferred HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, preferably a Protein D-E6/E7 fusion. Such vaccine may optionally contain either or both E6 and E7 proteins front HPV 18, preferably in the form of a Protein D-E6 or Protein D-E7 fusion protein or Protein D E6/E7 fusion protein. The vaccine of the present invention may additionally comprise antigens from other HPV strains, preferably from strains HPV 31 or 33.

Vaccines of the present invention further comprise antigens derived from parasites that cause Malaria. For example, preferred antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

Accordingly, certain herein disclosed embodiment contemplate an antigen that is derived from at least one infectious pathogen such as a bacterium, a virus or a fungus, including an Actinobacterium such as *M. tuberculosis* or *M. leprae* or another mycobacterium; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (FIV), cytomegalovirus, Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces, Coccidioides* and *Pneumocysti* or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti, Giardia,* and *Leishmania.*

For example, in GLA-containing vaccine embodiments containing antigens derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Compositions and methods are known in the art for identifying subjects having, or suspected of being at risk for having, an infection with an infectious pathogen as described herein.

For example, the bacterium *Mycobacterium tuberculosis* cases tuberculosis (TB). The bacteria usually attack the lungs but can also attack the kidney, spine, and brain. If not treated properly, TB disease can be fatal. The disease is spread from one person to another in the air when an infected person sneezes or coughs. In 2003, more than 14,000 cases of TB were reported in the United States.

Although tuberculosis can generally be controlled using extended antibiotic therapy, such treatment is not sufficient to prevent the spread of the disease and concerns exist regarding the potential selection for antibiotic-resistant strains. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance. (e.g., U.S. Pat. No. 7,087,713)

Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium Bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48 72 hours after injection, which indicates exposure to Mycobacterial antigens. Sensitivity and specificity have, however, been a problem with this test, and individuals vaccinated with BCG cannot be distinguished from infected individuals. (e.g., U.S. Pat. No. 7,087,713)

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. Mycobacterium-reactive CD4 T cells have been shown to be potent producers of gamma-interferon (IFN-gamma), which, in turn, has been shown to trigger the anti-mycobacterial effects of macrophages in mice. While the role of IFN-gamma in humans is less clear, studies have shown that 1,25-dihydroxy-vitamin D3, either alone or in combination with IFN-gamma or tumor necrosis factor-alpha, activates human macrophages to inhibit *M. tuberculosis* infection. Furthermore, it is known that IFN-gamma stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection, see Chan and Kaufmann, in Tuberculosis: Pathogenesis, Protection and Control, Bloom (ed.), ASM Press. Washington, D.C. (1994).

Existing compounds and methods for diagnosing tuberculosis or for inducing protective immunity against tuberculosis include the use of polypeptides that contain at least one immunogenic portion of one or more *Mycobacterium* proteins and DNA molecules encoding such polypeptides. Diagnostic kits containing such polypeptides or DNA sequences and a suitable detection reagent may be used for the detection of *Mycobacterium* infection in patients and biological samples. Antibodies directed against such polypeptides are also provided. In addition, such compounds may be formulated into vaccines andior pharmaceutical compositions for immunization against *Mycobacterium* infection. (U.S. Pat. Nos. 6,949,246 and 6,555,653).

Malaria was eliminated in many parts of the world in the 1960s, but the disease still persists and new strains of the disease are emerging that are resistant to existing drugs. Malaria is a major public health problem in more than 90 countries. Nine out of ten cases of malaria occur in sub-Saharan Africa. More than one third of the world's population is at risk, and between 350 and 500 million people are infected with malaria each year. Forty-five million pregnant women are at risk of contracting malaria this year. Of those individuals already infected, more than 1 million of those infected die each year from what is a preventable disease. The majority of those deaths are children in Africa.

Malaria is usually transmitted when a person is bitten by an infected female Anopheles mosquito. To transmit the mosquito must have been infected by having drawn blood from a person already infected with malaria. Malaria is caused by a parasite and the clinical symptoms of the disease include fever and flu-like illness, such as chills, headache, muscle aches, and tiredness. These symptoms may be accompanied by nausea, vomiting, and diarrhea. Malaria can also cause anemia and jaundice because of the loss of red blood cells. Infection with one type of malaria, *Plasmodium*

*falciparum*, if not promptly treated, may cause kidney failure, seizures, mental confusion, coma, and death.

An in vitro diagnostic method for malaria in an individual is known, comprising placing a tissue or a biological fluid taken from an individual in contact with a molecule or polypeptide composition, wherein said molecule or polypeptide composition comprises one or more peptide sequences bearing all or part of one or more T epitopes of the proteins resulting from the infectious activity of *P. falciparum*, under conditions allowing an in vitro immunological reaction to occur between said composition and the antibodies that may be present in the tissue or biological fluid, and in vitro detection of the antigen-antibody complexes formed (see, e.g., U.S. Pat. No. 7,087,231).

Expression and purification of a recombinant *Plasmodium falciparum* (3D7) AMA-1 ectodomain have been described. Previous methods have produced a highly purified protein which retains folding and disulfide bridging of the native molecule. The recombinant AMA-1 is useful as a diagnostic reagentas well as in antibody production, and as a protein for use alone, or as part of, a vaccine to prevent malaria. (U.S. Pat. No. 7,029,685)

Polynucleotides have been described in the art that encode species-specific *P. vivax* malarial peptide antigens which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether Plasmodium vivax is the species responsible for the infection. (U.S. Pat. No. 6,706,872) Species-specific *P. vivax* malarial peptide antigens have also been reported which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection (see, e.g., U.S. Pat. No. 6,231,861).

A recombinant *Plasmodium falciparum* (3D7) AMA-1 ectodomain has also been expressed by a method that produces a highly purified protein which retains folding and disulfide bridging of the native molecule. The recombinant AMA-1 is useful as a diagnostic reagent, for use in antibody production, and as a vaccine. (U.S. Pat. No. 7,060,276) Similarly known are the expression and purification of a recombinant *Plasmodium falciparum* (3D7) MSP-1$_{42}$, which retains folding and disulfide bridging of the native molecule. The recombinant MSP-1$_{42}$ is useful as a diagnostic reagent, for use in antibody production, and as a vaccine. (U.S. Pat. No. 6,855,322)

Diagnostic methods for the detection of human malaria infections to identify a subject having or suspected of being at risk for having an infection with a malaria infectious pathogen are thus known according to these and related disclosures. Specifically, for example, blood samples are combined with a reagent containing 3-acetyl pyridine adenine dinucleotide (APAD), a substrate (e.g. a lactate salt or lactic acid), and a buffer. The reagent is designed to detect the presence of a unique glycolytic enzyme produced by the malaria parasite. This enzyme is known as parasite lactic acid dehydrogenase (PLDH). PLDH is readily distinguishable from host LDH using the above-described reagent. Combination of the reagent with a parasitized blood sample results in the reduction of APAD. However, APAD is not reduced by host LDH. The reduced APAD may then be detected by various techniques, including spectral, fluorimetric, electrophoretic, or colorimetric analysis. Detection of the reduced APAD in the foregoing manner provides a positive indication of malaria infection (e.g., U.S. Pat. No. 5,124,141). In another methodology for diagnosing malaria, a polypeptide comprising a characteristic amino acid sequence derived from the *Plasmodium falciparum* antigen GLURP, is recognized in a test sample by a specific antibody raised against or reactive with the polypeptide. (U.S. Pat. No. 5,231,168)

Leishmaniasis is a widespread parasitic disease with frequent epidemics in the Indian subcontinent, Africa, and Latin America and is a World Health Organization priority for vaccine development. A complex of different diseases, Leishmania parasites cause fatal infections of internal organs, as well as serious skin disease. One of the most devastating forms of leishmaniasis is a disfiguring infection of the nose and mouth. The number of cases of leishmaniasis is increasing, and it is now out of control in many areas. Leishmaniasis is also on the rise in some developed countries, specifically southern Europe as a result of HIV infection. Available drugs are toxic, expensive, and require long-term daily injections.

Leishmania are protozoan parasites that inhabit macrophages or the white blood cells of the immune system. The parasites are transmitted by the bite of small blood sucking insects (sand flies), which are difficult to control, as they inhabit vast areas of the planet.

Visceral leishmaniasis is the most dangerous of the three manifestations of the disease. It is estimated that about 500,000 new cases of the visceral form (kala-azar or "the killing disease") occur each year. More than 200 million people are currently at risk for contracting visceral leishmaniasis. Over 90 percent of visceral leishmaniasis cases occur in India, Bangladesh, Sudan, Brazil, and Nepal. Most of the deaths occur in children. Those with the cutaneous forms are often left permanently disfigured.

Leishmania infections are difficult to diagnose and typically involve histopathologic analysis of tissue biopsy specimens. Several serological and immunological diagnostic assays have, however, been developed. (U.S. Pat. No. 7,008, 774; Senaldi et al., (1996) *J. Immunol. Methods* 193:9 5; Zijlstra, et al., (1997) *Trans. R. Soc. Trap. Med. Hyg.* 91:671 673; Badaro, et al., (1996) J. Inf. Dis. 173:758 761; Choudhary, S., et al., (1992) *J. Comm. Dis.* 24:32 36; Badaro, R., et al., (1986) *Am. J. Trap. Med. Hyg.* 35:72 78; Choudhary, A., et al., (1990) *Trans. R. Soc. Trap. Med. Hyg.* 84:363 366; and Reed, S. G., et al., (1990) *Am. J. Trap. Med. Hyg.* 43:632 639). The promastigotes release metabolic products into the culture medium to produce conditioned medium. These metabolic products are immunogenic to the host. See Schnur, L. F., et al., (1972) Isrl. J. Med. Sci. 8:932 942; Sergeiev, V. P., et al., (1969) Med. Parasitol. 38:208 212; El-On, J., et al., (1979) Exper. Parasitol. 47:254 269; and Bray, R. S., et al., (1966) Trans. R. Soc. Trop. Med. Hyg. 60:605 609; U.S. Pat. No. 6,846,648, 5,912,166; 5,719,263; 5,411,865).

About 40 million people around the world are infected with HIV, the virus that causes AIDS. Around 3 million people die of the disease each year, 95 percent of them in the developing world. Each year, close to 5 million people become infected with HIV. Currently, sub-Saharan African carries the highest burden of disease, but it is quickly spreading to other countries such as India, China, and Russia. The epidemic is growing most rapidly among minority populations. In the United States there have been more than 950,000 cases of AIDS reported since 1981. AIDS hits people during their most productive years. Women, for both biological and social reasons, have an increased risk for HIV/AIDS.

AIDS is caused by human immunodeficiency virus (HIV), which kills and damages cells of the body's immune system and progressively destroys the body's ability to fight infections and certain cancers. HIV is spread most commonly by having unprotected sex with an infected partner. The most robust solution to the problem is preventing the virus from spreading. Making a safe, effective, and affordable HIV vaccine is one way to reach this goal. Across the world, fewer than one in five people at high risk for HIV infection have access to effective prevention.

Methods for diagnosing HIV infections are known, including by virus culture, PCR of definitive nucleic acid sequences from patient specimens, and antibody tests for the presence of anti-HIV antibodies in patient sera, (see e.g., U.S. Pat. Nos. 6,979,535, 6,544,728, 6,316,183, 6,261,762, 4,743,540.)

According to certain other embodiments as disclosed herein, the vaccine compositions and related formulations and methods of use may include an antigen that is derived from a cancer cell, as may be useful for the immunotherapeutic treatment of cancers. For example, the adjuvant formulation may finds utility with tumor rejection antigens such as those for prostate, breast, colorectal, lung, pancreatic, renal or melanoma cancers. Exemplary cancer or cancer cell-derived antigens include MACE 1, 3 and MACE 4 or other MACE antigens such as those disclosed in WO99/40188, PRAME, BADE, Lage (also known as NY Eos 1) SAGE and HAGE (WO 99/53061) or GAGE (Robbins and Kawakami, 1996 *Current Opinions in Immunology* 8, pps 628-636; Van den Eynde et al., *International Journal of Clinical & Laboratory Research* (1997 & 1998); Correale et al. (1997), *Journal of the National Cancer Institute* 89, p. 293. These non-limiting examples of cancer antigens are expressed in a wide range of tumor types such as melanoma, lung carcinoma, sarcoma and bladder carcinoma. See, e.g., U.S. Pat. No. 6,544,518.

Other tumor-specific antigens are suitable for use with GLA according to certain presently disclosed embodiments include, but are not restricted to, tumor-specific or tumor-associated gangliosides such as $GM_2$, and $GM_3$ or conjugates thereof to carrier proteins; or an antigen for use in a GLA vaccine composition for eliciting or enhancing an anti-cancer immune response may be a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., *Proc. Nat. Acad. Sci. USA* 95(4) 1735-1740 1998), PSMA or, in a preferred embodiment an antigen known as Prostase. (e.g., Nelson, et al., *Proc. Natl. Acad. Sci. USA* (1999) 96: 3114-3119; Ferguson, et al. *Proc. Natl. Acad. Sci. USA* 1999. 96, 3114-3119; WO 98/12307; U.S. Pat. No. 5,955,306; WO 98/20117; U.S. Pat. Nos. 5,840,871 and 5,786,148; WO 00/04149. Other prostate specific antigens are known from WO 98/137418, and WO1004149. Another is STEAP (*PNAS* 96 14523 14528 7-12 1999).

Other tumor associated antigens useful in the context of the present invention include: Plu-1 (*J Biol. Chem* 274 (22) 15633-15645, 1999), HASH-1, HasH-2, Cripto (Salomon et al *Bioessays* 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

The herein disclosed embodiments pertaining to GLA-containing vaccine compositions comprising a cancer antigen will be useful against any cancer characterized by tumor associated antigen expression, such as HER-2/neu expression or other cancer-specific or cancer-associated antigens.

Diagnosis of cancer in a subject having or suspected of being at risk for having cancer may be accomplished by any of a wide range of art-accepted methodologies, which may vary depending on a variety of factors including clinical presentation, degree of progression of the cancer, the type of cancer, and other factors. Examples of cancer diagnostics include histopathological, histocytochemical, immunohistocytochemical and immunohistopathological examination of patient samples (e.g., blood, skin biopsy, other tissue biopsy, surgical specimens, etc.), PCR tests for defined genetic (e.g., nucleic acid) markers, serological tests for circulating cancer-associated antigens or cells bearing such antigens, or for antibodies of defined specificity, or other methodologies with which those skilled in the art will be familiar. See, e.g., U.S. Pat. Nos. 6,734,172; 6,770,445; 6,893,820; 6,979,730; 7,060,802; 7,030,232; 6,933,123; 6,682,901; 6,587,792; 6,512,102; 7,078,180; 7,070,931; JP5-328975; Waslylyk et al., 1993 *Eur. J Bloch.* 211(7):18.

Vaccine compositions and methods according to certain embodiments of the present invention may also be used for the prophylaxis or therapy of autoimmune diseases, which include diseases, conditions or disorders wherein a host's or subject's immune system detrimentally mediates an immune response that is directed against "self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies, that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells (Akamizu et al., 1996; Kellerman et al., 1995; Raju et al., 1997; and Texier et al., 1992); pemphigus is cadherin-like pemphigus antigens such as desmoglein 3 and other adhesion molecules (Memar et al., 1996: Stanley, 1995; Plott et al., 1994; and Hashimoto, 1993); and thrombic thrombocytopenic purpura is antigens of platelets. (See, e.g., U.S. Pat. No. 6,929,796; Gorski et al. (Eds.), *Autoimmunity*, 2001, Kluwer Academic Publishers, Norwell, M A; Radbruch and Lipsky, P. E. (Eds.) *Current Concepts in Autoimmunity and Chronic Inflammation* (*Curr. Top. Microbial. and Immunol.*) 2001, Springer, NY.)

Autoimmunity plays a role in more than 80 different diseases, including type 1 diabetes, multiple sclerosis, lupus, rheumatoid arthritis, scleroderma, and thyroid diseases. Vigorous quantitative estimates of morbidity for most autoimmune diseases are lacking. Most recent studies done in the late 1990s reveal that autoimmune diseases are the third most common major illness in the United States; and the most common autoimmune diseases affect more than 8.5 million Americans. Current estimates of the prevalence of the disease range from 5 to 8 percent of the United States population. Most autoimmune diseases disproportionately affect women. Women are 2.7 times more likely than men to acquire an autoimmune disease. Women are more susceptible to autoimmune diseases; men appear to have higher levels of natural killer cell activity than do women. (Jacobsen et al, *Clinical Immunology and Immunopathology*, 84:223-243, 1997.)

Autoimmune diseases occur when the immune system mistakes self tissues for nonself and mounts an inappropriate attack. The body can be affected in different ways from autoimmune diseases, including, for example, the gut (Crohn's disease) and the brain (multiple sclerosis). It is known that an autoantibody attacks self-cells or self-tissues to injure their function and as a result causes autoimmune diseases, and that the autoantibody may be detected in the patient's serum prior to the actual occurrence of an autoimmune disease (e.g., appearance of clinical signs and symptoms). Detection of an autoantibody thus permits early discovery or recognition of presence or risk for developing an autoimmune disease. Based on these findings, a variety of autoantibodies against autoantigens have been discovered and the autoantibodies against autoantigens have been measured in clinical tests (e.g., U.S. Pat. Nos. 6,919,210, 6,596,501, 7,012,134, 6,919,078) while other autoimmune diagnostics may involve detection of a relevant metabolite (e.g., U.S. Pat. No. 4,659,659) or immunological reactivity (e.g., U.S. Pat. Nos. 4,614,722 and 5,147,785, 4,420,558, 5,298,396, 5,162,990, 4,420,461, 4,595,654, 5,846,758, 6,660,487).

In certain embodiments, the compositions of the invention will be particularly applicable in treatment of the elderly and/or the immunosuppressed, including subjects on kidney dialysis, subjects on chemo-therapy and/or radiation therapy, transplant recipients, and the like. Such individuals generally exhibit diminished immune responses to vaccines and therefore use of the compositions of the invention can enhance the immune responses achieved in these subjects.

In other embodiments, the antigen or antigens used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):S77-121). Exacerbations of COPD are often caused by bacterial (e.g. pneumococcal) infection (Clin Microbiol Rev. 2001 April; 14(2):336-63). In a particular embodiment, a composition of the invention comprises a GLA adjuvant, as described herein, in combination with the Pneumococcal vaccine Prevnar® (Wyeth).

In still other embodiments, the compositions of the invention, comprising GLA as described herein, are used in the treatment of allergic conditions. For example, in a particular embodiment, the compositions are used in allergy desensitization therapy. Such therapy involves the stimulation of the immune system with gradually increasing doses of the substances to which a person is allergic, wherein the substances are formulated in compositions comprising GLA. In specific embodiments, the compositions are used in the treatment of allergies to food products, pollen, mites, cats or stinging insects (e.g., bees, hornets, yellow jackets, wasps, velvet ants, fire ants).

TLR

As described herein, certain embodiments of the present invention contemplate vaccine compositions and immunological adjuvant compositions, including pharmaceutical compositions, that include, in addition to the GLA compound(s) of the invention, one or more toll-like receptor agonist (TLR agonist). Toll-like receptors (TLR) include cell surface transmembrane receptors of the innate immune system that confer early-phase recognition capability to host cells for a variety of conserved microbial molecular structures such as may be present in or on a large number of infectious pathogens. (e.g., Armant et al., 2002 *Genome Biol.* 3(8):reviews 3011.1-3011.6; Fearon et al., 1996 *Science* 272:50; Medzhitov et al., 1997 *Curr. Opin. Immunol.* 9:4; Luster 2002 *Curr. Opin. Immunol.* 14:129; Lien et al. 2003 *Nat. Immunol.* 4:1162; Medzhitov, 2001 *Nat. Rev. Immunol.* 1:135; Takeda et al., 2003 *Ann Rev Immunol.* 21:335: Takeda et al. 2005 *Int. Immunol.* 17:1; Kaisho et al., 2004 *Microbes Infect.* 6:1388; Datta et al., 2003 *J. Immunol.* 170:4102).

Induction of TLR-mediated signal transduction to potentiate the initiation of immune responses via the innate immune system may be effected by TLR agonists, which engage cell surface TLR. For example, lipopolysaccharide (LPS) may be a TLR agonist through TLR2 or TLR4 (Tsan et al., 2004 *J. Leuk. Biol.* 76:514; Tsan et al., 2004 *Am. J. Physiol. Cell Physiol.* 286:C739; Lin et al., 2005 *Shock* 24:206); poly(inosine-cytidine) (polyI:C) may be a TLR agonist through TLR3 (Salem et al., 2006 *Vaccine* 24:5119); CpG sequences (oligodeoxynucleotides containing unmethylated cytosine-guanosine or "CpG" dinucleotide motifs, e.g., CpG 7909, Cooper et al., 2005 ADS 19:1473; CpG 10101 Bayes et al. *Methods Find Exp Clin Pharmacol* 27:193; Vollmer et al. *Expert Opinion on Biological Therapy* 5:673; Vollmer et al., 2004 *Antimicrob. Agents Chemother.* 48:2314; Deng et al., 2004 *J. Immunol.* 173:5148) may be TLR agonists through TLR9 (Andaloussi et a., 2006 *Glia* 54:526; Chen et al., 2006 *J. lmmunol.* 177:2373); peptidoglycans may be TLR2 and/or TLR6 agonists (Saboll et al., 2006 *Biol. Reprod.* 75:131; Nakao et al., 2005 *J. Immunol.* 174:1566); 3M003 (4-amino-2-(ethoxymethyl)-α,α-dimethyl-6,7,8,9-tetrahydro-1H-imidazo[4,5-c]quinoline-1-ethanol hydrate, Mol. Wt. 318 Da from 3M Pharmaceuticals, St. Paul, Minn., which is also a source of the related compounds 3M001 and 3M002; Gorden et al., 2005 *J. Immunol.* 174:1259) may be a TLR7 agonist (Johansen 2005 *Clin. Exp. Allerg.* 35:1591) and/or a TLR8 agonist (Johansen 2005); flagellin may be a TLR5 agonist (Feuillet et al., 2006 *Proc. Nat. Acad. Sci. USA* 103:12487); and hepatitis C antigens may act as TLR agonists through TLR7 and/or TLR9 (Lee et al., 2006 *Proc. Nat. Acad. Sci. USA* 103:1828; Horsmans et al., 2005 *Hepatol.* 42:724). Other TLR agonists are known (e.g., Schirmbeck et al., 2003 *J. Immunol.* 171:5198) and may be used according to certain of the presently described embodiments.

For example, and by way of background (see, e.g., U.S. Pat. No. 6,544,518) immunostimulatory oligonucleotides containing unmethylated CpG dinucleotides ("CpG") are known as being adjuvants when administered by both systemic and mucosal routes (WO 96/02555, EP 468520, Davis et al., *J. Immunol*, 1998. 160(2):870-876; McCluskie and Davis, *J. Immunol.*, 1998, 161(9):4463-6). CpG is an abbreviation for cytosine-guanosine dinucleotide motifs present in DNA. The central role of the CG motif in immunostimulation was elucidated by Krieg, *Nature* 374, p546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present invention. CpG when formulated into vaccines, may be administered in free solution together with free antigen (WO 96/02555; McCluskie and Davis, supra) or covalently conjugated to an antigen (POT Publication No. WO 98/16247), or formulated with a carrier such as aluminium hydroxide (e.g., Davis et al. supra, Brazolot-Millan et al., *Proc. Nati. Acad. Sci., USA*, 1998, 95(26), 15553-8).

The preferred oligonucleotides for use in adjuvants or vaccines of the present invention preferably contain two or more dinucleotide CpG motifs separated by at least three, more preferably at least six or more nucleotides. The oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Examples of preferred oligonucleotides have sequences that are disclosed in the following publications; for certain herein disclosed embodiments the sequences preferably contain phosphorothioate modified internucleotide linkages:

CPG 7909: Cooper et al., "CPG 7909 adjuvant improves hepatitis B virus vaccine seroprotection in antiretroviral-treated HIV-infected adults." *AIDS*, 2005 Sep. 23; 19(14): 1473-9.

CpG 10101: Bayes et al., "Gateways to clinical trials." *Methods Find. Exp. Clin. Pharmacal.* 2005 April; 27(3): 193-219.

Vollmer J., "Progress in drug development of immunostimulatory CpG oligodeoxynucleotide ligands for TLR9." Expert Opinion on Biological Therapy. 2005 May; 5(5): 673-682

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present invention may be synthesized by any method known in the art (e.g., EP 468520). Conveniently, such oligonucleotides may be synthesized utilizing an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phosphodiesters. Other internucleotide bonds which stabilize the oligonucleotide may also be used.

Co-Adjuvant

Certain embodiments as provided herein include vaccine compositions and immunological adjuvant compositions, including pharmaceutical compositions, that contain, in addition to GLA compound(s), at least one co-adjuvant, which refers to a component of such compositions that has adjuvant activity but that is other than GLA. A co-adjuvant having such adjuvant activity includes a composition that, when administered to a subject such as a human (e.g., a human patient), a non-human primate, a mammal or another higher eukaryotic organism having a recognized immune system, is capable of altering (i.e., increasing or decreasing in a statistically significant manner, and in certain preferred embodiments, enhancing or increasing) the potency and/or longevity of an immune response. (See, e.g., Powell and Newman, "Vaccine design—The Subunit and Adjuvant Approach", 1995, Plenum Press, New York) In certain embodiments disclosed herein GLA and a desired antigen, and optionally one or more co-adjuvants, may so alter, e.g., elicit or enhance, an immune response that is directed against the desired antigen which may be administered at the same time as GLA or may be separated in time and/or space (e.g., at a different anatomic site) in its administration, but certain invention embodiments are not intended to be so limited and thus also contemplate administration of GLA in a composition that does not include a specified antigen but which may also include one or more of a TLR agonist, a co-adjuvant, an imidazoquinline immune response modifier, and a double stem loop immune modifier (dSLIM).

Accordingly and as noted above, co-adjuvants include compositions other than GLA that have adjuvant effects, such as saponins and saponin mimetics, including QS21 and QS21 mimetics (see, e.g., U.S. Pat. No. 5,057,540; EP 0 362 279 B1; WO 95/17210), alum, plant alkaloids such as tomatine, detergents such as (but not limited to) saponin, polysorbate 80, Span 85 and stearyl tyrosine, one or more cytokines (e.g., GM-CSF, IL-2, IL-7, IL-12, TNF-alpha, IFN-gamma), an imidazoquinoline immune response modifier, and a double stem loop immune modifier (dSLIM, e.g., Weeratna et al., 2005 *Vaccine* 23:5263).

Detergents including saponins are taught in, e.g., U.S. Pat. No. 6,544,518; Lacaille-Dubois, M and Wagner H. (1996 *Phytomedicine* 2:363-386), U.S. Pat. No. 5,057,540, Kensil, *Crit Rev Ther Drug Carrier Syst*, 1996, 12 (1-2):1-55, and EP 0 362 279 B1. Particulate structures, termed Immune Stimulating Complexes (ISCOMS), comprising fractions of Quil A (saponin) are haemolytic and have been used in the manufacture of vaccines (Morein, B., EP 0 109 942 B1). These structures have been reported to have adjuvant activity (EP 0 109 942 B1; WO 96/11711). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology 146:431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bomford et al., *Vaccine*, 10(9):572-577, 1992).

Escin is another detergent related to the saponins for use in the adjuvant compositions of the embodiments herein disclosed. Escin is described in the Merck index (12$^{th}$ Ed.: entry 3737) as a mixture of saponin occurring in the seed of the horse chestnut tree, *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin (also known as aescin) have been purified and shown to be biologically active (Yoshikawa M, et al. (Chem Pharm Bull (Tokyo) 1996 August; 44(8): 1454-1464)). Digitonin is another detergent, also being described in the Merck index (12th Ed., entry 3204) as a saponin, being derived from the seeds of *Digitalis purpurea* and purified according to the procedure described by Gisvold et al., *J. Am. Pharm. Assoc.*, 1934, 23, 664; and Rubenstroth-Bauer, *Physiol. Chem.*, 1955, 301, 621.

Other co-adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a GLA vaccine composition or a GLA immunological adjuvant include Pluronic® L121 (BASF Corp., Mount Olive, N.J.; see, e.g., Yeh et al., 1996 *Pharm. Res.* 13:1693; U.S. Pat. No. 5,565,209), CRL1005 (e.g., Triozzi et al., 1997 *Clin Canc. Res.* 3:2355), poly (lactic-co-glycolic acid) (PLGA), poly(lactic acid) (PLA), poly-(D,L-lactide-co-glycolide) (PLG), and polyl:C. (See, e.g., Powell and Newman, "Vaccine design—The Subunit and Adjuvant Approach", 1995, Plenum Press, New York)

Certain embodiments contemplate GLA vaccines and GLA immunological adjuvants that include an oil, which in some such embodiments may contribute co-adjuvant activity and in other such embodiments may additionally or alternatively provide a pharmaceutically acceptable carrier or excipient. Any number of suitable oils are known and may be selected for inclusion in vaccine compositions and immunological adjuvant compositions based on the present disclosure. Examples of such oils, by way of illustration and not limitation, include squalene, squalane, mineral oil, olive oil, cholesterol, and a mannide monooleate.

Immune response modifiers such as imidazoquinoline immune response modifiers are also known in the art and may also be included as co-adjuvants in certain presently disclosed embodiments. Certain preferred imidazoquinoline immune response modifiers include, by way of non-limiting example, resiquimod (R848), imiquimod and gardiquimod (Hemmi et al., 2002 *Nat. Immunol.* 3:196; Gibson et al., 2002 *Cell. Immunol.* 218:74; Gorden et al., 2005 *J. Immunol.* 174:1259); these and other imidazoquinoline immune response modifiers may, under appropriate conditions, also have TLR agonist activity as described herein. Other immune response modifiers are the nucleic acid-based double stem loop immune modifiers (dSLIM). Specific examples of dSLIM that are contemplated for use in certain of the presently disclosed embodiments can be found in Schmidt et al., 2006 *Allergy* 61:56; Weihrauch et al. 2005 *Clin Cancer Res.* 11(16):5993-6001; Modern Biopharmaceuticals, J. Knäblein (Editor). John Wiley & Sons, Dec. 6, 2005. (dSLIM discussed on pages 183 to ~200), and from Mologen AG (Berlin, FRG: [retrieved online on Aug. 18, 2006 at http://www.mologen.com/English/04.20-dSLIM.shtml].

As also noted above, one type of co-adjuvant for use with GLA as described herein may be the aluminum co-adjuvants, which are generally referred to as "alum." Alum co-adjuvants are based on the following: aluminum oxyhydroxide; aluminum hydroxyphoshoate; or various proprietary salts. Vaccines that use alum co-adjuvants may include vaccines for tetanus strains, HPV, hepatitis A, inactivated polio virus, and other antigens as described herein. Alum co-adjuvants are advantageous because they have a good safety record, augment antibody responses, stabilize antigens, and are relatively simple for large-scale production. (Edelman 2002 *Mol. Biotechnol.* 21:129-148; Edelman, R. 1980 *Rev. Infect. Dis.* 2:370-383.)

Other co-adjuvants that may be combined with GLA for effective immune stimulation include saponins and saponin mimetics, including QS21 and structurally related compounds conferring similar effects and referred to herein as QS21 mimetics. QS21 has been recognized as a preferred co-adjuvant. QS21 may comprise an HPLC purified nontoxic fraction derived from the bark of Quillaja Saponaria Molina. The production of QS21 is disclosed in U.S. Pat. No. 5,057,540. (See also U.S. Pat. Nos. 6,936,255, 7,029, 678 and 6,932,972.)

GLA may also in certain embodiments be combined with "immunostimulatory complexes" known as ISCOMS (e.g., U.S. Pat. Nos. 6,869,607, 6,846,489, 6,027,732, 4,981,684), including saponin-derived ISCOMATRIX®, which is commercially available, for example, from Iscotec (Stockholm, Sweden) and CSL Ltd. (Parkville, Victoria, Australia).

Recombinant Expression Construct

According to certain herein disclosed embodiments, the GLA vaccine composition may contain at least one recombinant expression construct which comprises a promoter operably linked to a nucleic acid sequence encoding an antigen. In certain further embodiments the recombinant expression construct is present in a viral vector, such as an adenovirus, adeno-associated virus, herpesvirus, lentivirus, poxvirus or retrovirus vector. Compositions and methods for making and using such expression constructs and vectors are known in the art, for the expression of polypeptide antigens as provided herein, for example, according to Ausubel et al. (Eds.), Current Protocols in Molecular Biology, 2006 John Wiley & Sons, NY. Non-limiting examples of recombinant expression constructs generally can be found, for instance, in U.S. Pat. Nos. 6,844,192; 7,037,712; 7,052,904; 7,001, 770; 6,106,824; 5,693,531; 6,613,892; 6,875,610; 7,067, 310; 6,218,186; 6,783,981; 7,052,904; 6,783,981; 6,734, 172; 6,713,068; 5,795,577 and 6,770,445 and elsewhere, with teachings that can be adapted to the expression of polypeptide antigens as provided herein, for use in certain presently disclosed embodiments.

Immune Response

The invention thus provides compositions for altering (i.e., increasing or decreasing in a statistically significant manner, for example, relative to an appropriate control as will be familiar to persons skilled in the art) immune responses in a host capable of mounting an immune response. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but the invention should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by up-regulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors.

Determination of the induction of an immune response by the vaccines of the present invention may be established by any of a number of well known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (*Immunology Methods Manual: The Comprehensive Sourcebook of Techniques,* 1998; see also *Current Protocols in Immunology;* see also, e.g., Weir, *Handbook of Experimental Immunology,* 1986 Blackwell Scientific, Boston, Mass.; Mishell and Shigii (eds.) *Selected Methods in Cellular Immunology,* 1979 Freeman Publishing, San Francisco, Calif.; Green and Reed, 1998 *Science* 281: 1309 and references cited therein).

Detection of the proliferation of antigen-reactive T cells may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antigen-specific antibody production may be achieved, for example, by assaying a sample (e.g., an immunoglobulin containing sample such as serum, plasma or blood) from a host treated with a vaccine according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & Systems, Minneapolis, Minn.).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), *Manual of Clinical Laboratory Immunology,* $5^{th}$ Ed., 1997 American Society of Microbiology, Washington, D.C.

Accordingly it is contemplated that the vaccine and adjuvant compositions provided herein will be capable of eliciting or enhancing in a host at least one immune response that is selected from a $T_H1$-type T lymphocyte response, a $T_H2$-type T lymphocyte response, a cytotoxic T lymphocyte (CTL) response, an antibody response, a cytokine response, a lymphokine response, a chemokine response, and an inflammatory response. In certain embodiments the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production one or a plurality of chemokines wherein the chemokine is selected from MIP-1α, MIP-1β, RANTES, CCL4 and CCL5, and a lymphocyte response that is selected from a memory T cell response, a memory B cell response, an effector T cell response, a cytotoxic T cell response and an effector B cell response. See, e.g., WO 94/00153; WO 95/17209; WO 96/02555; U.S. Pat. No. 6,692,752; 7,084, 256; 6,977,073; 6,749,856; 6,733,763; 6,797,276; 6,752, 995; 6,057,427; 6,472,515; 6,309,847; 6,969,704; 6,120, 769; 5,993,800; 5,595,888; Smith et al., 1987 J Biol Chem.

262:6951; Kriegler et al., 1988 Cell 53:45 53; Beutler et al., 1986 Nature 320:584; U.S. Pat. No. 6,991,791; 6,654,462; 6,375,944.

Pharmaceutical Compositions

Pharmaceutical compositions generally comprise at least one GLA compound of the invention, and may further comprise one or more components as provided herein that are selected, for example, from antigen, TLR agonist, co-adjuvant (including optionally a cytokine, an imidazoquinoline immune response modifier and/or a dSLIM), and/or a recombinant expression construct, in combination with a pharmaceutically acceptable carrier, excipient or diluent.

Therefore, in certain aspects, the present invention is drawn to GLA "monotherapy" wherein GLA, as described herein, is formulated in a composition that is substantially devoid of other antigens, and is administered to a subject in order to stimulate an immune e response, e.g., a non-specific immune response, for the purpose of treating or preventing a disease or other condition, such as for treating an infection by an organism, for treating seasonal rhinitis, or the like. In one embodiment, for example, the compositions and methods of the invention employ a GLA compound for stimulating an immune response in a subject. In another embodiment, the GLA is in the form of a spray, optionally provided in a kit.

The GLA may be preferably formulated in a stable emulsion. In one particular embodiment, for example, a composition is provided comprising a GLA compound of the invention in a stable emulsion substantially devoid of other antigens.

In certain other embodiments, the pharmaceutical composition is a vaccine composition that comprises both GLA and an antigen and may further comprise one or more components, as provided herein, that are selected from TLR agonist, co-adjuvant (including, e.g., a cytokine, an imidazoquinoline immune response modifier and/or a dSLIM) and the like and/or a recombinant expression construct, in combination with a pharmaceutically acceptable carrier, excipient or diluent.

Illustrative carriers will be nontoxic to recipients at the dosages and concentrations employed. For GLA-plus-nucleic acid-based vaccines, or for vaccines comprising GLA plus an antigen, about 0.001 µg/kg to about 100 mg/kg body weight will generally be administered, typically by the intradermal, subcutaneous, intramuscular or intravenous route, or by other routes.

In a more specific embodiment, the dosage is about 0.001 µg/kg to about 1 mg/kg. In another specific embodiment, the dosage is about 0.001 to about 50 µg/kg. In another specific embodiment, the dosage is about 0.001 to about 15 µg/kg. In another specific embodiment, the amount of GLA administered is about 0.01 µg/dose to about 5 mg/dose. In another specific embodiment, the amount of GLA administered is about 0.1 µg/dose to about 1 mg/dose. In another specific embodiment, the amount of GLA administered is about 0.1 µg/dose to about 100 µg/dose. In another specific embodiment, the GLA administered is about 0.1 µg/dose to about 10 µg/close.

It will be evident to those skilled in the art that the number and frequency of administration will be dependent upon the response of the host. "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compositions of the present invention may be used in either the free base or salt forms, with both forms being considered as being within the scope of the present invention.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic (e.g., U.S. Pat. Nos. 7,033, 598; 7,018,345; 6,970,739), sonophoretic (e.g., U.S. Pat. Nos. 4,780,212; 4,767,402; 4,948,587; 5,618,275; 5,656, 016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalene, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a pharmaceutical or vaccine composition of the invention comprises a stable aqueous suspension of less than 0.2 um and further comprises at least one component selected from the group consisting of phospholipids, fatty acids, surfactants, detergents, saponins, fluorodated lipids, and the like.

In another embodiment, a composition of the invention is formulated in a manner which can be aerosolized.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075, 109. In this regard, it is preferable that the microsphere be larger than approximately 25 microns.

Pharmaceutical compositions (including GLA vaccines and GLA immunological adjuvants) may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

As described above, in certain embodiments the subject invention includes compositions capable of delivering nucleic acid molecules encoding desired antigens. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. No. 4,769,330; 5,017, 487; and WO 89/01973)), recombinant expression construct nucleic acid molecules complexed to a polycationic molecule (see WO 93/03709), and nucleic acids associated with liposomes (see Wang et al., *Proc. Natl. Acad. Sci. USA* 84:7851, 1987). In certain embodiments, the DNA may be linked to killed or inactivated adenovirus (see Curiel et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264: 16985-16987, 1989) and lipid-DNA combinations (see Feigner et al., *Proc. Natl. Acad. Sci. USA* 84:7413-7417, 1989).

In addition to direct in vivo procedures, ex vivo procedures may be used in which cells are removed from a host, modified, and placed into the same or another host animal. it will be evident that one can utilize any of the compositions noted above for introduction of antigen-encoding nucleic acid molecules into tissue cells in an ex vivo context. Protocols for viral, physical and chemical methods of uptake are well known in the art.

Accordingly, the present invention is useful for enhancing or eliciting, in a host, a patient or in cell culture, an immune response. As used herein, the term "patient" refers to any warm-blooded animal, preferably a human. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

In certain embodiments a liquid composition intended for either parenteral or oral administration should contain an amount of GLA vaccine composition such that a suitable dosage will be obtained. Typically, this amount is at least 0.01 wt % of an antigen in the composition. When intended for oral administration, this amount may be varied to be between 0.1 and about 70% of the weight of the composition. Preferred oral compositions contain between about 4% and about 50% of the antigen. Preferred compositions and preparations are prepared so that a parenteral dosage unit contains between 0.01 to 1% by weight of active composition.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the antigen (e.g., GLA-antigen vaccine composition) or GLA (e.g., immunological adjuvant composition; GLA is available from Avanti Polar Lipids, Inc., Alabaster, Ala.; e.g., product number 699800) of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In the methods of the invention, the vaccine compositions/adjuvants may be administered through use of insert(s), bead(s), timed-release formulation(s), patch(es) or fast-release formulation(s).

Also contemplated in certain embodiments are kits comprising the herein described GLA vaccine compositions and/or GLA immunological adjuvant compositions, which may be provided in one or more containers. In one embodiment all components of the GLA vaccine compositions and/or GLA immunological adjuvant compositions are present together in a single container, but the invention embodiments are not intended to be so limited and also contemplate two or more containers in which, for example, a GLA immunological adjuvant composition is separate from, and not in contact with, the antigen component. By way of non-limiting theory, it is believed that in some cases administration only of the GLA immunological adjuvant composition may be performed beneficially, whilst in other cases such administration may beneficially be separated temporally and/or spatially (e.g., at a different anatomical site) from administration of the antigen, whilst in still other cases administration to the subject is beneficially conducted of a GLA vaccine composition as described herein and containing both antigen and GLA, and optionally other herein described components as well.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Preferred examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

Emulsion systems may also be used in formulating compositions of the present invention. For example, many single or multiphase emulsion systems have been described. Oil in water emulsion adjuvants per se have been suggested to be useful as adjuvant composition (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B). The oil emulsion adjuvants for use in the present invention may be natural or synthetic, and may be mineral or organic. Examples of mineral and organic oils will be readily apparent to the man skilled in the art.

In a particular embodiment, a composition of the invention comprises an emulsion of oil in water wherein the GLA is incorporated in the oil phase. In another embodiment, a composition of the invention comprises an emulsion of oil in water wherein the GLA is incorporated in the oil phase and wherein an additional component is present, such as a co-adjuvant, TLR agonist, or the like, as described herein.

In order for any oil in water composition to be suitable for human administration, the oil phase of the emulsion system preferably comprises a metabolizable oil. The meaning of the term metabolizable oil is well known in the art. Metabolizable can be defined as "being capable of being transformed by metabolism" (Dorland's illustrated Medical Dictionary, W. B. Saunders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils are also part of this invention and can include commercially available oils such as NEOBEE® and others.

Squalene (2,6,10,15,19,23-Hexamethyl-2,6,10,14,18,22-tetracosahexaene), for example, is an unsaturated oil which is found in large quantities in shark-liver oil, and in lower quantities in olive oil, wheat germ nil, rice bran oil, and yeast, and is a particularly preferred oil for use in this invention. Squalene is a metabolizable oil virtue of the fact that it is an intermediate in the biosynthesis of cholesterol (Merck index, 10th Edition, entry no. 8619). Particularly preferred oil emulsions are oil in water emulsions, and in particular squalene in water emulsions. In addition, the most preferred oil emulsion adjuvants of the present invention comprise an antioxidant, which is preferably the oil .alpha.-tocopherol (vitamin E. EP 0 382 271 B1). WO 95/17210 and WO 99/11241 disclose emulsion adjuvants based on squalene, alpha-tocopherol, and TWEEN® 80, optionally formulated with the immunostimulants QS21 and/or 3D-MPL (which are discussed above). WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges The amounts of the components present in the oil emulsions of the present invention are conventionally in the range of from 2 to 10% oil, such as squalene; and when present, from 2 to 10% alpha tocopherol; and from 0.3 to 3% surfactant, such as polyoxyethylene sorbitan monooleate. Preferably the ratio of oil: alpha tocopherol is equal or less than 1 as this provides a more stable emulsion. Span 85 may also be present at a level of about 10, In some cases it may be advantageous that the vaccines of the present invention will further contain a stabilizer.

The method of producing oil in water emulsions is well known to the person skilled in the art. Commonly, the method comprises the mixing the oil phase with a surfactant such as a PBS/TWEEN80® solution, followed by homogenization using a homogenizer. For instance, a method that comprises passing the mixture once, twice or more times through a syringe needle would be suitable for homogenizing small volumes of liquid. Equally, the emulsification process in a microfluidizer (M110S microfluidics machine, maximum of 50 passes, for a period of 2 minutes at maximum pressure input of 6 bar (output pressure of about 850 bar)) could be adapted to produce smaller or larger volumes of emulsion. This adaptation could be achieved by routine experimentation comprising the measurement of the resultant emulsion until a preparation was achieved with oil droplets of the required diameter.

The following Examples are offered by way of illustration and not by way of limitation.

EXAMPLES

Example 1

2-AZIDO-2-DEOXY-D-GLUCOPYRANOSIDE (2)

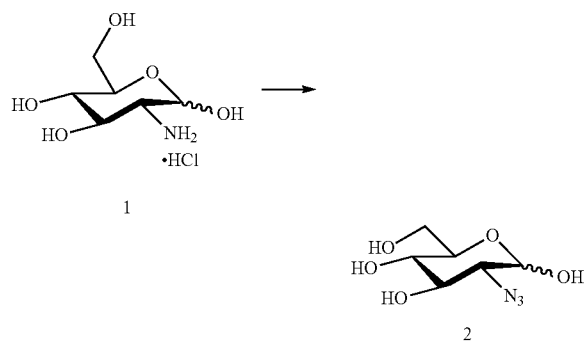

Sodium azide (2.78 g, 42.7 mmol) was dissolved in water (7 mL) and toluene (7 mL). The mixture was cooled to 0° C. under vigorous stirring. Triflic anhydride (4.57 mL, 27.2 mmol) was added dropwise, and the mixture was stirred for 30 min at 0° C. The temperature was raised to 10° C. and the biphasic mixture was stirred for 2 h. A saturated aqueous solution of sodium hydrogencarbonate was added dropwise until gas evolution had ceased. The two phases were separated, and the aqueous layer was extracted with toluene (2×7 mL). The combined organic layers were used in the subsequent diazo transfer reaction.

Glucose amine 1 (2.04 g, 9.45 mmol), sodium hydrogencarbonate (3.21 g, 38.22 mmol), and copper(II) sulfate pentahydrate (90.5 mg, 0.362 mmol) were dissolved in water (12.3 mL). The triflic azide stock solution prepared above (21 mL) was added, followed by the addition of methanol (81 mL) to yield a homogeneous system. The blue mixture was stirred vigorously at room temperature. Complete consumption of the amine was monitored by TLC (ninhydrin stain) and is also indicated by a color change of the mixture from blue to green. The solvents were removed in vacuo with a rotary evaporator keeping the temperature strictly below 25° C. The residue was purified by chromatography on silica gel (120 g RediSep column, eluting with a gradient of 0% through 40% methanol/dichloromethane over 50 min, 85 mL/min) to give product 2 (1.93 g, 99%) as a colorless liquid. $^1$H NMR (300 MHz, CD$_3$OD) (mixture of diastereomers 1/1) δ 5.18 (d, J=3.4 Hz, 0.5H), 4.51 (d, J=8.0 Hz, 0.5H), 3.89-3.63 (m, 3H), 3.32-3.26 (m, 2H), 3.11-3.06 (m, 1H).

Example 2

2-AZIDO-2-DEOXY-4,6-O-BENZYLIDENE-D-GLUCOPYRANOSIDE (3)

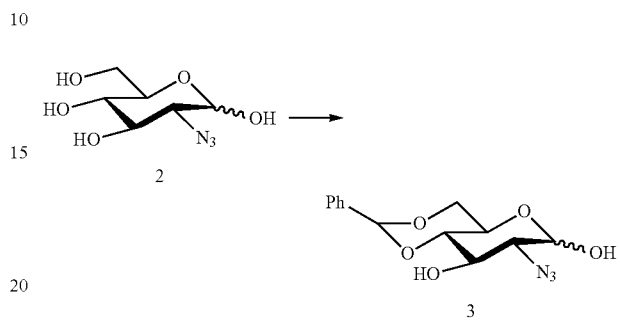

To a solution of compound 2 (2.00 g, 9.75 mmol) in DMF (40 mL) was added benzaldehyde dimethyl acetal (1.65 g, 10.8 mmol) and camphorsulfonic acid (90 mg). The flask was connected to a vacuum system, and the mixture was heated at 50° C. in an oil bath. After 3 h, the mixture was concentrated using a rotary evaporator. The residue was re-dissolved in diethyl ether (50 mL) and Et$_3$N (2 mL) followed by saturated sodium bicarbonate (50 mL). The aqueous layer was extracted with diethyl ether (3×50 mL). The combined organic extracts were dried over sodium sulfate and filtered. After the removal of solvents using a rotary evaporator, the residue was purified by chromatography on silica gel (120 g RediSep column, eluting with a gradient of 0% through 100% ethyl acetate/hexanes over 50 min, 85 mL/min) to give product 3 (2.58 g, 90%) as a colorless liquid. $^1$H NMR (300 MHz, CD$_3$OD) δ 7.49-7.32 (m, 5H), 5.58 (s, 1H), 4.64 (d, J=3.8 Hz, 1H), 4.25-341 (m, 5H), 3.23-3.20 (m, 1H).

Example 3

TERT-BUTYLDIMETHYLSILYL-2-AZIDO-4,6-O-BENZYLIDENE-2-DEOXY-β-D-GLUCOPYRANOSIDE (4)

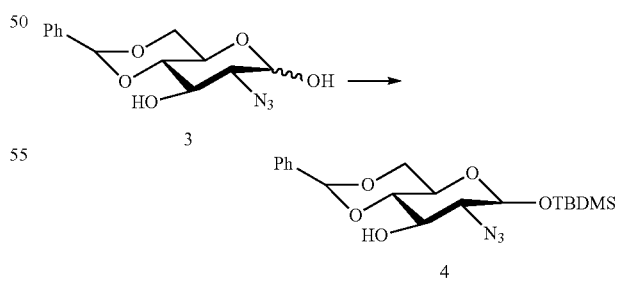

t-Butyidimethylsilyi chloride (820 mg, 5.44 mmol) was added to a mixture of compound 3 (1.45 g, 4.94 mmol) and imidazole (768 mg, 11.3 mmol) in CH$_2$Cl$_2$ (40 mL) at 0° C. After the solution was stirred overnight, saturated sodium bicarbonate (20 mL) was added, and the mixture was extracted with diethyl ether (3×30 mL). The combined organic layers were dried over Na₂SO₄, filtered, and concentrated in vacuo. The residue was purified by flash column chromatography (80 g RediSep column, eluting with a gradient of 0% through 70% ethyl acetate/hexanes over 40 min, 60 mL/min) to yield product 4 (1.5 g, 74%) as a colorless solid. ¹H NMR (300 MHz, CDCl₃) δ 7.46-7.43 (m, 2H), 7.35-7.32 (m, 3H), 5.48 (s. 1H), 4.59 (d, J=7.6 Hz, 1H), 4.23 (dd, J=10.2, 5.0 Hz, 1H), 3.73 (t, J=10.2 Hz, 1H), 3.56-3.51 (m, 2H), 3.31-3.28 (m, 2H), 2.72 (d, J=2.2 Hz, 1H), 0.91 (s, 9H), 0.14 (s, 3H), 0.13 (s, 3H).

Example 4

TERT-BUTYLDIMETHYLSILYL-3-O-ALLY-LOXYCARBONYL-2-AZIDO-4,6-O-BENZYLDI-DINE-2-DEOXY-D-GLUCOPYRANOSIDE (5)

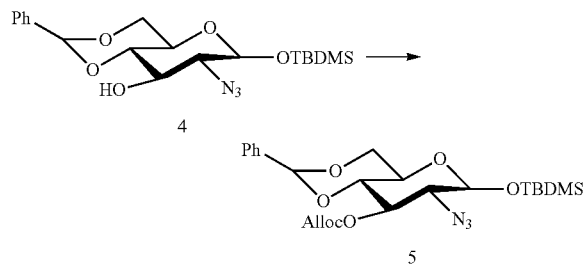

To a solution of compound 4 (1.50 g, 3.68 mmol) and tetramethyle hylenediamine (TMEDA) (0.78 mL, 5.2 mmol) in dichloromethane (DCM) (50 mL) at 0° C. was added allyl chloroformaie (0.78 mL, 7.3 mmol) dropwise. The mixture was allowed to warm to room temperature, and the mixture was stirred at room temperature for 10 h. The mixture was diluted with DCM (50 mL) and washed with saturated aqueous NaHCO₃ (2×100 mL) and brine (2×50 mL). The combined organic layers were dried over Na₂SO₄, filtered, and concentrated in vacuo. The residue was purified by flash column chromatography (80 g RediSep column, eluting with a gradient of 0% through 50% ethyl acetate/hexanes over 40 min, 60 mL/min) to yield product 5 (1.57 g, 87%) as a colorless solid. R$_f$=0.40 (hexanes/ethyl acetate, 3/1, v/v). ¹H NMR (300 MHz, CDCl₃) δ 7.44-7.41 (m, 2H). 7.35-7.32 (m, 3H), 5.98-5.85 (m, 1H), 5.48 (s, 1H), 5.38-5.22 (m, 2H), 4.88 (t, J=11.4 Hz, 1H), 4.72-4.64 (m, 3H), 4.32-4.27 (m, 1H), 3.81-3.65 (m, 2H), 3.50-3.42 (m, 2H), 0.94 (s, 9H), 0.18 (s, 3H), 0.17 (s, 3H).

Example 5

TERT-BUTYLDIMETHYLSILYL-3-O-ALLY-LOXYCARBONYL-2-AZIDO-6-O-BENZYL-2-DEOXY-D-GLUCOPYRANOSIDE (6)

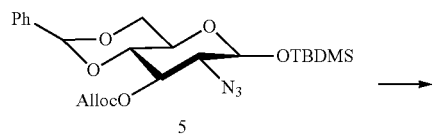

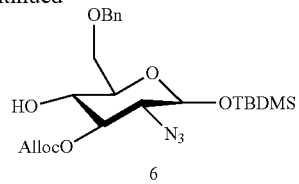

A suspension of compound 5 (320 mg, 0.651 mmol) and molecular sieves (4 Å, 200 mg) in THF (5 mL) was stirred at room temperature for 1 h, and then NaCNBH₃ (246 mg, 3.91 mmol) was added. A solution of hydrogen chloride (2 M in diethyl ether) was added dropwise to this mixture until the mixture became acidic (~5 mL, pH=5). After being stirred another 0.5 h, the reaction mixture was quenched with solid NaHCO₃, diluted with diethyl ether (100 mL), and washed with saturated aqueous NaHCO₃ (2×100 mL) and brine (2×50 mL). The organic layer was dried over Na₂SO₄, filtered, concentrated in vacuo, and the residue was purified by flash column chromatography (40 g RediSep column, eluting with a gradient of 0% through 100% ethyl acetate/hexanes over 40 min, 40 mL/min) to yield product 6 (273 mg, 85%) as a colorless solid. R$_f$=0.42 (hexanes/ethyl acetate, 4/1, v/v). ¹H NMR (300 MHz, CDCl₃) δ 7.39-7.34 (m, 5H), 5.99-5.89 (m, 1H), 5.40-5.26 (m, 2H), 4.67-4.56 (m, 5H), 3.72-3.70 (m, 3H), 3.48-3.46 (m, 2H), 3.37 (dd, J=9.6, 8.4 Hz, 1H), 3.01 (broad s, 1H), 0.94 (s, 9H), 0.17 (s, 6H).

Example 6

TERT-BUTYLDIMETHYLSILYL-3-O-ALLY-LOXYCARBONYL-2-AZIDO-6-O-BENZYL-2-DEOXY-4-O-(1,5-DIHYDRO-3-OXO-3λ⁵-3H-2,4,3-BENZODIOXAPHOSPHEPIN-3-YL)-D-GLUCOPYRANOSIDE (7)

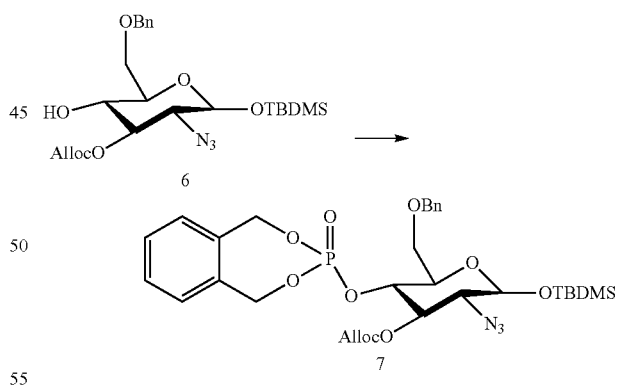

To a solution of compound 6 (5.47 g, 11.1 mmol) and 1H-tetrazole (3 wt % in acetonitrile, 35.5 mmol, 104 mL) was added N,N-diethyl-1,5-dihydro-3H-2,4,3-benzodioxa-phosphepin-3-amine (5.3 g. 22 mmol). After the reaction mixture was stirred at room temperature for 15 min, it was cooled to −20° C., stirred for another 10 min at that temperature, and then mCPBA (8.40 g, 50-55 wt %, 24.4 mmol) was added. The reaction mixture was stirred at −20° C. for 20 min, and concentrated in vacuo. The residue was redissolved in DCM (30 mL) and washed with saturated aqueous NaHCO₃ (40 mL). The aqueous layer was extracted with DCM (3×50 mL). The combined organic layers were dried over Na$_2$SO$_4$, filtered, and concentrated in vacuo. The residue was purified by flash column chromatography (120 g RediSep column, eluting with a gradient of 0% through 100% ethyl acetate/hexanes over 60 min, 85 mL/min) to yield product 7 (4.85 g, 65%) as a pale yellow oil. R$_f$=0.40 (hexanes/ethyl acetate, 1/1, v/v). $^1$H NMR (300 MHz. CDCl$_3$) δ 7.35-7.18 (m, 9H), 5.98-5.85 (m. 1H), 5.41-5.05 (m, 6H), 4.64 (t, J=10.1 Hz, 1H), 4.58-4.52 (m, 6H), 3.83 (d, J=9.0 Hz, 1H), 3.72-3.61 (m, 2H), 3.41 (dd, J=10.5, 7.4 Hz, 1H), 0.92 (s, 9H), 0.16 (s, 3H), 0.15 (s, 3H).

Example 7

TERT-BUTYLDIMETHYLSILYL-3-O-ALLY-LOXYCARBONYL-6-O-BENZYL-2-DEOXY-4-O-(1,5-DIHYDRO-3-OXO-3λ$^5$-3H-2,4,3-BENZODI-OXAPHOSPHEPIN-3-YL)-2-(9-FLUORENYLMETHOXYCARBONYLAMINO)-D-GLUCOPYRANOSIDE (8)

dried (MgSO$_4$) and filtered. The filtrate was concentrated in vacuo. The residue was purified by silica gel column chromatography (40 g RediSep column, eluting with a gradient of 0% through 100% ethyl acetate/hexanes over 30 min, 40 mL/min) to give product 8 (337 mg, 73% over two steps) as a white solid. R$_f$=0.54 (hexanes/ethyl acetate, 1/1, v/v). $^1$H NMR (300 MHz, CDCl$_3$) δ 7.78-7.20 (m, 17H), 5.92-5.82 (m, 1H), 5.49-5.16 (m, 8H), 4.69-4.06 (m, 5H), 4.49-4.28 (m, 2H), 3.88-3.61 (m, 3H), 3.60-3.51 (m, 2H), 3.32 (broad s, 1H), 0.94 (s, 9H), 0.14 (s, 3H), 0.10 (s, 3H).

Example 8

3-O-ALLYLOXYCARBONYL-6-O-BENZYL-2-DEOXY-4-O-(1,5-DIHYDRO-3-OXO-3λ$^5$-3H-2,4,3-BENZODIOXAPHOSPHEPIN-3-YL)-2-(9-FLUORENYLMETHOXYCARBONYLAMINO)-D-GLUCOPYRANOSIDE (9)

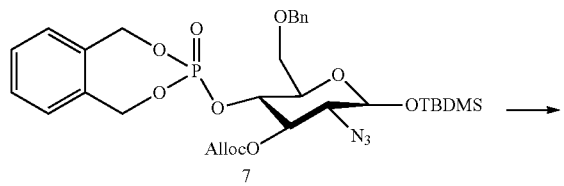

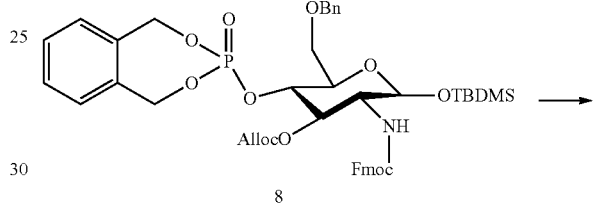

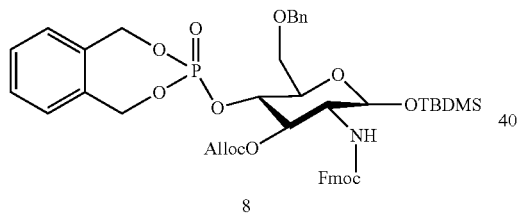

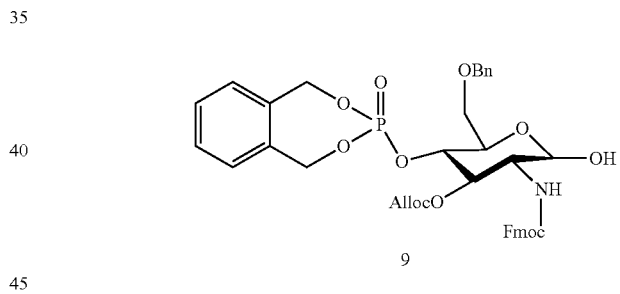

Acetic acid (0.30 mL, 5.2 mmol) was added dropwise to a stirred suspension of 7 (700 mg, 1.04 mmol) and zinc powder (676 mg, 10.4 mmol) in DCM (15 mL). The reaction mixture was stirred at room temperature for 4 h, after which it was diluted with ethyl acetate (50 mL). The solids were removed by filtration and washed with ethyl acetate (2×10 mL). The combined filtrates were washed with saturated aqueous NaHCO$_3$ (2×40 mL) and brine (2×40 mL). The organic phase was dried (MgSO$_4$) and filtered, and the filtrate was concentrated in vacuo to afford the crude intermediate amine as a pale yellow oil. R$_f$=0.21 (hexanes/ethyl acetate, 1/1, v/v). 9-Fluorenylmethyloxycarbonyl chloride (Fmoc-Cl) (323 mg, 1.25 mmol) was added to a stirred solution of the crude amine and diisopropylethylamine (DIPEA) (0.22 mL, 1.3 mmol) in DCM (15 mL) at 0° C. The reaction mixture was warmed and stirred at room temperature for 5 h, after which it was diluted with DCM (40 mL) and washed with brine (2×50 mL). The organic phase was Hydrogen fluoride/pyridine (6 mL, 0.2 mol) was added dropwise to a stirred solution of 8 (6.00 g, 6.88 mmol) in THF (50 mL). The reaction mixture was stirred at room temperature for 12 h, after which it was diluted with diethyl ether (100 mL), and then washed with saturated aqueous NaHCO$_3$ (2×40 mL) and brine (2×40 mL). The organic phase was dried (MgSO$_4$) and filtered. The filtrate was concentrated in vacuo. The residue was purified by silica gel column chromatography (120 g RediSep column, eluting with a gradient of 0% through 80% ethyl acetate/hexanes over 60 min, 85 mL./min) to give product 9 (4.34 g, 83%) as a pale yellow oil. $^1$H NMR (300 MHz. CDCl$_3$) δ 7.75-7.20 (m, 17H), 5.92-5.82 (m, 1H), 5.27-5.06 (m, 9H). 4.59-4.55 (m, 5H), 4.41-4.39 (m, 1H), 4.25-4.01 (m, 5H), 3.85-3.65 (m, 2H).

Example 9

TERT-BUTYLDIMETHYLSILYL-6-O-{3-O-AL-LYLOXYCARBONYL-6-O-BENZYL-2-DEOXY-4-O-(1,5-DIHYDRO-3-OXO-3λ$^5$-3H-2,4,3-BEN-ZODIOXAPHOSPHEPIN-3-YL)-2-[(R)-3-DODECANOYLOXY-TETRADECANOYLAMINO]-β-D-GLUCOPYRANOSYL}-2-AZIDO-4-O-BENZYL-3-O-[(R)-3-BENZYLOXY-DODECANOYL]-2-DEOXY-β-D-GLUCOPYRANOSIDE (11)

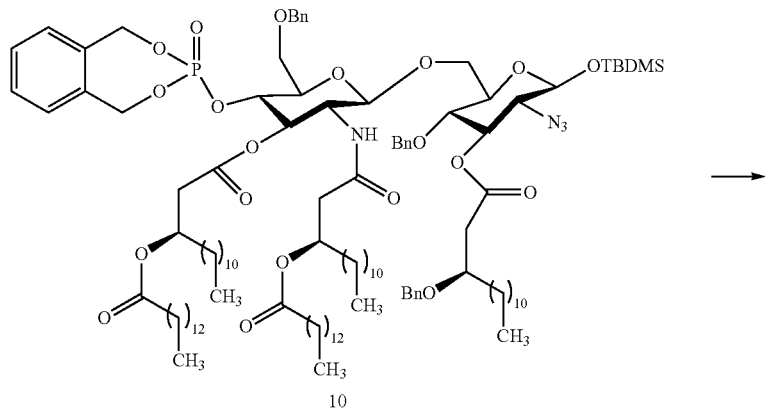

10

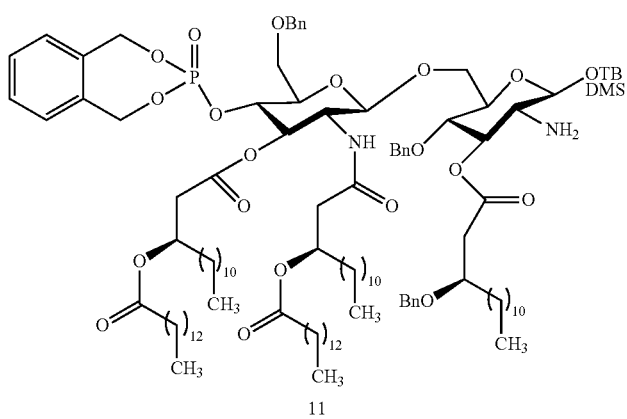

11

A suspension of 10 (see preparation below) (350 mg, 0.172 mmol), zinc (1.3 g, 21 mmol), and acetic acid (0.70 mL, 12 mmol) in DCM (20 mL) was stirred at room temperature for 12 h. The mixture was diluted with diethyl ether. The solids were removed by filtration, and the residue was washed with diethyl ether (2×10 mL). The combined filtrates were washed with saturated aqueous NaHCO$_3$ (2×15 mL) and brine (2×15 mL). The organic phase was dried (MgSO$_4$) and filtered. The filtrate was concentrated in vacuo, and the residue was purified by silica gel column chromatography (12 g RediSep column, eluting with a gradient of 0% through 60% ethyl acetate/hexanes over 35 min, 30 mL/min) to afford product 11 (220 mg, 64%) as a pale yellow syrup. $R_f$=0.29 (hexanes/ethyl acetate, 5/2, v/v). $^1$H NMR (300 MHz, CDCl$_3$) δ 7.37-7.24 (m, 20H), 6.20 (d, J=7.2 Hz, 1H), 5.59 (t, J=9.6 Hz, 1H), 5.31 (m, 1H), 5.12-4.97 (m, 6H), 4.62-4.44 (m, 7H), 4.05-3.24 (m, 9H), 2.68-2.12 (m. 9H), 1.64-1.59 (m, 13H), 1.27 (broad m, 95H), 0.94 (m, 25H), 0.13 (s, 6H). HRMS (m/z) (pos) calcd for C$_{117}$H$_{193}$N$_2$O$_{20}$PSi, 2005.37; found, 2006.3729 [M+H]$^+$.

Example 10

TERT-BUTYLDIMETHYLSILYL-6-O-{3-O-AL-LYLOXYCARBONYL-6-O-BENZYL-2-DEOXY-4-O-(1,5-DIHYDRO-3-OXO-3λ$^5$-3H-2,4,3-BEN-ZODIOXAPHOSPHEPIN-3-YL)-2-[(R)-3-DODECANOYLOXY-TETRADECANOYLAMINO]-β-D-GLUCOPYRANOSYL}-4-O-BENZYL-3-O-[(R)-3-BENZYLOXY-DODECANOYL]-2-[(R)-3-4-METHOXYBENZYLOXY-TETRADECANOYL]-2-DEOXY-β-D-GLUCOPYRANOSIDE (12)

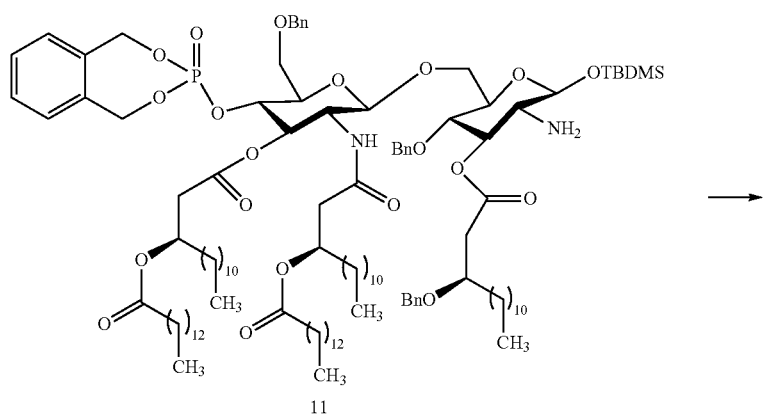

11

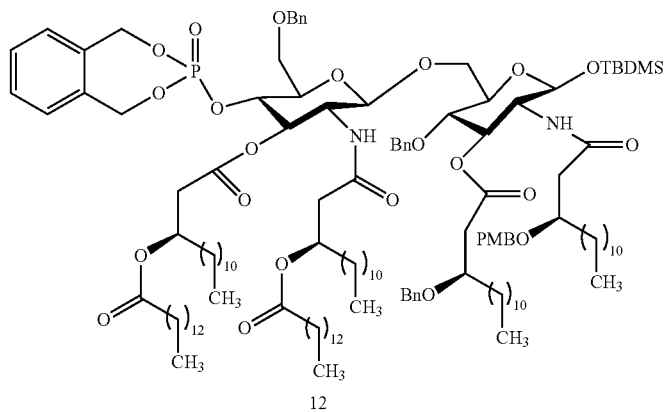

12

To a solution of amine 11 (93 mg, 0.046 mmol) in DCM (10 mL) was added pyridine (21 mg, 0.27 mmol), (R)-3-(4-methoxybenzyloxy)tetradecanoyl chloride (see preparation below, compound 35) (40 mg, 0.12 mmol), and 4-dimethylaminopyridine (DMAP) (1 mg) at room temperature, and the mixture was stirred overnight. The mixture was transferred to a separatory funnel and diluted with diethyl ether (20 mL) and saturated sodium bicarbonate (20 mL). The aqueous layer was extracted with diethyl ether (3×20 mL). The combined organic extracts were dried over sodium sulfate, filtered and concentrated under reduced pressure. The residue was purified by chromatography on silica gel (12 g RediSep column, eluting with a gradient of 0% through 80% ethyl acetate/hexanes over 35 min, 30 mL/min) to give the product 12 (81 mg, 74%) as a colorless liquid. $R_f$=0.34 (hexanes/ethyl acetate, 3/2, v/v). $^1$H NMR (300 MHz, CDCl$_3$) δ 7.34-7.20 (m, 20H), 6.89-6.86 (m, 4H), 6.15 (t, J=9.0 Hz, 1H), 5.57-5.55 (m, 1H), 5.31-4.99 (m, 8H), 4.57-4.44 (m, 11H), 4.06-3.33 (m, 15H), 2.63-2.57 (m, 5H), 2.33-2.27 (m, 9H), 1.57 (m, 8H), 1.27 (broad m, 112H), 0.88-0.82 (m, 27H), 0.08 (s, 3H), 0.04 (s, 3H). HRMS (m/z) (pos) calcd for C$_{139}$H$_{227}$N$_2$O$_{23}$PSi, 2351.62; found, 2352.6343 [M+H]$^+$.

Example 11

LIPID A (13a)

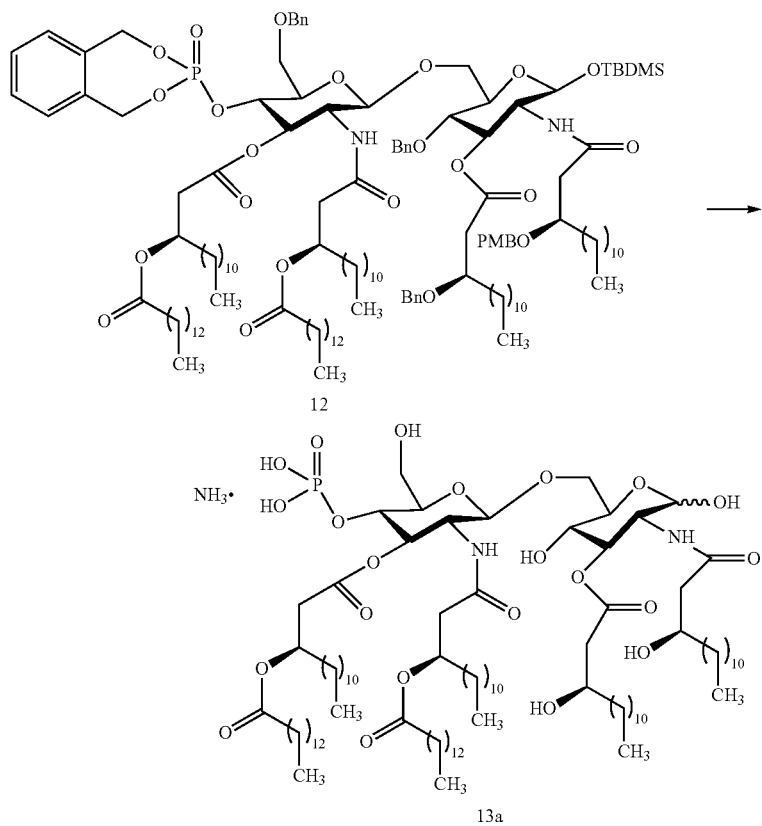

A suspension of 12 (10 mg, 0.0042 mmol) and Pd-black (15.0 mg) in anhydrous THF (5 mL) was shaken under an atmosphere of $H_2$ (50 psi) at room temperature for 30 h. The catalyst was removed by filtration. The residue was washed with THF (2×1 mL). The solution was cooled to −40° C. and neutralized with ammonia in methanol (0.1 mL, 7 M) and concentrated without heating in vacuo. The residue was purified by chromatography (12 g RediSep column, eluting with chloroform/methanol/water 8/2/0.1 for 30 min, 30 mL/min) to afford 13a (4 mg, 54%) as a colorless film. The product was re-dissolved in water and methanol (v/v, 1/1, 2 mL) and lyophilized to obtain the product 13a as a white powder. $^1$H NMR (500 MHz, $CDCl_3$) δ 6.00-5.00 (m, 1H), 4.50-3.50 (m, 2H), 3.00-2.00 (m, 3H), 2.00-1.00 (m, 50H), 0.81 (m, 18H). MS (Multimode, neg) calcd for $C_{96}H_{181}N_2O_{22}P$, 1745.28; found, 1745.0 [M−H]$^-$.

Example 12

LIPID A (13b)

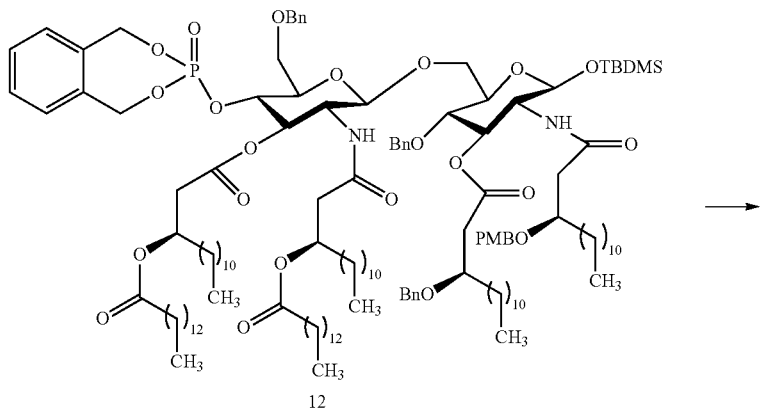

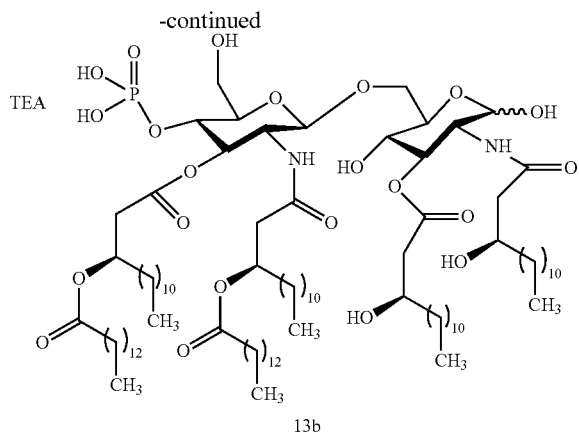

13b

A suspension of 12 (27 mg, 0.011 mmol) and Pd-black (41.0 mg) in anhydrous THF (12 mL) was shaken under an atmosphere of $H_2$ (50 psi) at room temperature for 30 h. The catalyst was removed by filtration. The residue was washed with THF (2×3 mL). The solution was neutralized with triethylamine (TEA) (0.1 mL) and concentrated without heating in vacuo. The combined filtrates were concentrated in vacuo and purified by chromatography on silica (12 g RediSep column, eluting with chloroform/methanol/water 8/2/0.1 30 min, 30 mL/min) to afford 13b (5 mg, 25%) as a colorless film. The product was re-dissolved in water and methanol (v/v. 1/1, 2 mL) and lyophilized to obtain the product 13b as a white powder. $^1$H NMR (500 MHz, CDCl$_3$) δ 5.17 (broad, 2H), 4.23-3.62 (m, 5H), 3.11-3.07 (q, J=2.8 Hz, 2H), 2.51-2.12 (m, 6H), 1.56-1.00 (m, 69H), 0.92-0.84 (m, 18H). MS (Multimode, neg) calcd for $C_{96}H_{181}N_2O_{22}P$, 1745.28; found, 1744.1 [M–H].

Compound 9 (89 mg, 0.12 mmol) was dissolved in anhydrous DCM (3 mL). Trichloroacetonitrile (1.0 mL) was added followed by sodium hydride (1.0 mg, 60% in mineral oil). After 15 min, TLC indicated the presence of 9, so an additional quantity of sodium hydride (1 mg, 60% in mineral oil) was added. After 15 min, TLC indicated that the reaction was complete. The mixture was concentrated under vacuum and loaded onto a $SiO_2$ column which was pretreated with $Et_3N$ and eluted with 50% ethyl acetatelhexanes to provide the trichloroacetimidate intermediate (76.9 mg, 71%) which was used without further purification. A suspension of trichloroacetimidate (76.9 mg, 0.0852 mmol), acceptor 14 (see preparation below) (52.34 mg, 0.1277 mmol), and molecular sieves (4 Å, 500 mg) in DCM (5.0 mL) was stirred at room temperature for 1 h. The mixture was cooled (−60° C.), and TMSOTf (1.54 μL, 0.0851 mmol) was added. After the reaction mixture was stirred for 30 min, it was quenched with solid $NaHCO_3$. The solids were removed by filtration, and the filtrate was concentrated in vacuo. The residue was purified by silica gel column chromatography (hexanes/ethyl acetate, 2:1 (v/v)) to give 15 (55 mg, 40%) as a colorless solid. $^1$H NMR (500 MHz, CD$_3$COCD$_3$) δ 7.86-7.22 (m, 22H), 6.98 (d, J=9.0 Hz, 1H), 5.85 (m, 1H), 5.41 (t, J=9.0 Hz, 1H), 5.38-5.21 (m, 3H), 5.10-5.02 (m, 3H), 4.91 (d, J=11.0 Hz, 2H), 4.72-4.46 (m, 7H), 4.23-4.15 (m. 4H), 3.93-3.80 (m, 4H), 3.69-3.66 (m, 1H), 3.54 (br s, 3H), 3.20 (dd, J$_1$=8.0 Hz, J$_2$=8.0 Hz, 1H), 0.95 (s, 9H), 0.17 (s, 6H); $^{13}$C NMR (125 MHz, CD$_3$COCD$_3$) δ 207.00,

Example 13

TERT-BUTYLDIMETHYLSILYL-6-O-[3-O-ALLY-LOXYCARBONYL-6-O-BENZYL-2-DEOXY-4-O-(1,5-DIHYDRO-3-OXO-3λ$^5$-3H-2,4,3-BENZODI-OXAPHOSPHEPIN-3-YL)-2-(9-FLUORENYLMETHOXYCARBONYLAMINO)-β-D-GLUCOPYRANOSYL]-2-AZIDO-4-O-BENZYL-2-DEOXY-β-D-GLUCOPYRANOSIDE (15)

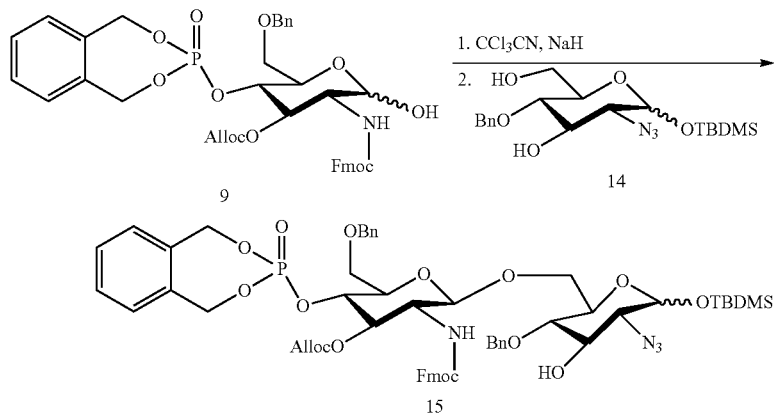

156.61, 155.51, 145.22, 144.82, 142.06, 142.01, 139.98, 139.57, 136.68, 136.62, 133.02, 132.94, 129.85, 129.83, 129.15, 129.05, 128.95, 128.91, 128.82, 128.61, 128.49, 128.41, 128.21, 128.17, 128.0, 127.92, 126.19, 126.09, 125.98, 120.79, 118.60, 118.52, 101.41, 97.57, 78.78, 78.10, 76.84, 75.98, 75.88, 75.43, 75.30, 75.17, 74.70, 74.07, 70.63, 69.76, 69.64, 69.27, 69.15, 69.10, 69.02, 68.97, 67.73, 67.17, 57.29, 54.94, 26.11, 18.51; HR MS (m/z) calcd for $C_{59}H_{69}N_4O_{16}PSi$ $[M+H]^+$, 1149.4293; found, 1149.4238.

Example 14

TERT-BUTYLDIMETHYLSILYL-6-O-{3-O-AL-LYLOXYCARBONYL-6-O-BENZYL-2-DEOXY-4-O-(1,5-DIHYDRO-3-OXO-3λ$^5$-3H-2,4,3-BEN-ZODIOXAPHOSPHEPIN-3-YL)-2-[(R)-3-DODECANOYLOXY-TETRADECANOYLAMINO]-β-D-GLUCOPYRANOSYL}-2-AZIDO-4-O-BENZYL-2-DEOXY-β-D-GLUCOPYRANOSIDE (16)

1,8-Diazabicyclo[5.4.0]undec-7-ene (220 μL, 1.47 mmol) was added dropwise to a solution of 15 (800 mg, 0.696 mmol) in DCM (10 mL). The reaction mixture was stirred at room temperature for 1 h, after which it was concentrated in vacuo. The residue was purified by silica gel column chromatography (DCM/methanol, 100:1 through 100:3 (v/v)) to afford the free amine (648 mg, 99%) as a colorless syrup. $^1$H NMR (500 MHz, CDCl$_3$) δ 7.36-7.17 (m, 14H), 5.96-5.88 (m, 1H), 5.40-5.06 (m, 7H), 4.84-4.50 (m, 9H), 4.21 (d, J=13.5 Hz, 1H), 4.15-4.11 (m, 1H), 3.82 (m, 1H), 3.79-3.42 (m, 5H), 3.34-3.19 (m, 2H), 2.96-2.90 (m, 1H), 2.34 (d, J=4.5 Hz, 1H), 0.90 (s, 9H), 0.13 (s, 6H). HRMS (m/z) calcd for $C_{44}H_{59}N_4O_{14}PSi$ $[M+H]^+$, 927.3613; found, 927.3569.

N,N-Dicyclohexylcarbodiimide (DCC) (230 mg, 1.11 mmol) was added to a stirred solution of (R)-3-dodecanoyl-tetradecanoic acid (see preparation below, compound 40) (381 mg, 0.81 mmol) in DCM (10 mL). After the reaction mixture was stirred for 10 min, the free amine (648 mg, 0.699 mmol) in DCM (10 mL) was added, and stirring was continued for another 12 h. The insoluble materials were removed by filtration, and the residue was washed with DCM (2×2 mL). The combined filtrates were concentrated in vacuo, and the residue was purified by silica gel column chromatography (hexanes/ethyl acetate, 2:1 (v/v)) to give 16 (450 mg, 47%) as a white solid. $^1$H NMR (500 MHz, CDCl$_3$) δ 7.35-7.17 (m, 14H), 5.94-5.86 (m, 2H), 5.47 (t, J=9.0, 10.5 Hz, 1H), 5.37 (d, J=2.5 Hz, 1H), 5.34 (d, J=2.5 Hz, 1H), 5.24 (d, J=13.5 Hz, 1H), 5.13-4.97 (m, 6H), 4.75 (d, J=11.0 Hz, 1H), 4.66-4.49 (m, 7H), 4.00 (d, J=17.0 Hz, 2H), 3.83 (d, J=10.5 Hz, 1H), 3.75-3.56 (m, 4H). 3.49-3.36 (m, 5H), 3.20 (m, 1H), 2.42-2.17 (m, 4H). 1.93 (d, J=11.5 Hz, 1H), 1.70 (m, 2H), 1.23 (br s, 36H), 0.92 (s, 9H), 0.89-0.86 (m, 6H), 0.14 (s, 6H); HRMS (m/z) calcd for $C_{72}H_{111}N_4O_{17}PSi$ $[M+H]^+$, 1363.7529; found. 1363.7487.

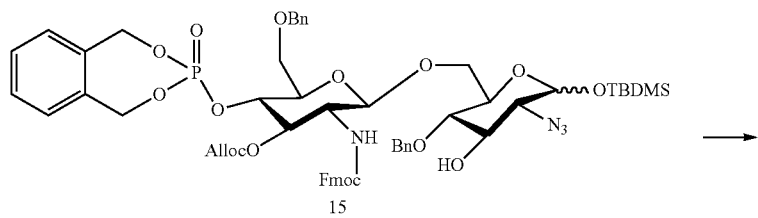

15

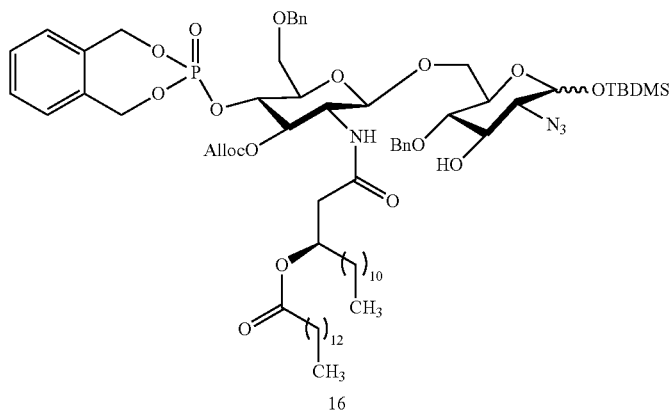

16

Example 15

TERT-BUTYLDIMETHYLSILYL-6-O-{3-O-AL-LYLOXYCARBONYL-6-O-BENZYL-2-DEOXY-4-O-(1,5-DIHYDRO-3-OXO-3λ$^5$-3H-2,4,3-BEN-ZODIOXAPHOSPHEPIN-3-YL)-2-[(R)-3-DODECANOYLOXY-TETRADECANOYLAMINO]-β-D-GLUCOPYRANOSYL}-2-AZIDO-4-O-BENZYL-3-O-[(R)-3-BENZYLOXY-TETRADECANOYL]-2-DEOXY-β-D-GLUCOPYRANOSIDE (17)

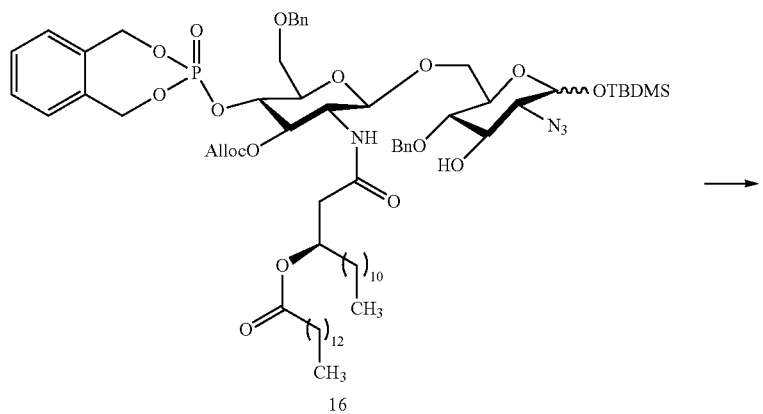

16

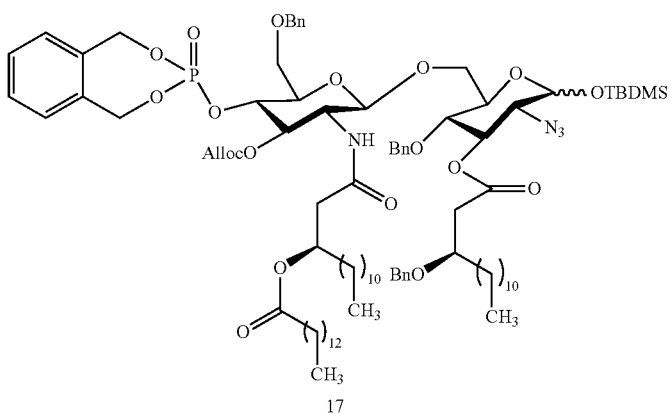

17

A mixture of (R)-3-benzyloxytetradecanoic acid (see preparation below, compound 33) (120 mg, 0.540 mmol) and DCC (171 mg, 0.830 mmol) in DCM (5 mL) was stirred at room temperature for 10 min, and then disaccharide 16 (451 mg, 0.331 mmol) in DCM (5 mL) and DMAP (25 mg, 0.21 mmol) were added. The reaction mixture was stirred at room temperature for 14 h, after which the solids were removed by filtration. The residue was washed with DCM (2×4 mL). The combined filtrates were concentrated in vacuo, and the residue was purified by silica gel column chromatography (hexanes/ethyl acetate, 4:1 (v/v)) to give 17 (540 mg, 97%) as a white solid. $R_f$=0.41 (hexanes/ethyl acetate, 2:1 (v/v)). $^1$H NMR (500 MHz. CDCl$_3$) δ 7.33-7.15 (m, 19H), 5.94-5.85 (m, 2H), 5.47 (t, J=9.5 Hz, 1H), 5.37 (d, J=17.5 Hz, 1H), 5.22 (d, J=10.0 Hz, 1H), 5.10-4.95 (m, 7H), 4.62-4.43 (m, 10H), 4.0-3.96 (m, 3H), 3.90-3.81 (m, 2H). 3.74-3.67 (m, 3H), 3.56-3.42 (m, 6H), 3.33-3.27 (m, 1H), 2.60-2.21 (m, 6H), 1.24 (br s, 54H), 0.91 (s, 9H), 0.87-0.84 (m, 9H), 0.14 (s. 6H). HRMS (m/z) calcd for C$_{93}$H$_{143}$N$_4$O$_{19}$PSi [M+H]$^+$, 1679.9931; found, 1679.9934.

Example 16

TERT-BUTYLDIMETHYLSILYL-6-O-{6-O-BEN-ZYL-2-DEOXY-4-O-(1,5-DIHYDRO-3-OXO-3λ$^5$-3H-2,4,3-BENZODIOXAPHOSPHEPIN-3-YL)-2-[(R)-3-DODECANOYLOXY-TETRADECANOYLAMINO]-β-D-GLUCOPYRANOSYL}-2-AZIDO-4-O-BENZYL-3-O-[(R)-3-BENZYLOXY-TETRADECANOYL]-2-DEOXY-β-D-GLUCOPYRANOSIDE (18)

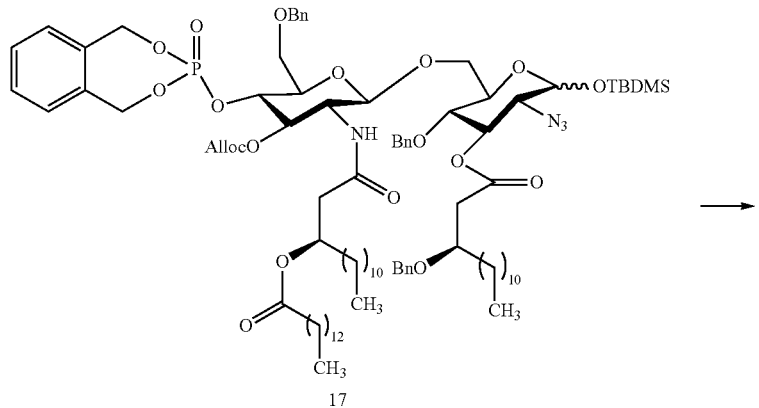

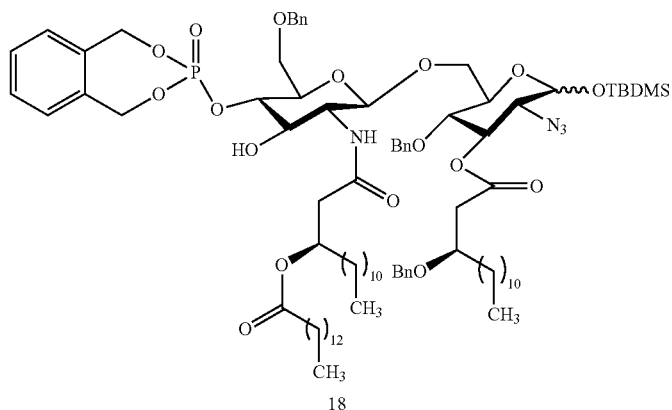

Tetrakis(triphenylphosphine)palladium (228 mg, 0.198 mmol) was added to a solution of 17 (1.66 g, 0.980 mmol), n-BuNH$_2$ (0.19 mL, 1.97 mmol), and HCOOH (74.5 μL, 1.98 mmol) in THF (20 mL). After the reaction mixture was stirred at room temperature for 20 min, it was diluted with DCM (40 mL), and washed successively with water (40 mL), saturated aqueous NaHCO$_3$ (2×40 mL), and brine (40 mL). The organic phase was dried (MgSO$_4$) and filtered. The filtrate was concentrated in vacuo. The residue was purified by silica gel column chromatography (hexanes:ethyl acetate, 4:3 (v/v)) to give compound 18 (1.43 g, 91%). $R_f$=0.5 (hexanes/ethyl acetate, 1:1 (v/v)). $^1$H NMR (500 MHz, CDCl$_3$) δ 7.33-7.11 (m, 19H), 6.2 (d, J=7.5 Hz, 1H), 5.46 (t, J=9.0 Hz, 1H), 5.04-4.90 (m, 9H), 4.55-4.38 (m, 8H), 3.92 (d, J=10.0 Hz, 1H), 3.84-3.76 (m, 1H), 3.75-3.7 (m, 4H), 3.53-3.44 (m, 2H), 3.43-3.32 (m, 2H), 3.25-3.20 (m, 1H), 2.61-2.10 (m, 12H). 1.23 (br s, 54H), 0.90 (s, 9H), 0.88-0.84 (m, 9H), 0.12 (s, 6H). HRMS (m/z) calcd for C$_{89}$H$_{139}$N$_4$O$_{17}$PSi [M+H]$^+$, 1595.972; found, 1595.9713.

Example 17

TERT-BUTYLDIMETHYLSIYL-6-O-{6-O-BEN-ZYL-2-DEOXY-4-O-(1,5-DIHYDRO-3-OXO-3λ⁵-3H-2,4,3-BENZODIOXAPHOSPHEPIN-3YL)-2-[(R)-3-DODECANOYLOXY-TETRADECANOYLAMINO)-3-O-[(R)-3-(P-METHOXY)BENZYLOXYTETRADECANOYL]-β-D-GLUCOPYRANOSYL}-2-AZIDO-4-O-BENZYL-3-O-[(R)-3-BENZYLOXY-TETRADECANOYL]-2-DEOXY-β-D-GLUCOPYRANOSIDE (19)

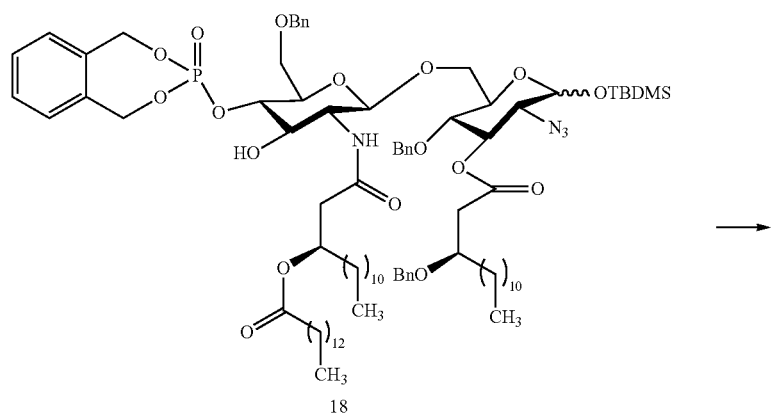

18

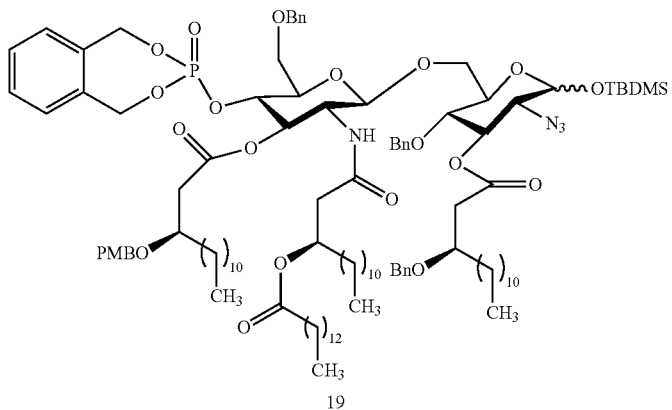

19

A solution of (R)-3-(p-meihoxy)benzyloxy-tetradecanoic acid (see preparation below, compound 34, 424 mg, 1.16 mmol) and DCC (369 mg, 1.79 mmol) in DCM (15 mL) was stirred at room temperature for 10 min, and the alcohol 18 (1.43 g, 0.896 mmol) in DCM (10 mL) and DMAP (54.72 mg, 0.4479 mmol) were added. The reaction mixture was stirred for another 14 h, after which the solids were removed by filtration and washed with DCM (2×5 mL). The combined filtrates were concentrated in vacuo. The residue was purified by silica gel column chromatography (hexanes/ethyl acetate, 4:1 (v/v)) to afford 19 (1.15 g, 66%) as a white solid. $R_f$=0.46 (hexanesiethyl acetate, 2:1 (v/v)). $^1$H NMR (500 MHz, CDCl$_3$) δ 7.38-6.79 (m, 23H). 5.73 (d, J=8.0 Hz, 1H), 5.55 (t, J=9.5 Hz, 1H), 5.20-4.88 (m, 8H), 4.66-4.47 (m, 12H), 4.33 (d, J=12.5 Hz, 1H), 4.0-3.66 (m, 12H), 3.61-3.40 (m, 5H), 3.36-3.27 (m, 3H), 2.67 (d, J=6.0 Hz, 2H). 2.60-2.22 (m, 6H), 1.27 (br s, 72H), 0.93 (s, 9H), 0.92-0.87 (m, 12H), 0.16 (s, 6H). HRMS (m/z) calcd for C$_{111}$H$_{173}$N$_4$O$_{20}$PSi [M+H]$^+$, 1942.2228; found, 1942.2289.

Example 18

TERT-BUTYLDIMETHYLSIYL-6-O-{6-O-BEN-ZYL-2-DEOXY-4-O-(1,5-DIHYDRO-3-OXO-3λ$^5$-3H-2,4,3-BENZODIOXAPHOSPHEPIN-3YL)-2-[(R)-3-DODECANOYLOXY-TETRADECANOYLAMINO]-3-O-[(R)-3-TETRADECANOYLOXY-TETRADECANOYL]-β-D-GLUCOPYRANOSYL}-2-AZIDO-4-O-BENZYL-3-O-[(R)-3-BENZYLOXY-TETRADECANOYL]-2-DEOXY-β-D-GLUCOPYRANOSIDE (10)

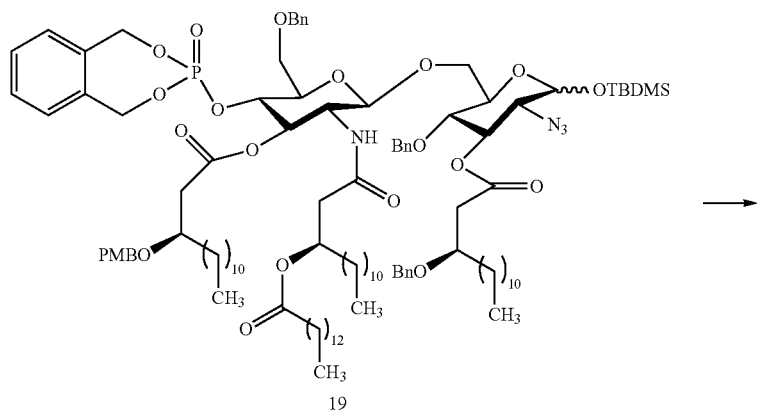

19

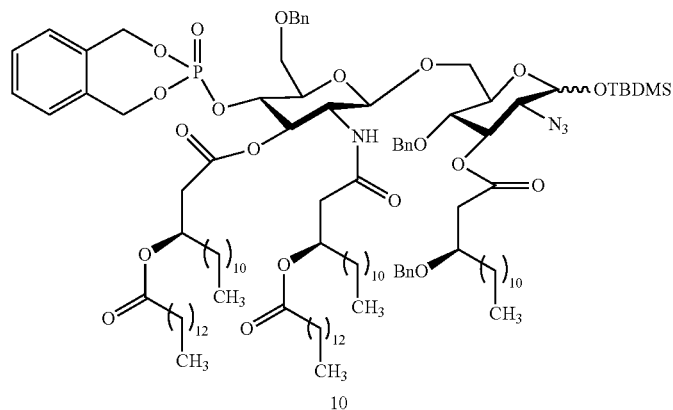

10

To a stirred solution of 19 (1.15 g, 0.592 mmol) in a mixture of DCM and H$_2$O (11 mL, 10:1 (v/v)) was added 2,3-Dichloro-5,6-dicyano-1,4-benzoquinone (DDQ) (202 mg, 0.890 mmol). The reaction mixture was stirred at room temperature for 1 h, after which it was diluted with DCM. The mixture was washed with brine (20 mL), dried (MgSO$_4$), and concentrated in vacuo. The residue was purified by silica gel column chromatography (hexanesi-ethyl acetate, 3:1 (v/v)) to give the alcohol as a colorless syrup (1.01 g, 94%). R$_f$=0.50 (hexanes/ethyl acetate, 5:3 (v/v)). Myristoyl chloride (0.74 mL, 2.7 mmol) was added to a solution of the alcohol (1.01 g, 0.554 mmol), and pyridine (0.35 mL, 4.33 mmol) in DCM (20 mL). After the reaction mixture was stirred at room temperature for 12 h, it was diluted with DCM and washed with saturated aqueous NaHCO$_3$ (2×40 mL) and brine (40 mL). The organic phase was dried (MgSO$_4$) and filtered. The filtrate was concentrated in vacuo. The residue was purified by silica gel column chromatography (hexanes/ethyl acetate, 4:1 (v/v)) to afford 10 (680 mg, 57%) as a white solid. R$_f$=0.46 (hexanes/ethyl acetate, 5:2 (v/v)). $^1$H NMR (500 MHz, CDCl$_3$) δ 7.37-7.24 (m, 19H), 6.23 (d, J=7.5 Hz, 1H), 5.58 (t, J$_1$=9.5 Hz, 1H), 5.32-5.27 (m, 1H), 5.16-4.99 (m, 6H), 4.78-4.44 (m, 7H), 4.03 (d. J=10.5 Hz, 1H), 3.99-3.20 (m, 10H), 2.65-2.21 (m, 10H), 1.61-1.51 (m, 10H), 1.27 (br s, 94H), 1.21 (br s, 25H), 0.12 (s, 6H).

Example 19

TERT-BUTYLDIMETHYLSILYL-6-O-{3-O-AL-LYLOXYCARBONYL-6-O-BENZYL-2-DEOXY-4-O-(1,5-DIHYDRO-3-OXO-3λ⁵-3H-2,4,3-BEN-ZODIOXAPHOSPHEPIN-3-YL)-2-[(R)-3-DECANOYLOXY-TETRADECANOYLAMINO]-5-D-GLUCOPYRANOSYL}-2-AZIDO-4-O-BENZYL-2-DEOXY-β-D-GLUCOPYRANOSIDE (20)

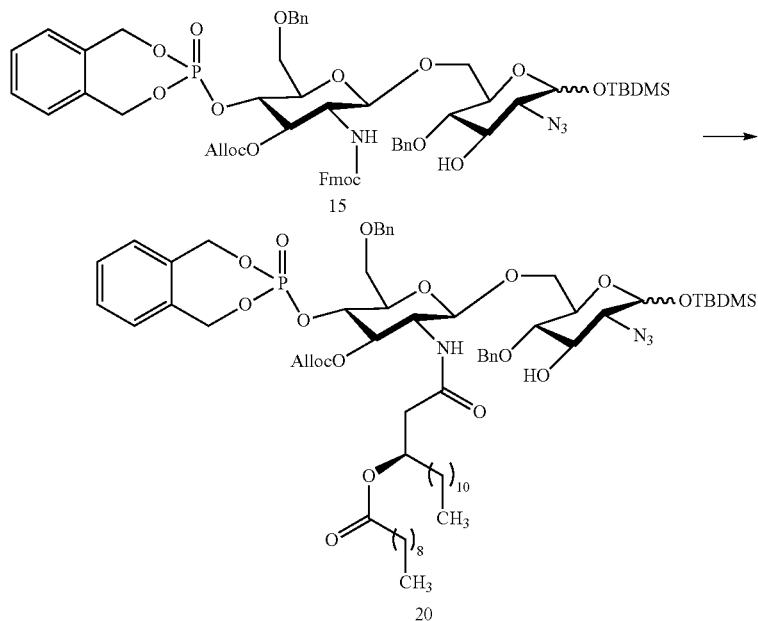

Compound 15 (1.23 g, 1.07 mmol) was acylated in a manner similar to the synthesis of compound 16 (Example 14) using (DCC, 430 mg, 2.08 mmol), required lipid (Compound 40, Example 36, 630 mg, 1.59 mmol), and triethylamine (161 mg, 1.59 mmol) to provide 20 (1.05 g, 81%) as a colorless oil. $^1$H NMR (500 MHz, CDCl$_3$) δ 7.35-7.17 (m, 14H), 5.91-5.86 (m, 2H), 5.47 (t, J=9.0, 10.5 Hz, 1H), 5.34 (d, J=17 Hz, 1H), 5.24 (d, J=10.5 Hz, 1H), 5.10-4.98 (m, 8H), 4.75 (d, J=11.5 Hz, 1H), 4.66-4.49 (m, 8H), 4.00 (d, J=11.0 Hz, 2H), 3.83 (d, J=11.0 Hz, 1H), 3.75-3.69 (m, 2H), 3.49-3.36 (m, 4H), 3.20 (m. 1H), 2.40-2.26 (m, 4H), 1.24 (br s, 32H), 0.92 (s, 9H), 0.89-0.86 (m, 6H), 0.14 (s, 6H); MS (Multimode, pos) m/z=1307 [M+H]$^+$.

Example 20

TERT-BUTYLDIMETHYLSILYL-6-O-{3-O-AL-LYLOXYCARBONYL-6-O-BENZYL-2-DEOXY-4-O-(1,5-DIHYDRO-3-OXO-3λ⁵-3H-2,4,3-BEN-ZODIOXAPHOSPHEPIN-3-YL)-2-[(R)-3-DECANOYLOXY-TETRADECANOYLAMINO]-β-D-GLUCOPYRANOSYL}-2-AZIDO-4-O-BENZYL-3-O-[(3-BENZYLOXY-TETRADECANOYL]-2-DEOXY-β-D-GLUCOPYRANOSIDE (21)

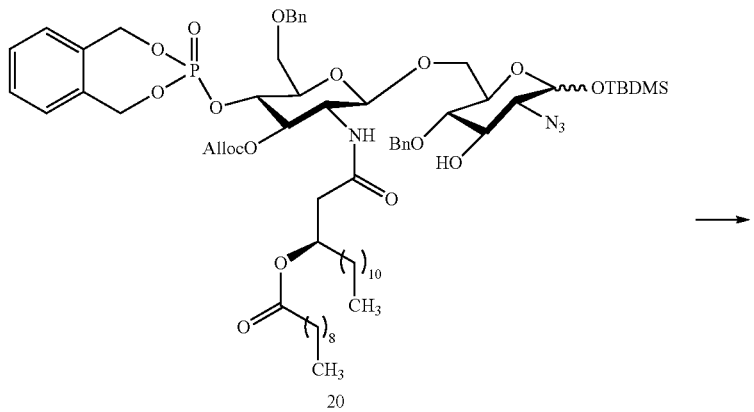

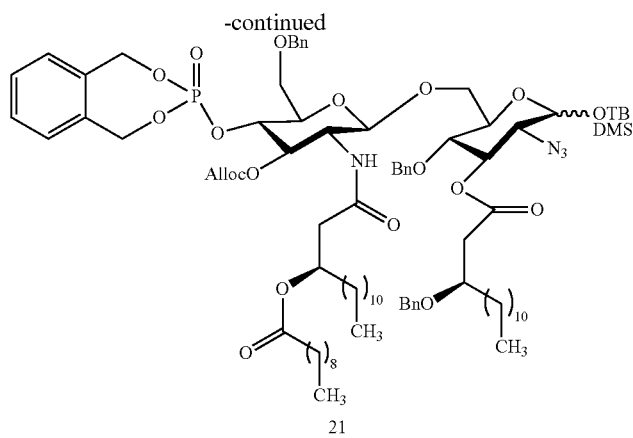

Compound 20 (1.43 g, 1.18 mmol) was acylated in a manner similar to the synthesis of compound 17 (Example 15) using (DCC, 453 mg, 2.20 mmol), required lipid (477 mg, 1.43 mmol), and N,N-dimethyl-4-aminopyridine (67 mg, 0.548 mmol) to provide 21 (1.60 g, 83%) as a colorless oil. $^1$H NMR (500 MHz, CDCl$_3$) δ 7.33-7.15 (m, 19H), 5.94-5.85 (m, 2H), 5.48 (t, J=9.0 Hz, 1H), 5.34 (d, J=17.5 Hz, 1H), 5.22 (d, J=10.0 Hz, 1H), 5.12-4.96 (m, 7H), 4.63-4.46 (m, 11H), 3.97 (d, J=10.5 Hz, 1H), 3.89-3.85 (m, 2H), 3.74-3.68 (m, 3H), 3.55-3.52 (m, 2H), 3.47-3.41 (m, 1H), 3.28 (m, 1H), 2.61-2.22 (m, 8H), 1.59-1.52 (m, 6H), 1.98 (m, 2H), 1.23 (br s, 44H), 0.90 (s, 9H), 0.88-0.84 (m, 9H), 0.12 (s, 6H); MS (Multimode, pos) m/z=1625 [M+H]$^+$.

Example 21

TERT-BUTYLDIMETHYLSILYL-6-O-{6-O-BEN-ZYL-2-DEOXY-4-O-(1,5-DIHYDRO-3-OXO-3λ$^5$-3H-2,4,3-BENZODIOXAPHOSPHEPIN-3-YL)-2-[(R)-3-DODECANOYLOXY-TETRADECANOYLAMINO]-β-D-GLUCOPYRANOSYL}-2-AZIDO-4-O-BENZYL-3-O-[(R)-3-BENZYLOXY-TETRADECANOYL]-2-DEOXY-β-D-GLUCOPYRANOSIDE (22)

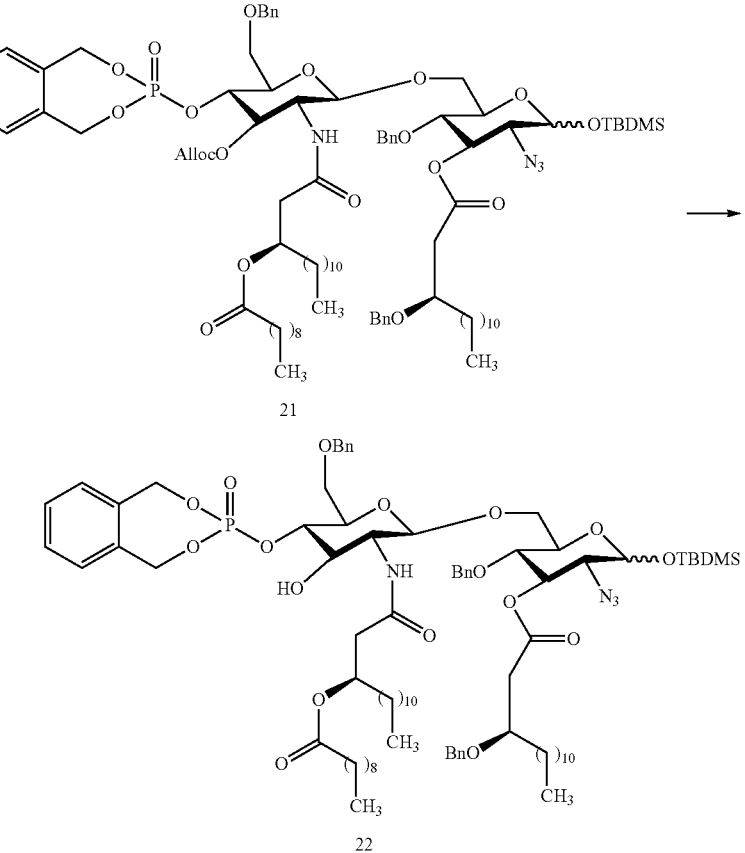

Compound 21 (1.60 g, 0.985 mmol) was reacted in a manner analagous to the synthesis of compound 18 (Example 16). Accordingly, tetrakis(triphenylphosphine)palladium, (227 mg, 0.196 mmol), formic acid (74 μL, 1.97 mmol), and n-butylamine (144 mg, 1.97 mmol) to provide 22 (1.25 g, 82%) as a yellow solid. $^1$H NMR (500 MHz, CDCl$_3$) δ 7.33-7.15 (m, 19H), 6.20 (d, J=7.5 Hz, 1H), 5.38-4.95 (m, 6H), 4.86 (d, J=8.0 Hz, 1H), 4.60-4.46 (m, 10H), 3.97-3.71 (m, 8H), 3.68-3.48 (m, 5H), 3.31-3.27 (m, 3H), 2.62-2.55 (m, 2H), 2.50-2.42 (m, 3H), 2.40-2.22 (m, 5H), 1.23 (br s, 44H), 0.90 (s, 9H), 0.88-0.84 (m, 9H). 0.12 (s, 6H); MS (Multimode, pos) m/z=1539 [M+H]$^+$.

Example 22

TERT-BUTYLDIMETHYLSILYL-6-O-{6-BENZYL-2-DEOXY-4-O-(1,5-DIHYDRO-3-OXO-3λ$^5$-3H-2,4,3-BENZODIOXAPHOSPHEPIN-3-YL)-2-[(R)-3-DECANOYLOXY-TETRADECANOYLAMINO]-3-O-[(R)-3-(P-METHOXY)BENZYLOXYTETRADECANOYL]-β-D-GLUCOPYRANOSYL}-2-AZIDO-4-O-BENZYL-3-O-[(R)-3-BENZYLOXY-TETRADECANOYL]-2-DEOXY-β-D-GLUCOPYRANOSIDE (23)

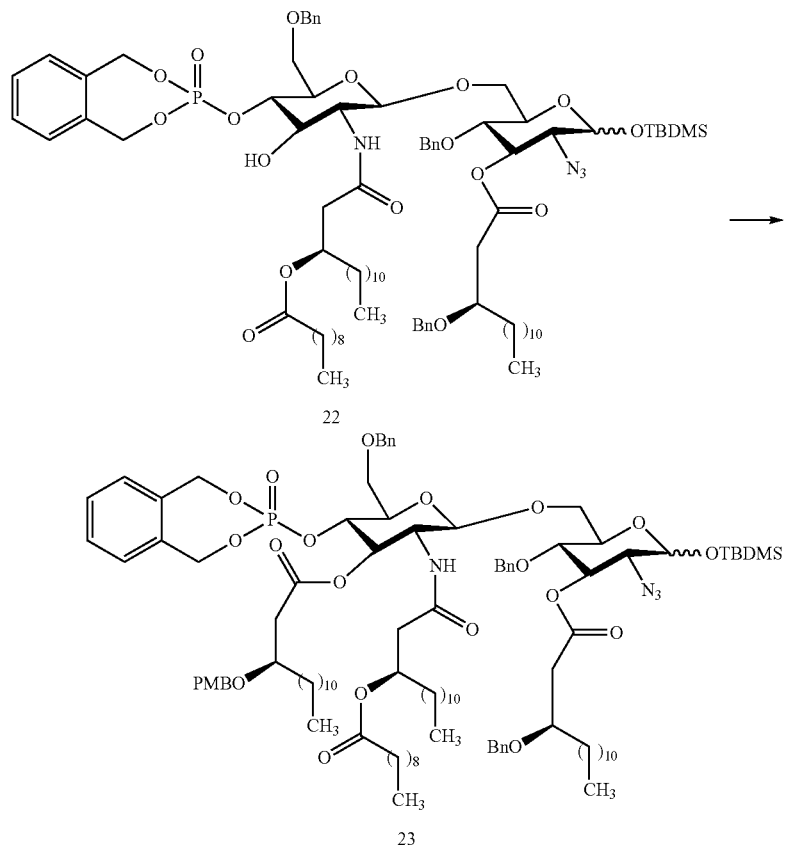

Compound 22 (1.25 g, 0.811 mmol) was acylated in a manner similar to the synthesis of compound 19 (Example 17) using (DCC, 335 mg, 1.62 mmol), required lipid (Compound 34, Example 32, 386 mg, 1.06 mmol), and N,N-dimethyl-4-aminopyridine (50 mg, 0.41 mmol) to provide 23 (440 mg, 29%) as a colorless oil. $^1$H NMR (500 MHz, CDCl$_3$) δ 7.38-6.79 (m, 23H), 5.71 (d, J=7.5 Hz. 1H), 5.55 (t, J=9.5 Hz, 1H), 5.06-4.85 (m. 9H), 4.66-4.45 (m, 12H), 3.97 (d, J=11.0 Hz, 1H), 3.90-3.69 (m, 9H), 3.60-3.55 (m, 3H), 3.37-3.29 (m, 2H), 2.65 (d, J=7.5 Hz, 2H), 2.61-2.55 (m, 1H), 2.48-2.42 (m, 1H), 2.35-2.21 (m, 3H), 2.11-2.05 (m, 1H), 1.62-1.59 (m, 8H), 1.27 (br s, 62H), 0.93 (s, 9H), 0.92-0.87 (m, 12H), 0.16 (s, 6H); MS (Multimode, pos) m/z=1886 [M+H]$^+$.

Example 23

TERT-BUTYLDIMETHYLSILYL-6-O-{6-O-BEN-ZYL-2-DEOXY-4-O-(1,5-DIHYDRO-3-OXO-3λ$^5$-3H-2,4,3-BENZODIOXAPHOSPHEPIN-3-YL)-2-[(R)-3-DECANOYLOXY-TETRADECANOYLAMINO]-3-O-[(R)-3-DECANOYLOXY-TETRADECANOYL]-β-D-GLUCOPYRANOSYL}-2-AZIDO-4-O-BENZYL-3-O-[(R)-BENZYLOXY-TETRADECANOYL]-2-DEOXY-β-D-GLUCOPYRANOSIDE (24)

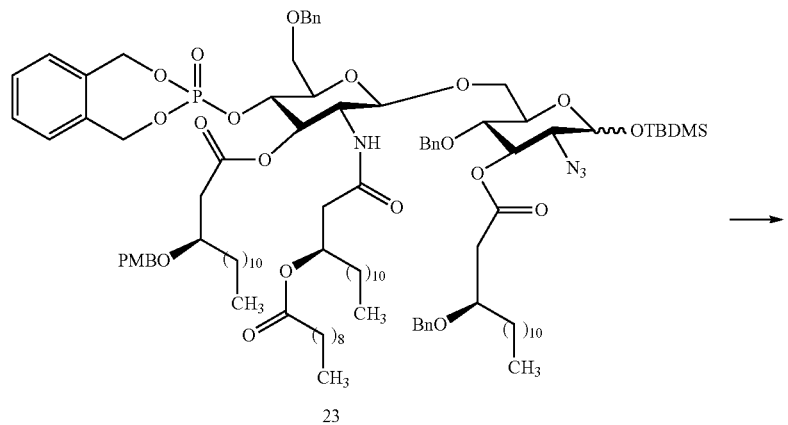

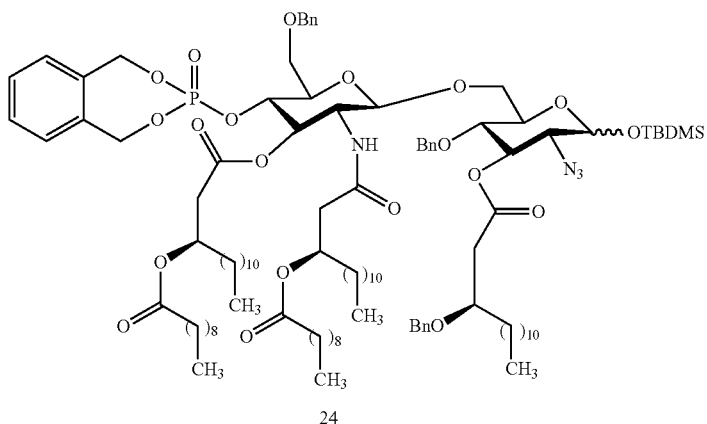

Compound 23 (446 mg, 0.236 mmol) was first deprotected using DDQ (80 mg, 0.35 mmol) following the procedure for intermediate 10 for Target A. This intermediate (343 mg, 0.194 mmol) was then acylated in a manner similar to the synthesis of compound 10 for Target A using decanoyl chloride (185 mg, 0.970 mmol) and pyridine (123 mg, 1.55 mmol) to provide 24 (343 mg, 76%) as a colorless oil. $^1$H NMR (500 MHz, CDCl$_3$) δ 7.39-7.22 (m, 14H), 6.15 (d, J=7.5 Hz, 1H), 5.54 (t, J=9.5 Hz, 1H), 5.28-5.24 (m. 1H), 5.14-4.96 (m, 8H), 4.60-4.45 (m, 10H), 3.99 (d, J=10.5 Hz, 1H), 3.90-3.85 (m, 1H), 3.80-3.65 (m, 4H), 3.55 (m, 3H), 3.46-3.39 (m, 1H), 3.32-3.27 (m, 1H), 2.66-2.53 (m, 3H), 2.46-2.41 (m, 1H), 2.35-2.18 (m, 7H), 1.61-1.51 (m, 10H), 1.26 (br s, 78H), 0.95 (s, 9H), 0.92-0.90 (m, 15H), 0.19 (5, 3H), 0.18 (s, 3H).

Example 24

TERT-BUTYLDIMETHYLSILYL-6-O-{6-O-BEN-ZYL-2-DEOXY-4-O-(1,5-DIHYDRO-3-OXO-3λ$^5$-3H-2,4,3-BENZODIOXAPHOSPHEPIN-3-YL)-2-[(R)-3-DECANOYLOXY-TETRADECANOYLAMINO]-3-O-[(R)-3-DECANOYLOXY-TETRADECANOYL]-β-D-GLUCOPYRANOSYL}-4-O-BENZYL-3-O-[(R)-3-BENZYLOXYTETRADECANOYL]-2-[(R)-3-BENZYLOXY-TETRADECANOYLAMINO]-2-DEOXY-β-D-GLUCOPYRANOSIDE (25)

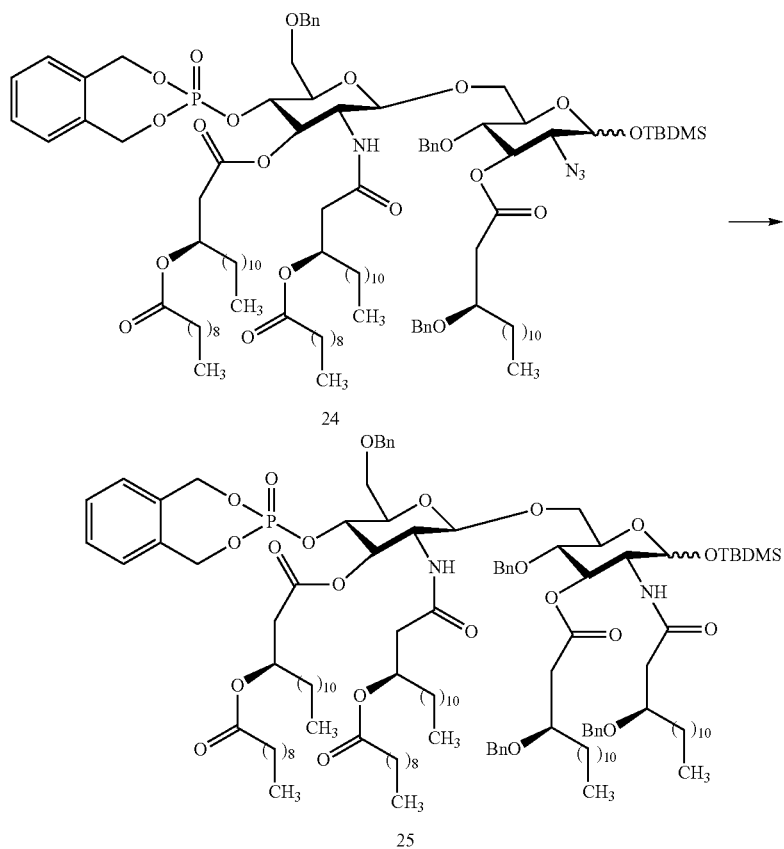

A suspension of 24 (296 mg, 0.154 mmol), zinc (100 mg, 1.52 mmol), and acetic acid (53 μL, 0.93 mmol) in DCM (10 mL) was stirred at room temperature for 12 h, after which it was diluted with ethyl acetate (25 mL). The solids were removed by filtration and washed with ethyl acetate (2×25 mL), and the combined filtrates were washed with saturated aqueous NaHCO$_3$ (2×100 mL) and brine (200 mL). The organic phase was dried (Na$_2$SO$_4$) and filtered. The filtrate was concentrated in vacuo. The residue was purified by silica gel column chromatography (hexanes/ethyl acetate, 2.5:1 (v/v)) to afford the amine as a pale yellow syrup (245 mg, 84%). $^1$H NMR (500 MHz, CDCl$_3$) δ 7.39-7.22 (m, 14H), 6.15 (d, J=7.5 Hz, 1H), 5.54 (t, J=9.5 Hz, 1H), 5.29-5.23 (m, 1H), 5.13-4.93 (m, 8H). 4.62-4.30 (m, 9H), 4.00 (d, J=10.5 Hz, 1H), 3.88-3.65 (m, 6H), 3.56-3.53 (m, 2H), 3.46-3.41 (m, 1H), 2.66-2.58 (m, 4H), 2.54-2.45 (m, 2H), 2.35-2.17 (m, 7H), 1.64-1.42 (m, 12H), 1.26 (br s, 78H), 0.87 (s, 24H), 0.13 (s, 6H).

The amine was added to a stirred solution of (R)-3-benzyloxytetradecanoyl chloride (228 mg, 0.646 mmol), DMAP (15.79 mg, 0.1292 mmol), and pyridine (83 μL, 1.0 mmol) in DCM (5.0 mL). The reaction mixture was stirred for 14 h. The mixture was diluted with CH$_2$Cl$_2$ and was washed with saturated NaHCO$_3$/brine dried under Na$_2$SO$_4$ and concentrated under vacuum. The residue was purified by silica gel TLC chromatography (hexanes/ethyl acetate, 3.5:1 (v/v)) to give 25 (450 mg, >100%) as a white solid. R$_f$=0.54 (hexanes/ethyl acetate, 2:1 (v/v)). $^1$H NMR (500 MHz, CDCl$_3$) δ 7.39-7.22 (m, 19H), 6.14-6.10 (m, 2H), 5.57 (I, J=9.5 Hz, 1H), 5.29-5.24 (m, 1H), 5.13-4.93 (m, 7H). 4.61-4.41 (m, 10H), 4.00 (d, J=10.5 Hz, 1H), 3.89-3.79 (m, 8H), 3.72-3.66 (m, 4H), 3.57-3.35 (m, 3H), 2.73-2.57 (m, 10H), 2.39-2.15 (m, 10H), 1.71-1.64 (m, 7H), 1.26 (br s, 93H), 0.88 (s, 24H), 0.83 (s, 9H).

Example 25

6-O-{6-O-BENZYL-2-DEOXY-4-O-(1,5-DI-HYDRO-3-OXO-3λ$^5$-3H-2,4,3-BENZODIOXA-PHOSPHEPIN-3-YL)-2-[(R)-3-DECANOYLOXY-TETRADECANOYLAMINO]-3-O-[(R)-3-DECANOYLOXY-TETRADECANYL]-β-D-GLUCOPYRANOSYL}-4-O-BENZYL-3-O-[(R)-3-BENZYLOXY-TETRADECANOYL]-2-[(R)-3-BENZYLOXY-TETRADECANOYLAMINO]-2-DEOXY-α-D-GLUCOPYRANOSE (26)

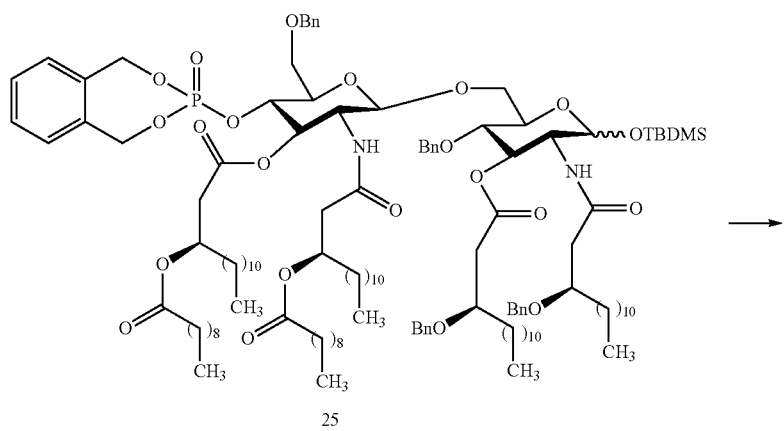

25

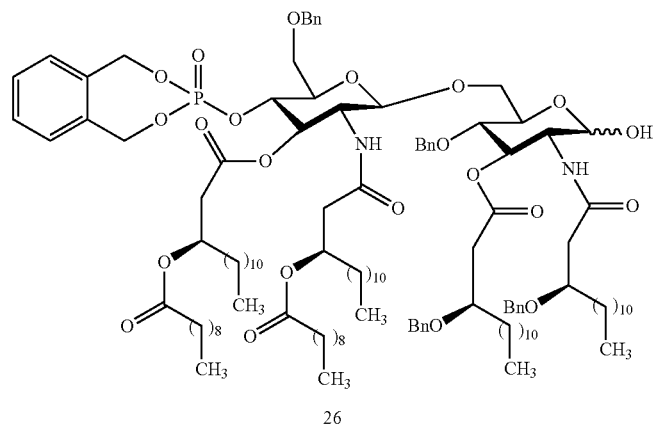

26

Hydrogen fluoride/pyridine (1.12 mL, 43.1 mmol) was added dropwise to a stirred solution of 25 (450 mg, 0.204 mmol) in THF (5 mL). The reaction mixture was stirred at room temperature for 14 h. The mixture was diluted with ethyl acetate (100 mL) and washed with saturated aqueous NaHCO$_3$ (2×80 mL) and brine. The organic phase was dried (Na$_2$SO$_4$) and filtered. The filtrate was concentrated in vacua. The residue was purified by silica gel column chromatography (hexanes/ethyl acetate, 3:1 through 4:3 (v/v)) to give 26 (180 mg, 42%) as a white solid. $^1$H NMR (500 MHz, CDCl$_3$) δ 7.39-7.19 (m, 19H), 6.31 (d, J=7.0 Hz. 1H), 6.24 (d, J=9.5 Hz, 1H), 5.57-5.48 (m, 2H), 5.40 (t, J=9.5 Hz, 1H), 5.28-5.21 (m, 1H), 5.14-4.96 (m, 8H), 4.68-4.41 (m, 12H). 4.23-4.19 (m, 1H), 4.13-4.06 (m, 1H), 3.94-3.66 (m, 9H), 3.38-3.28 (m, 2H), 2.67-2.58 (m, 3H), 2.44-2.20 (m, 11H), 1.58 (br s, 12H), 1.26 (br s, 93H), 0.91-0.81 (m, 18H).

Example 26

(3R)-((2R,3S,4R,5S)-3-((R)-3-(DECANOYLOXY)
TETRADECANAMIDO)-2-(((3S,4R,5S)-3,6-DIHY-
DROXY-5-((R)-3-HYDROXYTETRADECANA-
MIDO)-4-((R)-3-
HYDROXYTETRADECANOYLOXY)
TETRAHYDRO-2H-PYRAN-2-Y)ETHOXY)-6-
(HYDROXYMETHYL)-5-(PHOSPHONOOXY)
TETRAHYDRO-2H-PYRAN-4-YL)
3-(DECANOYLOXY)TETRADECANOATE (IX)

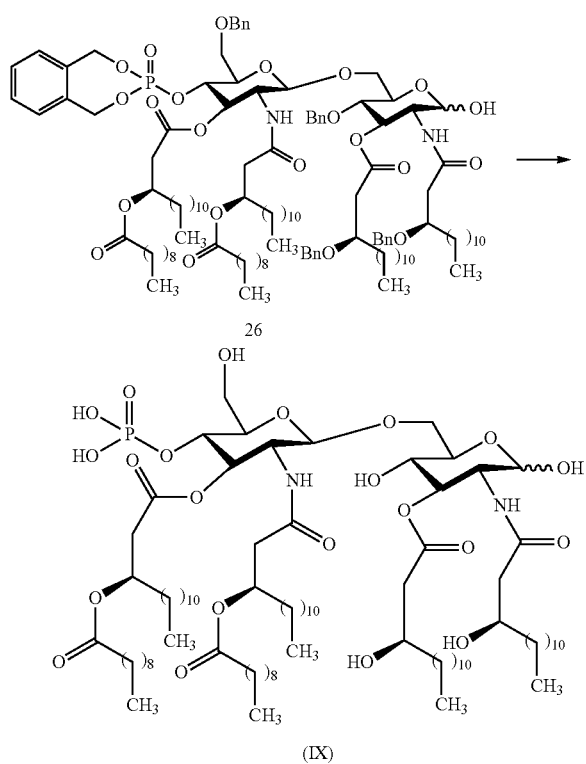

Compound 26 (180 mg, 0.0858 mmol) was dissolved in anhydrous THF (15 mL). Palladium black (0.225 g) was added to the mixture and was hydrogenated under 50 psi hydrogen atmosphere overnight. The mixture was filtered through a bed of diatomaceous earth. The filtrate was cooled to −40° C. and a solution of ammonia in methanol (1.8 mL, 4 M) was added. The mixture was concentrated under vacuum without heating. The residue was purified by silica gel chromatography eluting with a mixture of chloroform/methanol/water, 80:20:1 (v/v) to give the desired compound (IX) (102 mg, 73%). Analysis by TLC and $^1$H NMR showed the presence of grease and a faint close running spot (TLC in CH$_2$Cl$_2$/CMA, 4:1). The residue was subjected to chromatography (12 g RediSep column, eluted with a gradient of isocratic CH$_2$Cl$_2$ for 5 column volumes (CVs), a gradient through 25% CMA over 10 CVs, isocratic for 10 CVs, a gradient though 100% CMA over 10 CVs, isocratic at 100% CMA for 10 CVs, 20 mL/min) to give the desired product (57 mg, 25%). TLC analysis of the combined and concentrated fractions still indicated a very small amount of impurity running just above the desired product. The residue was re-purified by silica gel chromatography (two 12 g RediSep columns in series, same gradient as above) to provide 8.9 mg of the desired product pure by TLC and 11.9 mg of slightly impure product after dissolving in methanol/water/chloroform and freeze-drying. Total yield (20.8 mg, 14%) as an off white solid. R$_f$=0.40 CMA. $^1$H NMR (500 MHz, CDCl$_3$) δ 5.40-5.30 (br s, 2H), 4.10-4.00 (m, 4H), 3.70-3.60 (m, 4H), 2.83-2.76 (m, 1H), 2.75-2.20 (m, 13H), 2.10-1.90 (broad, 9H), 1.40-1.00 (broad, 106H), 0.90-0.70 (broad, 18H). MS (Multimode, Neg) m/z=1632 [M−H]$^-$.

Example 27

METHYL 3-OXOTETRADECANOATE (29)

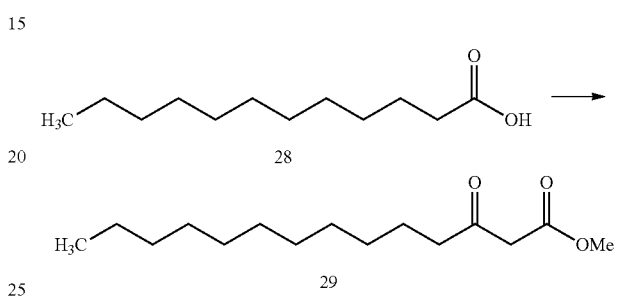

To a suspension of magnesium ethoxide (10.82 g, 94.61 mmol) in 1,4-dioxane (100 mL) was added methyl hydrogen malonate (25.0 g, 189 mmol) in 1,4-dioxane (100 mL). The resulting slurry was stirred overnight. The mixture was concentrated in vacuo. In a separate flask, lauric acid (28, 20.85 g, 104.1 mmol) was dissolved in 1,4-dioxane (50 mL) and a solution of CDI (16.88 g, 104.1 mmol) in 1,4-dioxane (150 mL) was added at room temperature. The resulting solution was stirred overnight. The mixture was then transferred to the methyl magnesium malonate flask. The resulting suspension was refluxed overnight. The mixture was concentrated in vacuo. The residue was redissolved in DCM (300 mL) and filtered through a silica plug (10 g). The solvent was evaporated under reduced pressure. The residue was purified by silica gel column chromatography (360 g RediSep column, eluting with a gradient of 0% through 30% ethyl acetate/hexanes over 80 min, 100 mL/min) to afford product 29 (17 g, 61%) as a pale yellow syrup.

Example 28

(R)-METHYL 3-HYDROXYTETRADECANOATE (30)

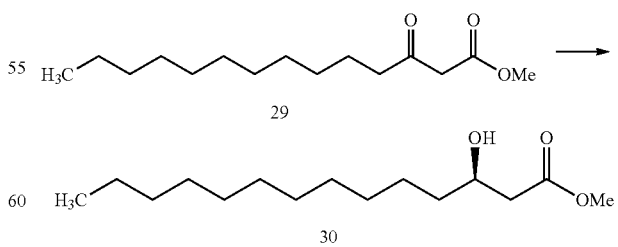

A slurry of methyl 3-oxotetradecanoate (29, 29.0 g, 113 mmol) in methanol (120 mL) was purged in a 300 mL high pressure reactor glass sleeve with N$_2$ for 10 minutes. Dichloro-R-2,2'-bis(diphenylphosphino)-1,1'-binaphthyl ruthenium (897 mg, 1.10 mmol) was added. The mixture was placed in a Parr 5500 series compact reactor. The reactor was charged with H$_2$ (60 psi) and vented 3 times. The reactor was charged with H$_2$ (60 psi) and stirred (1200 rpm) and heated to 50° C. for 20 h. The reactor was cooled to room temperature, and the resulting orange solution was concentrated in vacuo. The residue was purified by silica gel chromatography (120 g RediSep column, eluting with a gradient of 0% through 40% ethyl acetate/hexanes over 60 min, 85 ml/min) to provide product 30 (28.5 g, 97% yield) as a white solid.

Example 29

(R)-METHYL 3-(BENZYLOXY)TETRADECANOATE (31)

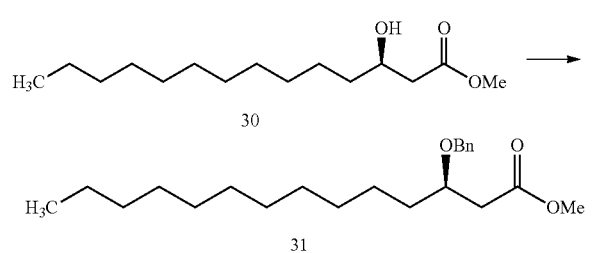

To a solution of compound 30 (2.8 g, 10.83 mmol) and benzyl trichloroacetimidate (3.4 g, 14 mmol) in DCM (100 mL) was added trifluoromethanesulfonic acid (0.24 mL, 2.7 mmol) dropwise at 0° C. The resulting mixture was stirred at 0° C. for 6 h and warmed to room temperature. The mixture was washed with a saturated solution of NaHCO$_3$ (300 mL) and water (300 mL) and the organic layer dried over Na$_2$SO$_4$. The drying agent was removed by filtration, and the solvents removed using a rotary evaporator. The residue was purified by chromatography on silica gel (80 g RediSep column, eluting with a gradient of 0% through 30% ethyl acetate/hexanes over 60 min, 60 mL/min) to give the product 31 (1.2 g, 32%) as a colorless liquid. $^1$H NMR (300 MHz, CDCl$_3$) δ 7.30-7.05 (m, 5H), 4.51 (s, 2H), 3.90-3.80 (m, 1H), 3.70 (s, 3H), 2.58-2.45 (m, 2H), 1.80-1.60 (m, 2H), 1.50-1.20 (m, 18H), 0.85 (t, J=5.8 Hz, 3H).

Example 30

(R)-3-(BENZYLOXY)TETRADECANOIC ACID (33)

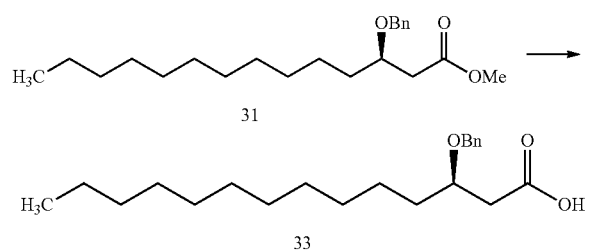

Ester 31 (1.3 g, 3.73 mmol) was dissolved in THF/MeOH/CH$_3$CN mixture (v/v/v, 1/1/1, 90 mL). Lithium hydroxide monohydrate (235 mg, 5.6 mmol) as a solution in water (30 mL) was added, and the mixture stirred overnight. The solvent amount was reduced in vacuo to about 30 mL. To the remaining aqueous solution was added 1 M hydrochloric acid to bring the pH down to 3. The aqueous layer was extracted with diethyl ether (3×40 mL). The combined organic extracts were dried over sodium sulfate. The drying agent was removed by filtration, and the solvents removed using a rotary evaporator. The residue was purified by chromatography on silica gel (40 g RediSep column, eluting with a gradient of 0% through 50% ethyl acetate/hexanes over 40 min, 40 mL/min) to give the product 33 (990 mg, 79%) as a colorless liquid. $^1$H NMR (300 MHz, CDCl$_3$) δ 7.30-7.05 (m, 5H), 4.51 (s, 2H), 3.90-3.80 (m, 1H), 2.58-2.45 (m, 2H), 1.80-1.60 (m, 2H), 1.50-1.20 (m, 18H), 0.85 (t, J=5.8 Hz, 3H).

Example 31

(R)-METHYL 3-(4-METHOXYBENZYLOXY)TETRADECANOATE (32)

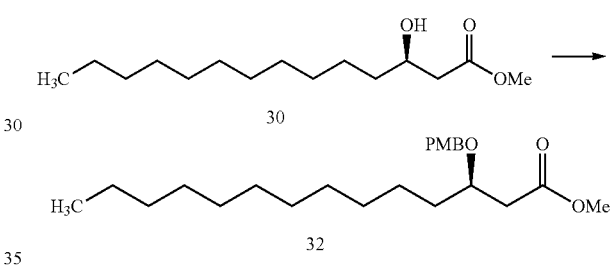

To a solution of compound 30 (3.50 g, 12.9 mmol) and 4-methoxybenzyl trichloroacetimidate (4.65 g, 17.3 mmol) in DCM (100 mL) was added camphorsulfonic acid (450 mg, 1.92 mmol). The mixture was stirred overnight at room temperature. The mixture was washed with a saturated solution of NaHCO$_3$ (300 mL) and water (300 mL) and dried over Na$_2$SO$_4$. The drying agent was removed by filtration and the solvents removed using a rotary evaporator. The residue was purified by chromatography on silica gel (120 g RediSep column, eluting with a gradient of 0% through 30% ethyl acetatethexanes over 70 min, 85 mL/min) to give the product 32 (4.01 g, 81%) as a colorless liquid.

Example 32

(R)-3-(4-METHOXYBENZYLOXY)TETRADECANOIC ACID (34)

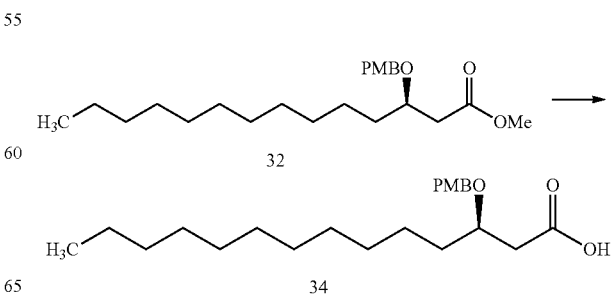

Ester 32 (4.01 g, 10.4 mmol) was dissolved in THF/MeOH/CH₃CN mixture (v/v/v, 1/1/1, 90 mL). Lithium hydroxide monohydrate (874 mg, 20.8 mmol) as a solution in water (30 mL) was added, and the mixture stirred overnight. The solvent amount was reduced in vacuo to about 30 mL. To the remaining aqueous solution was added hydrochloric acid (1 M) to bring the pH down to 3. The aqueous layer was extracted with diethyl ether (3×40 mL). The combined organic extracts were dried over sodium sulfate. The drying agent was removed by filtration and the solvents removed using a rotary evaporator. The residue was purified by chromatography on silica gel (120 g RediSep column, eluting with a gradient of 0% through 50% ethyl acetate/hexanes over 60 min, 85 mL/min) to give the product 34 (3.37 g, 89%) as a colorless liquid. ¹H NMR (300 MHz, CDCl₃) δ 7.22 (d, J=6.1 Hz, 2H), 6.82 (d, J=6.1 Hz, 2H), 4.46 (s, 2H), 3.81 (m, 1H), 3.75 (s, 3H), 2.65-2.49 (m, 2H), 1.80-1.60 (m, 2H), 1.50-1.20 (m, 18H), 0.85 (t, J=5.8 Hz, 3H).

Example 33

(R)-3-(4-METHOXYBENZYLOXY) TETRADECANOYL CHLORIDE (35)

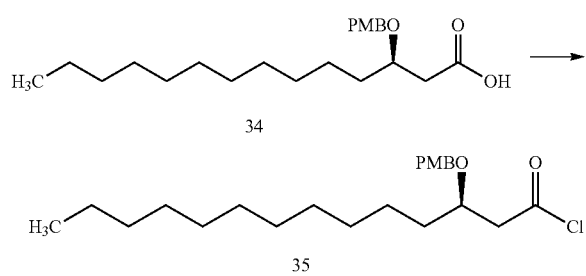

To a solution of acid 34 (500 mg, 1.37 mmol) in DCM (5 mL) was added dimethylformamide (DMF) (100 mg, 1.37 mmol), and the resulting mixture was cooled to −10° C. Oxalyl chloride (174 mg, 1.37 mmol) in DCM (5 mL) was added dropwise. The solution was allowed to warm to room temperature over 1 h. After TLC analysis showed no acid present, the mixture was concentrated in vacuo and used without further purification.

Example 34

(R)-2-OXO-2-PHENYLETHYL 3-HYDROXYTETRADECANOATE (37)

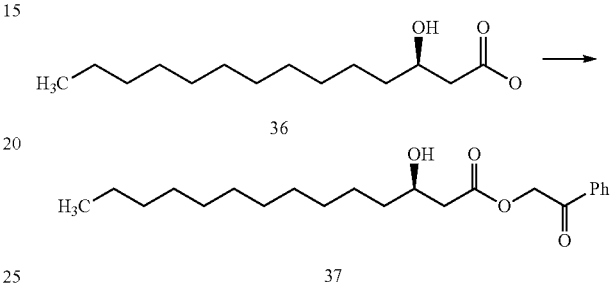

To a solution of (R)-3-hydroxytetradecanoic acid (36, see preparation below) (9.55 g, 39.1 mmol) and triethylamine (5.90 g, 58.6 mmol) in ethyl acetate (500 mL) was added 2-bromoacetophenone (7.90 g, 39.1 mmol) at room temperature. The mixture was stirred at room temperature for 14 h. The precipitate was removed by filtration, and the filtrate was concentrated in vacuo. The residue was purified by silica gel chromatography (120 g RediSep column, eluting with a gradient of 0% through 30% ethyl acetate/hexanes over 50 min, 85 mL/min) to give the product 37 (10.2 g, 72% yield) as a white solid.

Example 35

(R)-2-OXO-2-PHENYLETHYL-3-DECANOY-LOXYTETRADECANOATE (39)

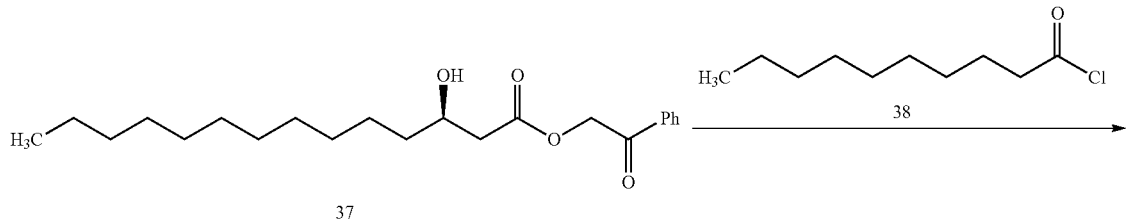

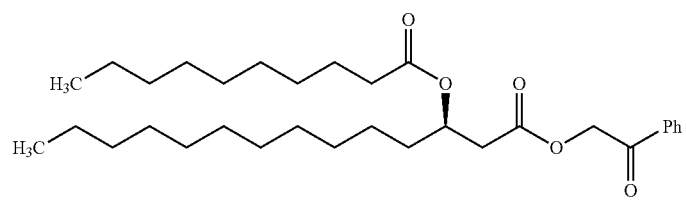

To a solution of 37 (4.80 g, 13.2 mmol) and pyridine (2.10 g, 26.5 mmol) in DCM (100 mL) at 0° C. was added decanoyl chloride (38, 2.8 g, 4.8 mmol). The mixture was stirred for 14 h allowing the temperature of the mixture to rise to room temperature. The mixture was washed with a saturated solution of NaHCO₃ (100 mL) and brine (100 mL) and dried over Na₂SO₄. The drying agent was removed by filtration and the solvents removed using a rotary evaporator. The residue was purified by chromatography on silica gel (120 g RediSep column, eluting with a gradient of 0% through 40% ethyl acetate/hexanes over 50 min, 85 mL/min) to give the product 39 (6.68 g, 97%) as a colorless liquid.

Example 36

(R)-3-(DECANOYLOXY)TETRADECANOIC ACID (40)

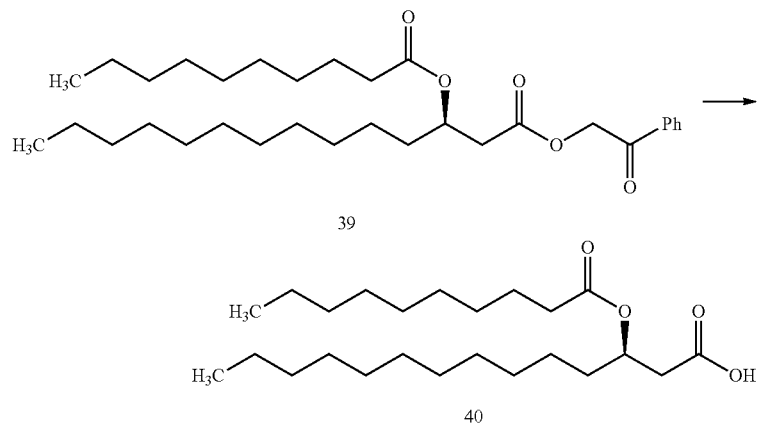

Ester 39 (10.15 g, 20.77 mmol) was dissolved in acetic acid (100 mL). Zinc (15.5 g, 237 mmol) was added, and the mixture heated to reflux for 4 h. The acetic acid was removed under vacuum and the residue azeotroped with toluene to dryness. The residue was purified by chromatography on silica gel (120 g RediSep column, eluting with a gradient of 0% through 60% ethyl acetate/hexanes over 50 min, 85 ml/min) to give the product 40 (7.2 g, 89%) as a colorless liquid. ¹H NMR (300 MHz, CDCl₃) δ 5.23-5.19 (m, 1H), 2.62-2.55 (m, 2H), 2.34-2.25 (m, 2H), 1.65-1.58 (m, 2H), 1.28-1.20 (m, 32H). 0.85 (m, 6H).

Example 37

(R)-METHYL 3-HYDROXYTETRADECANOATE (39)

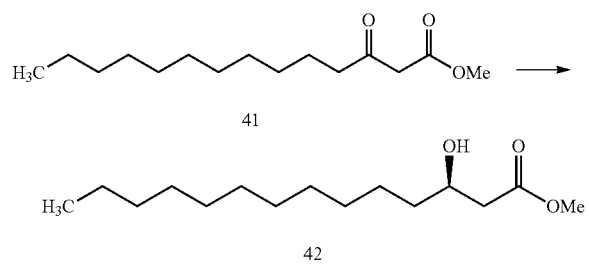

A slurry of methyl 3-oxotetradecanoate (41, 5.27 g, 20.6 mmol) in methanol (30 mL) in a 300 mL high pressure reactor glass sleeve was sparged with N₂ for 10 minutes. Dichloro-R-2,2'-bis(diphenylphosphino)-1,1'-binaphthylruthenium (142 mg, 1.1 mmol) was added and the mixture was placed in a Parr 5500 series compact reactor. The reactor was charged with H₂ (60 psi) and vented three times. The reactor was then charged with a final portion of H₂ (60 psi) stirred (600 rpm) and heated to 50° C. for 20 h. The reactor was then cooled to room temperature and the mixture concentrated in vacuo. The resulting residue was purified by silica gel chromatography, eluting with a gradient of 0% through 50% ethyl acetate/hexanes to provide 42 (3.97 g, 74%) as an off-white solid. ¹H NMR (CDCl₃) δ 4.00-3.98 (m, 1H), 3.71 (s, 3H), 2.82 (d, J=6.5 Hz, 1H), 2.62-2.30 (m, 2H), 1.54-1.39 (m, 3H), 1.27 (br s, 17H), (m, 20H), 0.86 (t, J=7.0 Hz, 3H).

Example 38

(R)-3-HYDROXYTETRADECANOIC ACID (36)

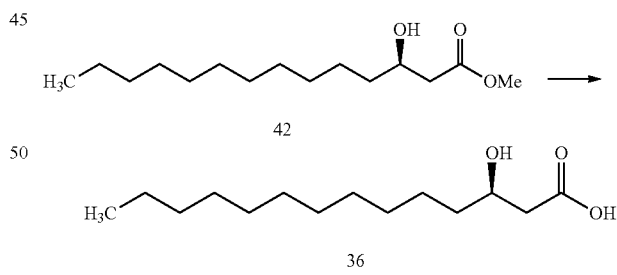

Lithium hydroxide monohydrate (1.98 g, 47.2 mmol) was added to a solution of (R)-methyl 3-hydroxytetradecanoate (42, 8.17 g, 31.5 mmol) in THF (66 mL) and water (66 mL) and stirred at room temperature for 2 h. The mixture was then diluted with diethyl ether (1 L) and the pH adjusted to ~3 with a solution of hydrochloric acid (1 N). The solution was then extracted with diethyl ether (200 mL), and the organic fractions were combined and dried over Na₂SO₄. Na₂SO₄ was removed by filtration and the filtrate was concentrated in vacuo to provide (R)-3-hydroxytetradecanoic acid (36, 7.59 g, 98%) as an off-white solid. ¹H NMR (CDCl$_3$) δ 3.99-3.94 (m, 1H), 2.45-2.39 (m, 2H), 1.47 (br s, 3H), 1.29 (br s, 17H), 0.89 (t, J=7.0 Hz, 3H).

Example 39

(R)-2-OXO-2-PHENYLETHYL-3-TETRADE-CANOYLOXYTETRADECANOATE (46)

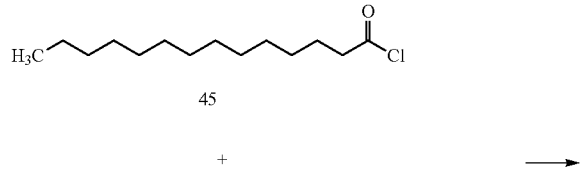

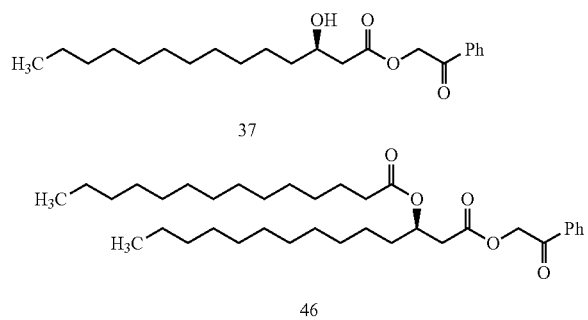

Myristoyl chloride (45, 8.83 g, 35.8 mmol) was added to a solution of (R)-2-oxo-2-phenylethyl 3-hydroxytetradecanoate (37, prepared according to Example 34, 10.8 g, 29.8 mmol) in pyridine (40 mL). The reaction mixture was stirred at room temperature for 14 h. The mixture was then concentrated in vacua, and the residual pyridine removed by dissolving the residue in toluene (100 mL) and concentrating in vacuo. The resulting residue was purified by silica gel chromatography, eluting with a gradient of 0% through 20% ethyl acetate/hexanes, to provide 46 (16.31 g, 83%) as a colorless oil. $^1$H NMR (CDCl$_3$) δ 7.90 (m, 2H), 7.64-7.57 (m, 1H), 7.50-7.45 (m, 2H), 5.33 (s, 2H), 5.31-5.27 (m, 1H), 2.80-2.70 (m, 2H), 2.33-2.26 (t, J=4.5 Hz, 2H), 1.65-1.58 (m, 2H), 1.31-1.21 (m, 40H), 0.85 (t, J=10.0 Hz. 6H).

Example 40

(R)-3-(TETRADECANOYLOXY)TETRADECANOIC ACID (47)

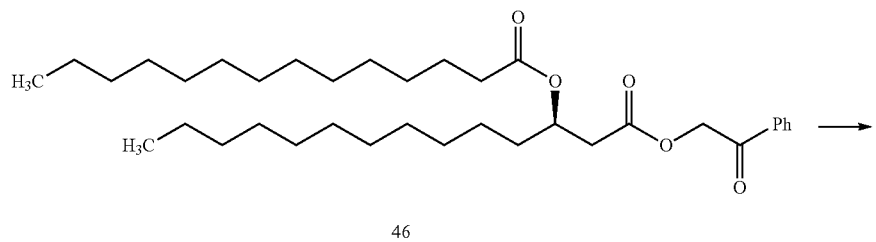

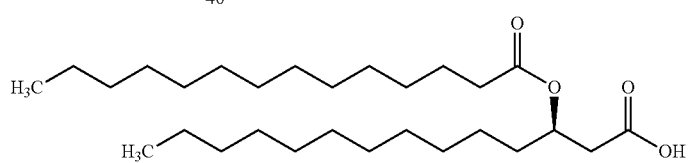

Zinc dust (24.42 g, 373.3 mmol) was added to a solution of 46 (16.28 g, 28.42 mmol) in acetic acid (150 mL). The mixture was then heated to reflux (115° C.) for 3 h. The mixture was then concentrated in vacuo, and the residual pyridine removed by dissolving the residue in toluene (100 mL) and concentrating in vacuo. The resulting residue was by silica gel chromatography, eluting with a gradient of 0% through 30% ethyl acetate/hexanes to provide (R)-benzyl 3-(tetradecanoyloxy)tetradecanoic acid (47, 11.14 g, 86% yield) as a colorless oil.

$^1$H NMR (CDCl$_3$) δ 5.29-5.18 (m, 1H), 2.62-2.55 (m, 2H), 2.34-2.25 (m, 2H), 1.65-1.58 (m, 3H), 1.28-1.20 (m, 40H), 0.85 (m, 6H).

Example 41

TERT-BUTYLDIMETHYLSILYL-2-AZIDO-4-O-BENZYL-2-DEOXY-O-D-GLUCOPYRANOSIDE (47)

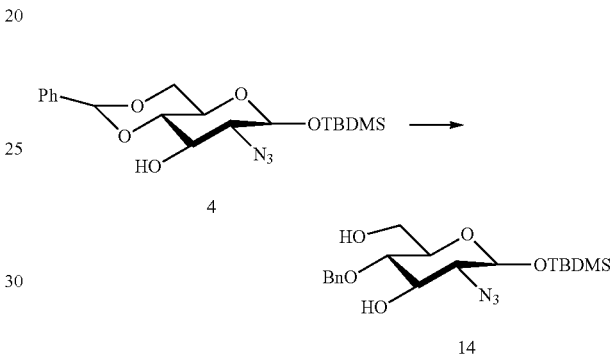

Compound 4 (prepared according to Example 3, 1.32 g, 3.36 mmol) was dissolved in a solution of BH$_2$ (1 M) in THF (18.1 mL, 18.1 mmol). After the mixture was stirred at 0° C. for 5 min, dibutylboron triflate (1 M in DCM, 3.62 mL, 3.62 mmol) was added dropwise, and the reaction mixture was stirred at 0° C. for another 1 h. Subsequently, triethylamine (0.5 mL) and methanol (~0.5 mL) were added until the evolution of H$_2$ gas had ceased. The solvents were evaporated in vacuo, and the residue was co-evaporated with methanol (3×50 mL). The residue was purified by silica gel column chromatography (hexanes/ethyl acetate, 8:1 (v/v)) to give 14 (0.67 g, 49%) as a colorless oil. R$_f$=0.40 (hexanes/ethyl acetate, 3:1 (v/v)). $^1$H NMR (500 MHz, CDCl$_3$) δ 7.32-7.31 (m, 5H), 4.81 (d, J=11.4 Hz, 1H), 4.70 (d, J=11.4

Hz, 1H), 4.55 (d, J=7.5 Hz, 1H), 3.84 (m, 1H), 3.70 (dd, 1H, J=12.0, 1.5 Hz, 1H), 3.49-3.43 (m, 2H), 3.33 (br s, 1H), 3.22-3.17 (m, 1H), 0.92 (s, 9H), 0.14 (s, 6H).

Example 42

INDUCTION OF TH1-TYPE IMMUNE RESPONSE IN VIVO

This example demonstrates in vivo Th1-type immunostimulant activity for an illustrative GLA compound of the invention having the following structure (IX):

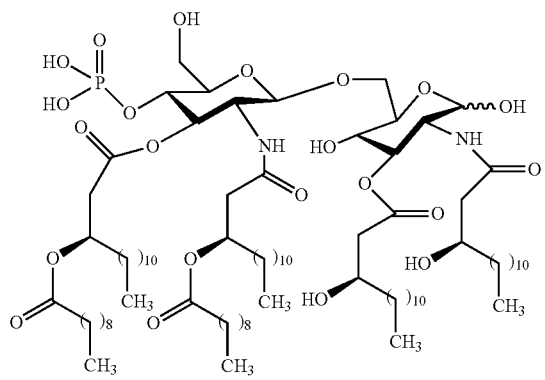

IX

Compound IX was used in a vaccine containing a *Mycobacterium tuberculosis* antigenic polypeptide referred to as ID83. Standard immunological methodologies and reagents were employed (Current Protocols in Immunology, Coligan et al. (Eds.) 2006 John Wiley & Sons, NY). Mice (four C57BL16 animals per group) were immunized three times at three-week intervals with ID83 antigen (8 µg per animal for each immunization) in water, ID83 antigen (8 µg per animal for each immunization) formulated in a stable emulsion vehicle, or ID83 antigen (8 µg per animal for each immunization) formulated in a stable emulsion containing (i) GLA-SE (10 µg per animal for each immunization), or (ii) Compound IX (10 µg per animal for each immunization).

One week after each injection, mice were bled to evaluate antigen-specific antibody (IgG1 and IgG2c) responses. Three weeks after the last immunization mice were sacrificed and spleens collected to analyze T cell-dependent IFN-γ cytokine responses to in vitro antigen stimulation by ELISPOT according to published methods (Id.). IFN-γ cytokine responses have been associated with a TH1 protective phenotype against *M. tuberculosis* infection.

FIG. 1 shows ELISPOT data of anti-ID83 IFN-γ cytokine production induced in mice three weeks after the third immunization using ID83 antigen and ID83 component antigens (Rv2608, Rv1813 and Rv3620) formulated with a stable emulsion (SE) of 10 µg Compound IX, compared to ID83 formulated in GLA-SE, SE or water. Means and SEM of IFN-γ secreting cells per million of splenocytes in each group are shown. "GLA-SE", as used in the Examples herein refers to a stable emulsion of a compound as described in co-owned U.S. Patent Publication No. 20080131466, wherein $R^1$, $R^3$, $R^5$ and $R^6$ are $C_{11}$ linear alkyl; and $R^2$ and $R^4$ are $C_{13}$ linear alkyl.

All animals responded equivalently to ConA, a potent cell activator and mitogen. ID83+Compound IX vaccination induced robust ID83 antigen-specific cytokine responses, while little or no such responses were observed in the ID83+water or ID83+SE control groups. Similar levels of IFN-γ secreting cells were elicited in splenocytes purified from mice immunized with ID83+Compound IX or ID83+ GLA-SE upon restimulation with the ID83 component antigens, Rv2608, Rv1813 and Rv3620.

In conclusion, Compound IX in a stable oil formulation with *M. tuberculosis* vaccine antigen candidate ID83 induced predominantly antigen-specific immune responses of the cellular type (T cell) associated with the protective TH1 phenotype.

Example 43

INDUCTION OF TH1- AND TH2-TYPE IMMUNE RESPONSES IN VIVO

This example demonstrates in vivo Th1- and Th2-type immunostimulant activity of Compound IX in a vaccine containing a Mycobacterium tuberculosis antigen referred to as ID83. Standard immunological methodologies and reagents were employed (Current Protocols in Immunology, Coligan et al. (Eds.) 2006 John Wiley & Sons, NY).

Mice (four C57BL/6 animals per group) were immunized three times at three-week intervals with the ID83 antigen (8 µg per animal for each immunization) used alone or formulated in a stable emulsion containing Compound IX (10 µg per animal for each immunization). Sera were collected by bleeding animals one week after each immunization, and serum levels of IgG1 and IgG2c antibodies specific for ID83 were examined by ELISA according to published methods (Id.) Predominance of either IgG1 or IgG2c antibody isotype is associated with TH2 or TH1 responses, respectively. It has been demonstrated that a TH1 response is necessary for protection against Mycobacterium tuberculosis infection.

As shown in FIG. 2, vaccination with ID83 in water induced predominantly antigen-specific IgG1 antibody. In contrast, ID83+SE, ID83+Compound IX-SE or ID83 GLA-SE vaccination induced higher IgG2c antibody titers, and converted the phenotype to a mixed IgG1:IgG2c antigen-specific antibody response.

Example 44

INDUCTION OF TLR4-DEPENDENT IMMUNOSTIMULATION IN HUMAN CELLS

Figure 3:
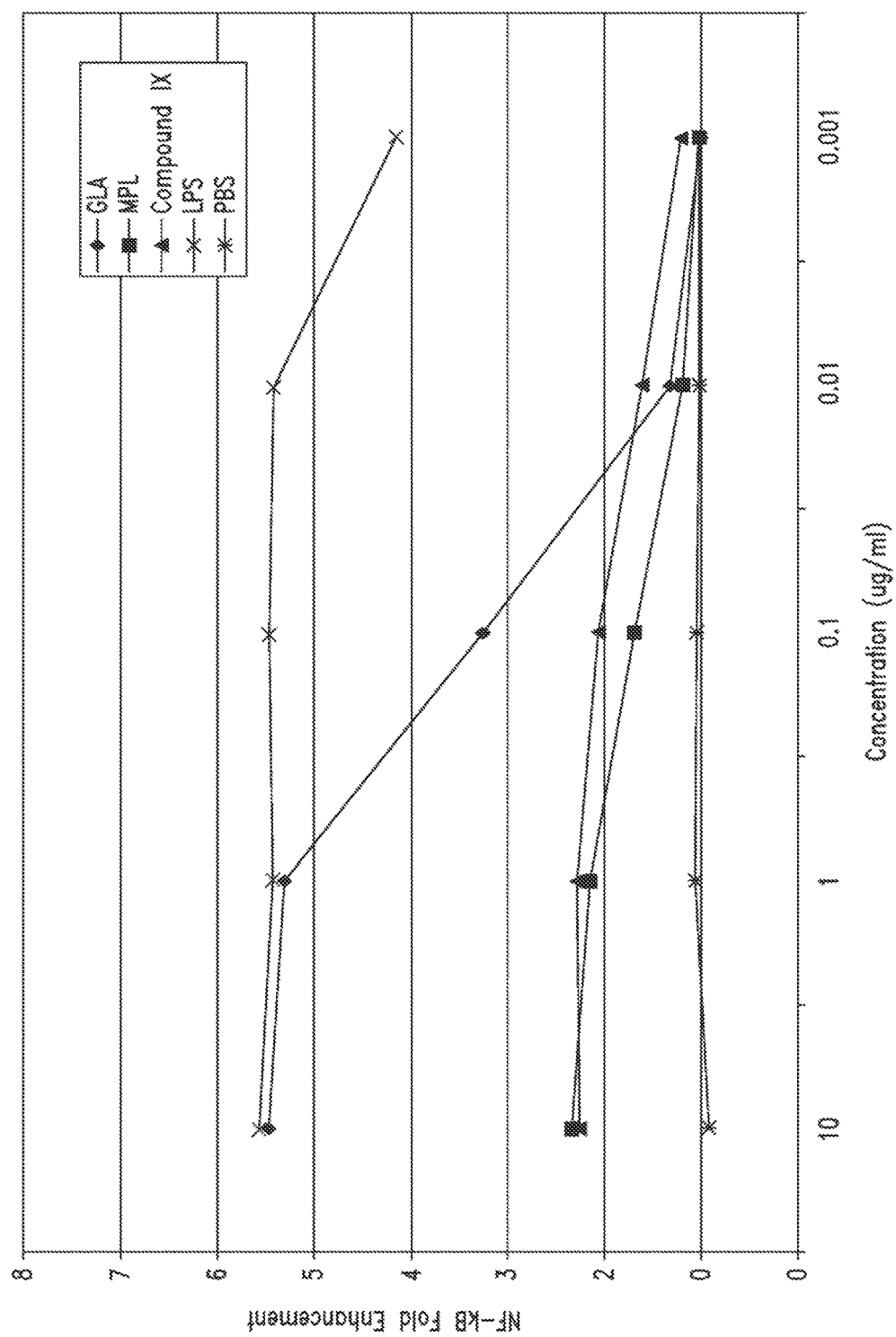
FIG. 3 shows the NF-kB enhancement observed at different concentrations of an illustrative GLA compound of the invention (Compound IX).

This example demonstrates the immunostimulatory activity of Compound IX in human cells. Compound IX was tested in vitro using HEK 293 cells (InvivoGen) with expression vectors encoding 1) TLR4, MD-2, and CD14, or 2) TLR2 and TLR6 to define compound activity and dependence on TLR4, and to exclude activation of TLR2. These HEK 293 cell lines were further stably transfected with the NF-kB reporter vector pNifty-2 such that alkaline phosphatase is secreted into the growth media upon activation of the TLR signaling pathway. Transfected cell lines were plated at $5 \times 10^4$ cells per well in a 96-well plates and stimulated for 16-24 hours cultured in medium containing serial dilutions of Compound IX and other adjuvants. Secreted alkaline phosphatase activity was measured in the culture media using QUANTIBlue® assay (InvivoGen). The data was measured as enhancement of NF-kB above the PBS negative control. Using this assay, Compound IX showed greater than two-fold enhancement of NF-kB at concentrations as low as 0.1 µg/ml (FIG. 3). The results of these experiments demonstrated clear TLR4 agonist activity for Compound IX that did not appear to be associated with induction of TLR2. Compound IX was designed based on structural considerations of the reported atomic structure of MD2 and TLR4. As such, the fact that it binds and elicits a profile that is similar to that of a commercially approved TLR4 agonist (MPL®) is a surprising and unexpected result. More specifically, the profile for Compound IX advantageously plateaus rapidly as concentrations are increased, before one would expect the cytokine levels to rise to a point where negative side effects may exert themselves. Thus, it is expected that Compound IX and other illustrative compounds of the invention can be safely administered over a broad range of concentrations, which is highly desirable in the context of reproducibility of clinical outcomes among patients and for the safety in ranging a dose for adults and children. In this respect, the lower cytokine activity for Compound IX is a surprising and desirable result that will further facilitate its safe use in clinical formulations.

Example 45

INDUCTION OF IMMUNOSTIMULATORY CYTOKINES IN HUMAN BLOOD CELLS

Figure 4A:
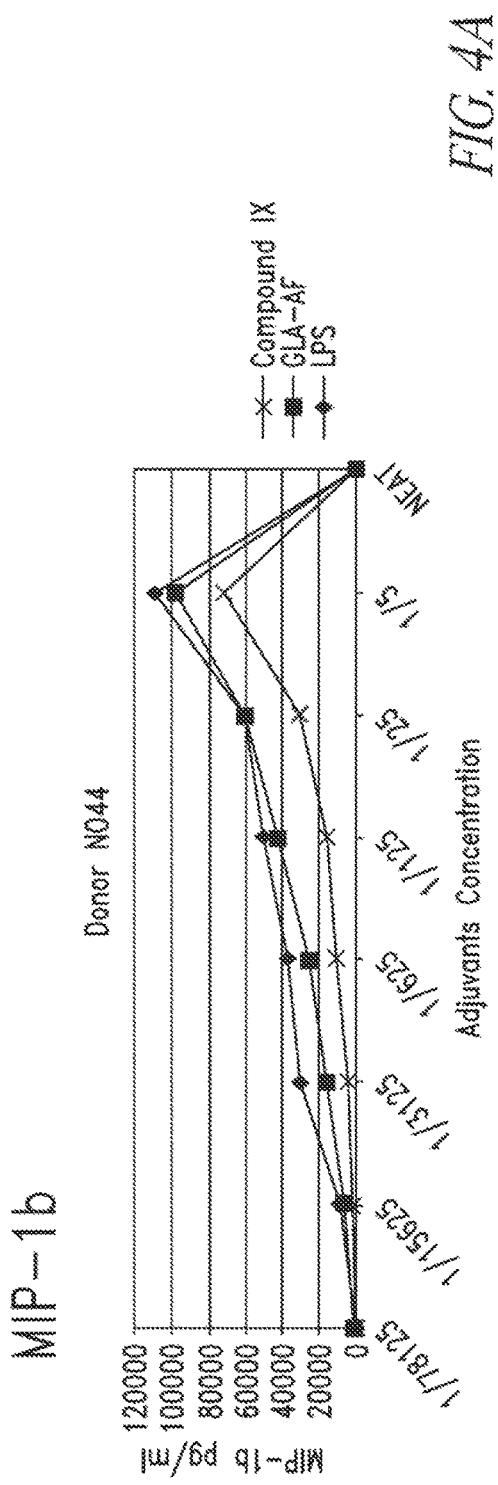
FIGS. 4A-4D show the induction of immunostimulatory cytokines (MIP-1b and TNFa) at different concentrations of an illustrative GLA compound of the invention (Compound IX).
Figure 4B:
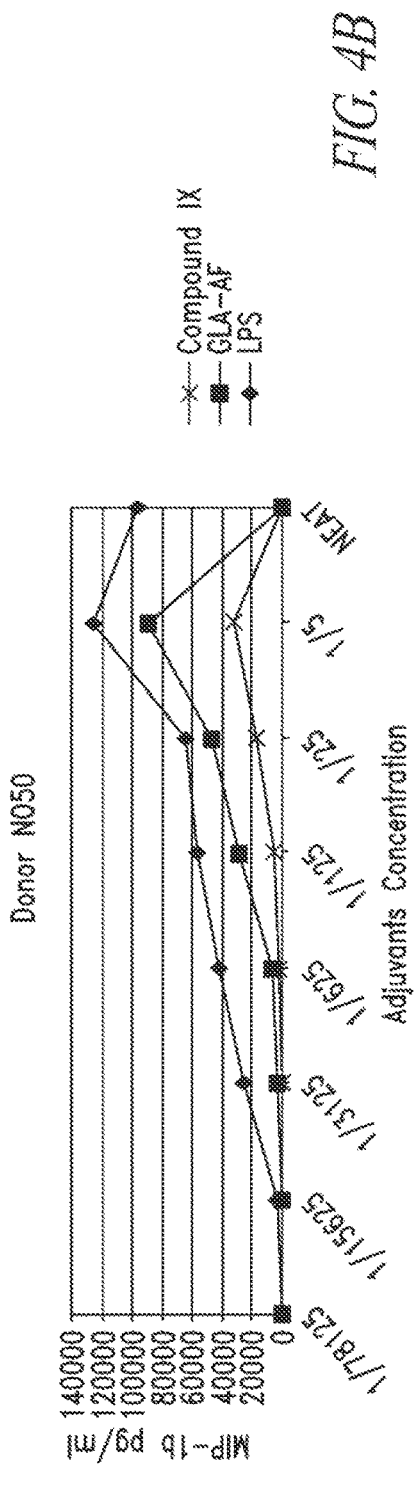
Figures 4C, 4D:
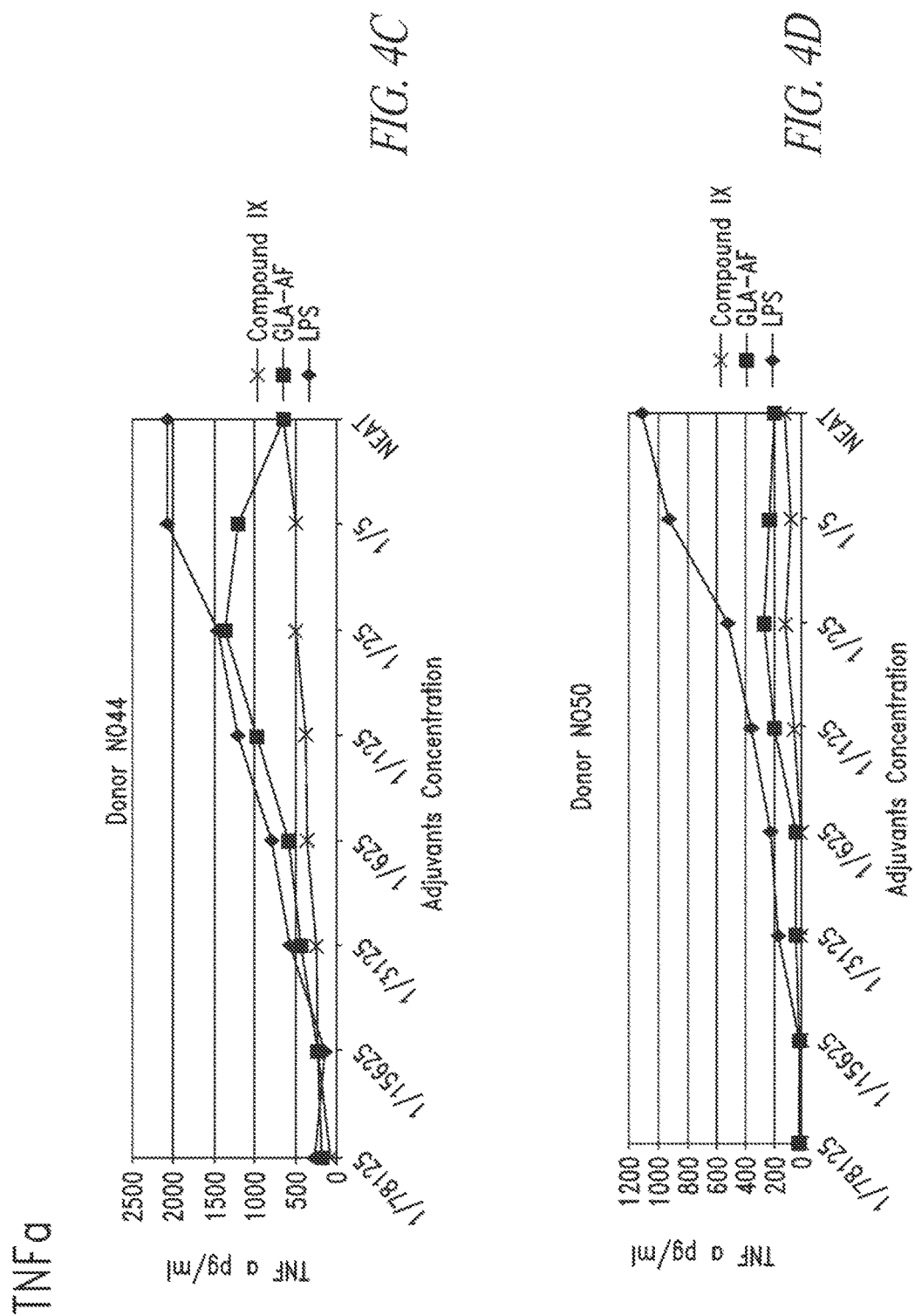

In this example, human whole blood cells were stimulated with Compound IX and ELISA assays were performed to detect the induction of immunostimulatory cytokines. Serial dilutions (1:5) of Compound IX and other adjuvants were performed with phosphate buffered saline in a 96 well plate for a total of 7 dilutions. 100 µl of freshly drawn human blood from two different donors were mixed and incubated with 100 µl of adjuvant dilutions. Following a 20 hour incubation, plates were centrifuged and supernatants (~70 µl) were collected, avoiding red blood cells, and stored at −20° C. prior performing MIP-1-α and TNF-= ELISAs using standard biochemical procedures. The results of these experiments further confirmed that Compound IX has immunostimulatory activity in primary human blood cells (FIG. 4). Additionally, these primary donor results mimicked the results seen in human cell lines and extend these important findings in relation to the possible dose ranges and safety profiles for this compound.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A GLA compound having the following structure (III):

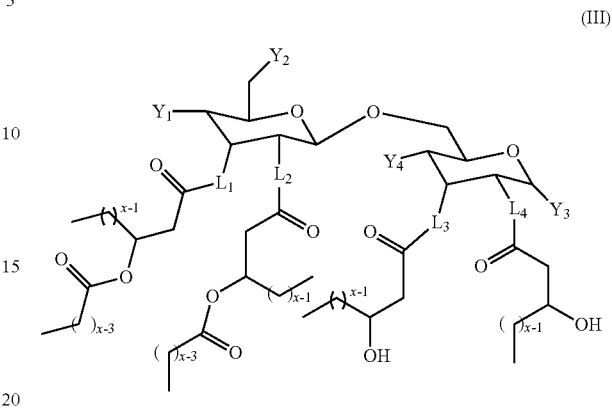

(III)

or a pharmaceutically acceptable salt thereof, wherein:
x is constant and is selected from an integer from 8-13;
$L_1$, $L_2$, $L_3$, and $L_4$, are the same or different and independently —O—, —NH— or —(CH2)-;
$Y_1$ is an acid functional group;
$Y_2$ and $Y_3$ are the same or different and independently —OH, —SH, or an acid functional group; and
$Y_4$ is —OH or —SH.

2. The GLA compound according to claim 1, wherein x is selected from an integer from 10-12.

3. The GLA compound according to claim 1, wherein $Y_1$ is —OP(=O)(OH)$_2$; $Y_2$, $Y_3$, and $Y_4$ are each —OH; $R_1$, $R_3$, $R_5$, and $R_6$ are each $C_x$ alkyl; $R_2$ and $R_4$ are both $C_{x-2}$ alkyl; and the GLA compound has the following formula (V):

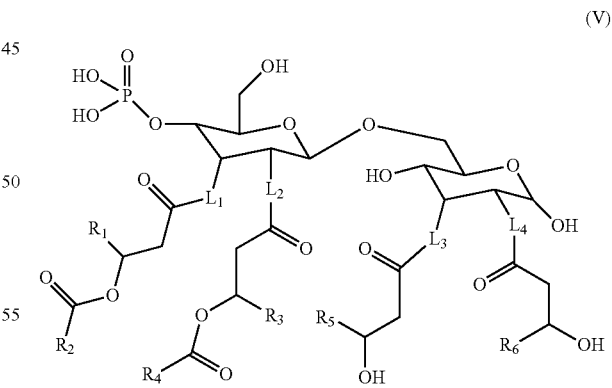

(V)

or a pharmaceutically acceptable salt thereof.

4. The GLA compound according to claim 1, wherein $L_1$ and $L_3$ are both —O—; $L_2$ and $L_4$ are both —NH—; $R_1$, $R_3$, $R_5$, and $R_6$ are each $C_x$ alkyl; $R_2$ and $R_4$ are both $C_{x-2}$ alkyl; and the GLA compound has the following formula (VI):

(VI)

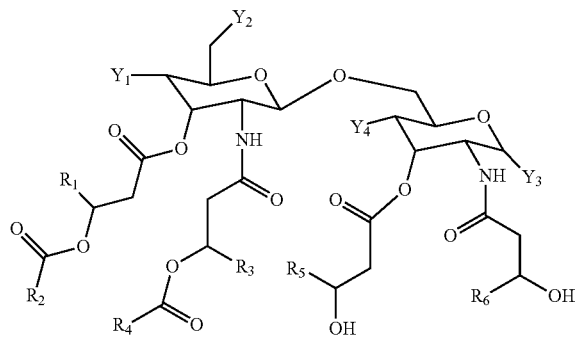

or a pharmaceutically acceptable salt thereof.

5. The GLA compound according to claim 1, wherein $Y_1$ is —OP(O)(OH)$_2$; $Y_2$, $Y_3$, and $Y_4$ are each —OH; $L_1$ and $L_3$ are both —O—; $L_2$ and $L_4$ are both —NH—; $R_1$, $R_3$, $R_5$, and $R_6$ are each $C_x$ alkyl; $R_2$ and $R_4$ are both $C_{x-2}$ alkyl; and the GLA compound has the following formula (VII):

(VII)

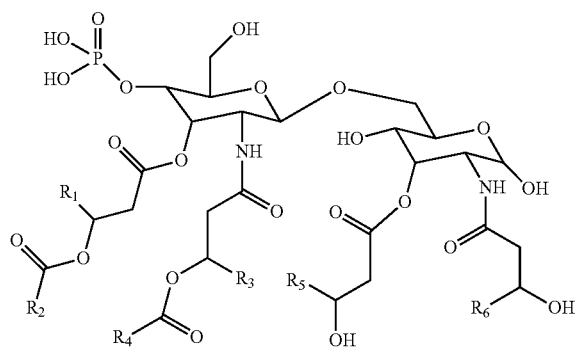

or a pharmaceutically acceptable salt thereof.

6. The GLA compound according to claim 1, wherein $Y_1$ is —OP(O)(OH)$_2$; $Y_2$, $Y_3$, and $Y_4$ are each —OH; $L_1$ and $L_3$ are both —O—; $L_2$ and $L_4$ are both —NH—; $R_1$, $R_3$, $R_5$, and $R_6$ each are $C_x$ alkyl; and $R_2$ and $R_4$ are both $C_{x-2}$ alkyl and the GLA compound has the following formula (VIII):

(VIII)

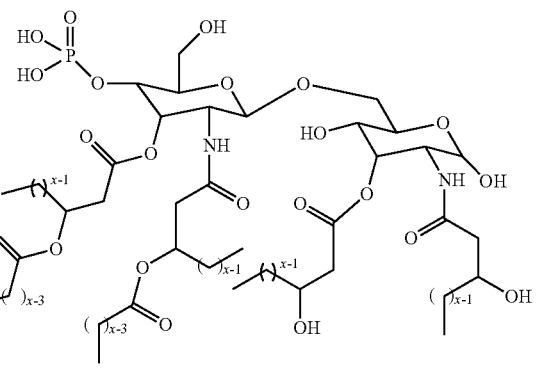

or a pharmaceutically acceptable salt thereof.

7. A vaccine composition comprising the GLA compound of claim 1 in combination with an antigen or a recombinant expression vector encoding an antigen.

8. The vaccine composition of claim 7 wherein the recombinant expression vector is a viral vector.

9. The vaccine composition of claim 7, wherein the antigen is a *Mycobacterium tuberculosis* antigenic polypeptide.

10. The vaccine composition of claim 7, wherein the recombinant expression vector encodes one or more of TLR4, MD-2, CD14, TLR2, or TLR6.

11. A method of eliciting or enhancing an antigen-specific immune response in a subject, the method comprising administering to the subject a vaccine composition of claim 7.

12. A pharmaceutical composition comprising the GLA compound of claim 1 and a pharmaceutically acceptable carrier or excipient.

13. The pharmaceutical composition of claim 12, wherein the pharmaceutically acceptable carrier is a stable squalene emulsion.

14. A method for stimulating a non-specific immune response in a subject comprising administering to the subject a pharmaceutical composition of claim 12.

15. The method of claim 14, wherein the non-specific immune response comprises induction of immunostimulatory cytokines.

* * * * *